United States Patent [19]

Mizukawa et al.

[11] Patent Number: 5,451,501
[45] Date of Patent: Sep. 19, 1995

[54] PHOTOGRAPHIC COUPLER AND SILVER HALIDE COLOR PHOTOGRAPHIC MATERIAL

[75] Inventors: Yuki Mizukawa; Masuji Motoki; Tadahisa Sato; Osamu Takahashi, all of Kanagawa, Japan

[73] Assignee: Fuji Photo Film Co., Ltd., Kawagawa, Japan

[21] Appl. No.: 67,111

[22] Filed: May 26, 1993

[30] Foreign Application Priority Data

May 26, 1992 [JP] Japan ............................ 4-157405
Aug. 11, 1992 [JP] Japan ............................ 4-234120

[51] Int. Cl.$^6$ ......................................... G03C 7/38
[52] U.S. Cl. ............................... 430/558; 430/386; 430/387
[58] Field of Search ................. 430/558, 386, 387

[56] References Cited

U.S. PATENT DOCUMENTS

| 4,540,654 | 9/1985 | Sato et al. ............... 430/381 |
| 4,621,046 | 11/1986 | Sato et al. ............... 430/381 |
| 4,639,415 | 1/1987 | Kaneko et al. .......... 430/558 |
| 4,845,022 | 7/1989 | Wolff ...................... 430/558 |
| 4,873,183 | 10/1989 | Tachibana et al. ..... 430/558 |
| 4,882,266 | 11/1989 | Kawagishi et al. ..... 430/546 |
| 4,914,008 | 4/1990 | Kurematsu et al. .... 430/558 |
| 5,298,375 | 3/1994 | Deguchi .................. 430/558 |
| 5,356,763 | 10/1994 | Takahashi et al. ..... 430/558 |

FOREIGN PATENT DOCUMENTS

| 0476949 | 3/1992 | European Pat. Off. |
| 0249053 | 11/1986 | Japan . |
| 1250955 | 10/1989 | Japan . |
| 348845 | 1/1991 | Japan . |
| 5-80473 | 4/1993 | Japan . |

Primary Examiner—Lee C. Wright
Attorney, Agent, or Firm—Birch, Stewart, Kolasch & Birch

[57] ABSTRACT

A 1H-pyrazolo[1,5-b][1,2,4]triazole magenta coupler having a t-alkyl group at the position-6 and an amido group-substituted phenyl group at the position-2 is disclosed. There is also disclosed a silver halide color photographic material containing the same.

21 Claims, 1 Drawing Sheet

PHOTOGRAPHIC COUPLER AND SILVER HALIDE COLOR PHOTOGRAPHIC MATERIAL

FIELD OF THE INVENTION

This invention relates to a photographic coupler and a silver halide color photographic material (hereinafter referred to simply as light-sensitive material). More particularly, it relates to a 1H-pyrazolo[1,5-b]-[1,2,4]-triazole magenta coupler and a light-sensitive material containing the same.

BACKGROUND OF THE INVENTION

1H-Pyrazolo[1,5-b][1,2,4]triazole magenta couplers are disclosed in JP-A-59-171956 (corresponding to U.S. Pat. No. 4,621,046) (the terms "JP-A" as used herein means an "unexamined published Japanese patent application") and U.S. Pat. No. 4,540,654. It is known that these couplers are excellent in color reproducibility and are preferred from the viewpoint of synthesis. It is also known that the couplers give a dye image having excellent fastness when used together with certain kinds of anti-fading agents. JP-A-1-302249 (corresponding to U.S. Pat. No. 4,882,266) discloses couplers which give a dye image having further improved fastness. Namely, the couplers are 1H-pyrazolo[1,5-b][1,2,4]triazole magenta couplers having a tertiary alkyl group at the position-6 and a phenylene group at the position-2. Dye images formed from these couplers have high fastness to light and heat. The concretely exemplified compounds of the couplers described in U.S. Pat. No. 4,882,266 are couplers wherein the phenylene group at the position-2 has a sulfonamido group at the meta-position. It has been found that dyes obtained from couplers wherein the phenylene group at the position-2 has a substituent group at the meta-position have spectral absorption characteristics. Namely, absorption on the foot of the long wavelength side is large and broadened. Accordingly, a further improvement has been demanded from the viewpoint of color reproducibility.

Further, it has been found that light-sensitive materials containing these couplers have a problem in that the photographic performance thereof is changed during the course of storage, until development, after exposure.

Furthermore, there has been a demand to provide light-sensitive materials which are scarcely changed in photographic characteristics by a change in the composition of a processing solution in development. Changes in the composition of processing solutions are mainly caused by (1) an increase in the mixing and accumulation of the ingredients of other processing solutions in running processing or (2) intermittently continuous processing conducted using automatic processors. This phenomenon is remarkable when the replenishment rates of the processing solutions are reduced and the ratios of tank solutions refreshed by replenishers are lowered or when the use of the processing solutions is prolonged. The above description "the mixing of the ingredients of other processing solutions" is caused by the splash of an adjoining processing solution during processing, or back contamination which is a phenomenon wherein ingredients in the processing solutions immediately after development are brought into a color developing solution by a conveying leader or belt or hangers which hang films. When the light-sensitive materials containing couplers described in U.S. Pat. No. 4,882,266 are processed with a color developing solution containing fixing agents in a contaminant amount by the ingredients becomming mixed and accumulated, photographic characteristics are greatly changed. Hence, a further improvement has been demanded.

Further, light-sensitive materials containing couplers wherein a phenylene group at the position-2 has a methyl group at the ortho-position as described in JP-A-3-48845 have a problem in that color developability is low in addition to the above-described problem. Accordingly, a further improvement has been demanded.

SUMMARY OF THE INVENTION

Accordingly, an object of the present invention is to provide a 1H-pyrazolo[1,5-b][1,2,4]triazole magenta coupler capable of forming a magenta dye having excellent spectral absorption characteristics and a light-sensitive material having excellent color reproducibility.

Another object of the present invention is to provide a light-sensitive material which scarcely changes in photographic characteristics, with a change in the compositions of the processing solutions utilized.

Still another object of the present invention is to provide a 1 H-pyrazolo[1,5-b][1,2,4]triazole magenta coupler which gives a dye image having excellent fastness to light and heat and a light-sensitive material containing the same.

The above-described objects of the present invention have been achieved by providing a coupler represented by the following general formula [I] and a silver halide color photographic material containing the same.

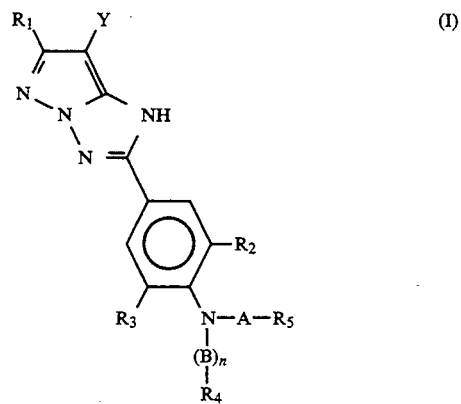

wherein $R_1$ represents a tertiary alkyl group; $R_2$ and $R_3$ each represents hydrogen atom or a substituent group; Y represents hydrogen atom, a halogen atom or an aryloxy group; A and B each represents —CO— or —SO$_2$—; n represents 0 or 1; $R_4$ represents hydrogen atom, an alkyl group or an aryl group; and $R_5$ represents an alkyl group, an aryl group, an alkoxy group, an alkylamino group or an arylamino group; or $R_4$ and $R_5$ may be combined together to form a five-membered, six-membered or seven-membered ring.

DETAILED DESCRIPTION OF THE INVENTION

Figure 1:
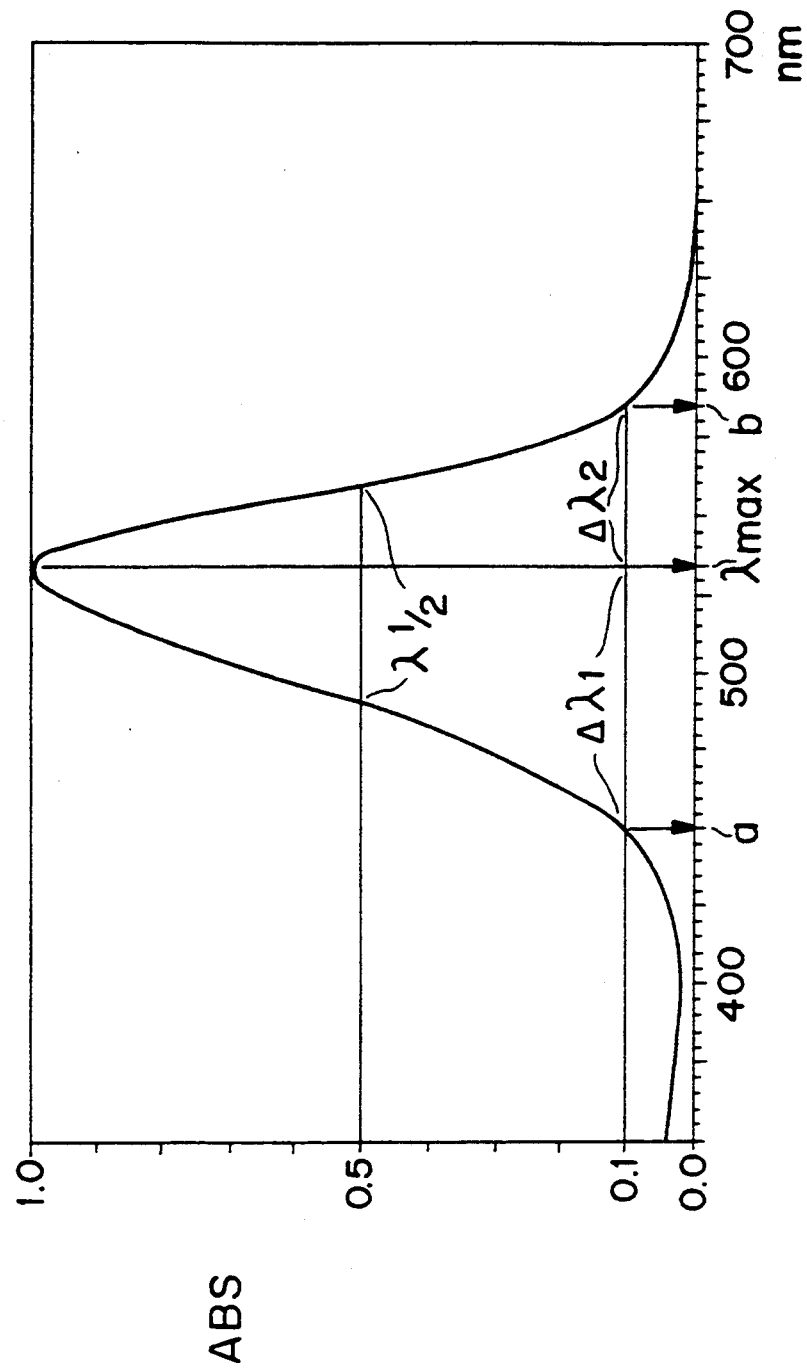
FIG. 1 is a visible absorption spectrum of an ethyl acetate solution of a dye to determine maximum absorption wavelength (λmax), an extinction coefficient (ε), a half width (λ/2), a value (Δλ$_1$) which represents a degree of the cut of the foot on the short wavelength side and a value (Δλ$_2$) which represents a degree of the cut of the foot on the long wavelength side.

The couplers of general formula [I] will be illustrated in more detail below.

$R_1$ is a tertiary alkyl group which may optionally have one or more substituent groups or may form a ring together with a branched alkyl group. Examples of the substituent groups include a halogen atom (e.g., fluorine, chlorine), an aryl group (e.g., phenyl, naphthyl), an alkoxy group (e.g., methoxy, ethoxy, dodecyloxy, 2-methoxyethoxy, 2-phenoxyethoxy), an aryloxy group (e.g., phenoxy, 2-methoxyphenoxy, 4-t-octylphenoxy, naphthoxy, 2,6-dimethoxyphenoxy), an alkylthio group (e.g., methylthio, ethylthio, butylthio, hexylthio, octylthio, hexadecylthio, 2-ethoxycarbonylpropylthio), an arylthio group (e.g., phenylthio, 2-pivaloylamidophenylthio, 2-butoxy-t-octylphenylthio, naphthylthio, 2-butoxycarbonylphenylthio), an alkylcarbonyloxy group (e.g., acetyloxy, propionyloxy, heptanoyloxy, 2-ethylhexanoyloxy, cyclohexanoyloxy, pivaloyloxy), an arylcarbonyloxy group (e.g., benzoyloxy, 2-butoxybenzoyloxy, 2,5-dichlorobenzoyloxy, 3-octyloxycarbonylbenzoyloxy), an alkoxycarbonyl group (e.g., methoxycarbonyl, ethoxycarbonyl, propyloxycarbonyl, butoxycabonyl, octylcarbonyl, dodecyloxycarbonyl, 2-ethylhexyloxycarbonyl), a carbonamido group (e.g., acetamido, propaneamido, hexadecaneamido, pivaloylamido, benzamido, 2-ethoxybenzamido, 3-dodecyloxycarbonylpropaneamido, 4-tetradecyloxycarbonylbutaneamido), a sulfonamido group (e.g., methanesulfonamido, butanesulfonamido, octanesulfonamido, hexadecanesulfonamido, benzenesulfonamido, p-toluenesulfonamido, 2-octyloxy-5-t-octylbenzensesulfonamideo), carboxyl group and cyano group. Examples of $R_1$ in the form of a ring together with a branched alkyl group include 1-methylcyclopropyl group, 1-ethylcyclopropyl group and an adamantyl group. Most preferably, $R_1$ is a t-butyl group.

$R_2$ and $R_3$ may be the same or different and each is hydrogen atom or a substituent group. Preferred examples of the substituent group include a cyano group, hydroxyl group, carboxyl group, a halogen atom (e.g., fluorine, bromine), an alkyl group (e.g., methyl, ethyl, propyl, butyl, t-butyl), an aryl group (e.g., phenyl), an alkoxy group (e.g., methoxy, ethoxy, propyloxy, butoxy, dodecyloxy, 2-ethoxyethoxy, 2-phenoxyethoxy), an aryloxy group (e.g., phenoxy, 4-methoxyphenoxy, 2methoxyphenoxy, 4-methylphenoxy, 4-chlorophenoxy, 4-t-butylphenoxy, 2,4-dimethylphenoxy, 2-ethoxycarbonylphenoxy), an alkoxycarbonyl group (e.g., methoxycarbonyl, ethoxycarbonyl, octyloxycarbonyl, hexadecyloxycarbonyl), a carbamoyl group (e.g., N-ethylcarbamoyl, N-dodecylcarbamoyl, N-cyclohexylcarbamoyl, N,N-dibutylcarbamoyl, N-phenylcarbamoyl), and a sulfamoyl group (e.g., N-ethylsulfamoyl, N-butylsulfamoyl, N-octylsulfamoyl, N-hexadecylsulfamoyl, N-cyclohexylsulfamoyl, N,N-dibutylsulfamoyl, N-methyl-N-octadecylsulfamoyl).

In the present invention, there are preferred the cases where $R_2$ is hydrogen atom and $R_3$ is a hydrogen atom, an alkyl group or an alkoxy group. Most preferred are the cases where $R_2$ and $R_3$ are hydrogen atom.

$R_4$ is hydrogen atom, an alkyl group or an aryl group. The alkyl group includes a substituted or unsubstituted straight-chain or branched alkyl group. Examples of substituent groups for the substituted alkyl group include a halogen atom (e.g., fluorine, chlorine, bromine), hydroxyl group, cyano group, carboxyl group, an aryl group (e.g., phenyl, naphthyl), an alkoxy group (e.g., methoxy, ethoxy, propyloxy, butoxy, dodecyloxy, 2-methoxyethoxy, 2-phenoxyethoxy), an aryloxy group (e.g., phenoxy, 2-methoxyphenoxy, 4-methoxyphenoxy, 2-methylphenoxy, 4-methylphenoxy, 2,4-dimethylphenoxy, 2,4-di-t-amylphenoxy, 4-t-octylphenoxy, 4-cyanophenoxy, 2-chloro-4-t-octylphenxoy, 4-methanesulfonamidophenoxy, 3-t-butyl-4-hydroxyphenoxy), an alkylthio group (e.g., methylthio, ethylthio, butylthio, octylthio, dodecylthio, hexadecylthio, 2-ethylhexylthio, 2-phenoxyethylthio, 1-ethoxycarbonyltridecylthio), an arylthio group (e.g., phenylthio, 2-pivaloylamidophenylthio, 4-t-octylphenylthio, 4-dodecyloxyphenylthio, 2-butoxy-4-t-octylphenylthio), an oxycarbonyl group (e.g., methoxycarbonyl, ethoxycarbonyl, propyloxycarbonyl, butoxycarbonyl, octyloxycarbonyl, dodecyloxycarbonyl, hexadecyloxycarbonyl, 2-methoxyethoxycarbonyl), a carbonyloxy group (e.g., acetyloxy, propionyloxy, dodecanoyloxy, tetradecanoyloxy, hexadecanoyloxy, benzoyloxy, 2-hexadecyloxybenzoyloxy), a carbonamido group (e.g., acetamido, propaneamido, butaneamido, hexaneamido, 2-ethylhexaneamido, dodecaneamido, hexadecaneamido, benzamido, 2-dodecyloxybenzamido, 3-tetradecyloxycarbonylbenzamido, 3-hexadecylsulfamoylbenzamido), a sulfonamido group (e.g., methanesulfonamido, ethanesulfonamido, octanesulfonamido, hexadecanesulfonamido, benzenesulfonamido, p-toluenesulfonamido, 2-octyloxy-5-t-octylbenzenesulfonamido, 3-hexadecyloxycarbonylbenzenesulfonamido, 3-dodecyloxycarbonylbenzeneulfonamido), a carbamoyl group (e.g., N-methylcarbamoyl, N-butylcarbamoyl, N-cyclohexylcarbamoyl, N-dodecylcarbamoyl, N-phenylcarbamoyl, N,N-diethylcarbamoyl, N,N-dibutylcarbamoyl), a sulfamoyl group (e.g., N-ethylsulfamoyl, N-butylsulfamoyl, N-hexadecylsulfamoyl, N-cyclohexylsulfamoyl, N,N-dibutylsulfamoyl, N-phenylsulfamoyl, N-methyl-N-octadecylsulfamoyl), an imido group (e.g., succinimido, phthalimido, hexadecylsuccinimido, octadecylsuccinimido), a urethane group (e.g., methylurethane, ethylurethane, dodecylurethane, phenylurethane), a ureido group (e.g., N-methylureido, N-ethylureido, N-dodecylureido, N,N-dibutylureido, N-phenylureido, N-cyclohexylureido) and a sulfonyl group (e.g., methylsulfonyl, ethylsulfonyl, propylsulfonyl, butylsulfonyl, hexylsulfonyl, octylsulfonyl, dodecylsulfonyl, hexadecylsulfonyl, phenylsulfonyl). The aryl group includes a substituted or unsubstituted aryl group such as phenyl group, naphthyl group, etc. Examples of substituent groups for the substituted aryl group include those already described above in the definition of the substituent groups for the substituted alkyl group represented by $R_4$. The oxycarbonyl group defined above is preferably alkyl or aryl oxycarbonyl group, and the carbonyloxy group, carbonamido group, sulfonamide group and sulfonyl group, which are defined above, are also preferable those connected to alkyl or aryl moiety, respectively.

$R_5$ is an alkyl group, an aryl group, an alkoxy group, an alkylamino group or an arylamino group. The alkyl group includes a substituted or unsubstituted straight-chain or branched alkyl group. Examples of substituent groups for the substituted alkyl group include those already described above in the definition of the substituent groups for the substituted alkyl group represented by $R_4$. A substituted alkyl group or a straight-chain or branched unsubstituted alkyl group having not less than 14 carbon atoms is preferred as the alkyl group from the viewpoint of solubility in organic solvents. A substituted alkyl group is more preferred, and a substituted alkyl group having not less than 14 carbon atoms in total is still more preferred. Preferred substituent groups for the substituted alkyl group include an alkoxy group, an aryloxy group, an alkylthio group, an arylthio group, an alkoxycarbonyl group, an aryloxycarbonyl group, a carbonamido group, a urethane group, a ureido group, an imido group, a sulfonamido group and a sulfonyl group. An alkoxycarbonyl group is particularly preferred. The aryl group represented by $R_5$ includes a substituted or unsubstituted aryl group such as phenyl group naphthyl group,etc. Examples of substituent groups for the substituted aryl group include those already described above in the definition of the substituent groups for the substituted alkyl group represented by $R_4$. The alkoxy group represented by $R_5$ is a substituted or unsubstituted straight-chain or branched alkyloxy group. Examples of substituent groups for the substituted alkyloxy group include those already described above in the definition of the substituent groups for the substituted alkyl group represented by $R_4$. The alkylamino group represented by $R_5$ include a substituted or unsubstituted straight-chain or branched alkylamino group. Examples of substituent groups for the substituted alkylamino group include those already described above in the definition of the substituent groups for the substituted alkyl group represented by $R_4$. The arylamino group represented by $R_5$ includes a substituted or unsubstituted arylamino group. Examples of the substituted arylamino group include those already described above in the definition of the substituent groups for the substituted alkyl group represented by $R_4$. Preferably, $R_5$ is an alkyl group, an aryl group, an alkoxy group or an alkylamino group form the viewpoint of solubility. More preferably, $R_5$ is an alkyl group, an aryl group or an alkoxy group from the viewpoint of easy synthesis. Particularly preferably, $R_5$ is an alkyl group.

A and B are each —CO— or —$SO_2$—; and n is 0 or 1. Preferably, A is —CO— because the maximum absorption wave form of dyes obtained by the coupling with the oxidants of developing agents is short wave.

$R_4$ and $R_5$ may be combined together to form a five-membered, a six-membered or seven-membered ring. Typical examples of the five-membered ring, the six-membered ring and the seven-membered ring include, but are not limited to, the following rings.

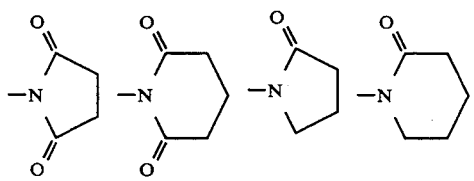

-continued

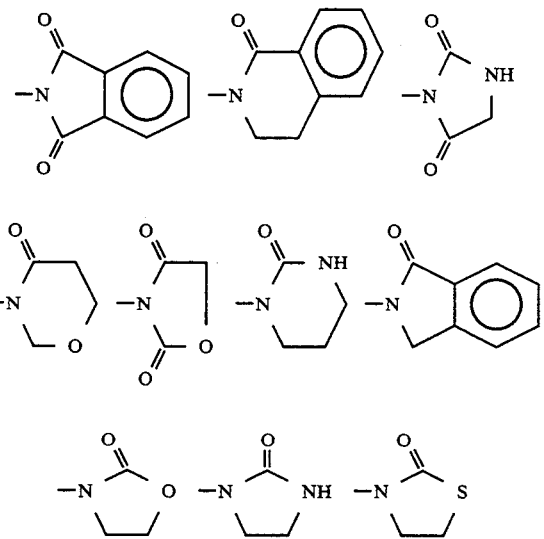

The five-membered ring, the six-membered ring and the seven-membered ring may have one or more substituent groups which can be attached to these rings. Examples of the substituent groups include those already described above in the definition of the substituent groups for $R_2$ and $R_3$.

The ring formed by $R_4$ and $R_5$ is preferably an imido ring or a lactam ring. However, the case where $R_4$ and $R_5$ are not combined together is more preferred. Preferably, n is 0. Most preferred is the case where n is 0 and $R_4$ is hydrogen atom.

Y is hydrogen atom, a halogen atom or an aryloxy group. In the couplers of the present invention, the halogen atom or the aryloxy group represented by Y is released by the coupling reaction with the oxidation product of the developing agents. Examples of the halogen atom include fluorine atom, chlorine atom and bromine atom. The aryloxy group include a substituted or unsubstituted aryloxy group. Examples of substituent groups for the substituted aryloxy group include those already described above in the definition of the substituent groups for the substituted alkyl group represented by $R_4$. Examples of the aryloxy group include phenoxy, 4-methylphenoxy, 4-tert-butylphenoxy, 4-methoxycarbonylphenoxy, 4-ethoxycarbonylphenoxy, 4-carboxyphenoxy, 4-cyanophenoxy and 2,4-dimethylphenxoy. Preferably, Y is a halogen atom or an aryloxy group. More preferably, Y is a halogen atom with chlorine atom being most preferred.

Examples of the typical magenta couplers of the present invention include, but are not limited to, the following compounds.

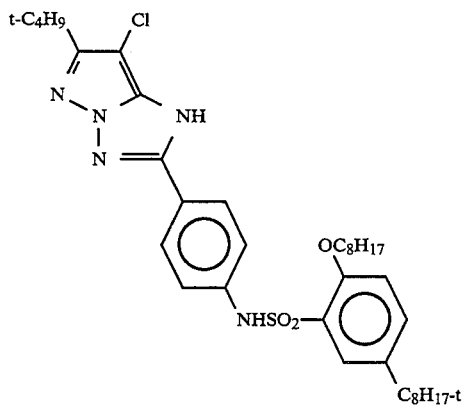 M-1
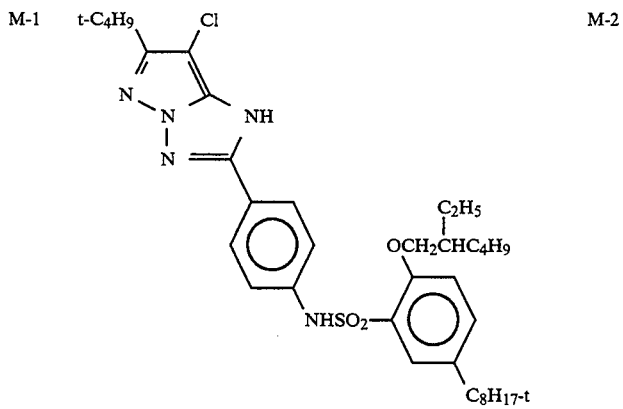 M-2
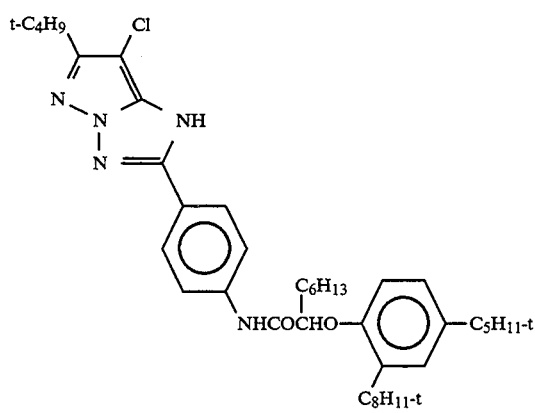 M-3
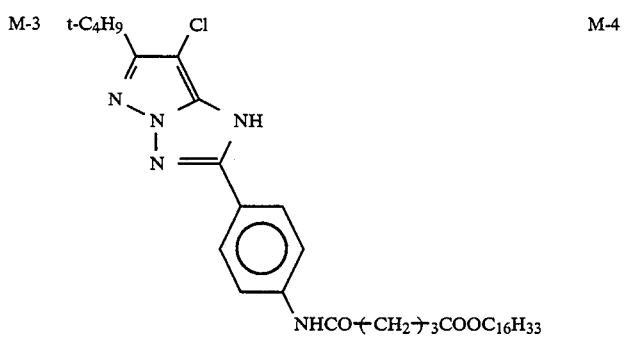 M-4
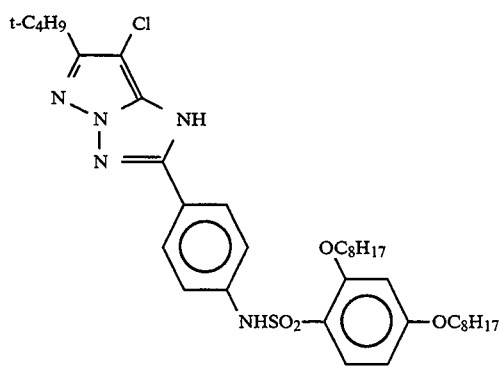 M-5
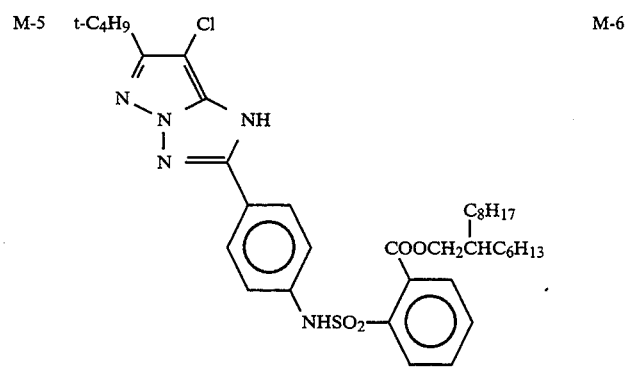 M-6
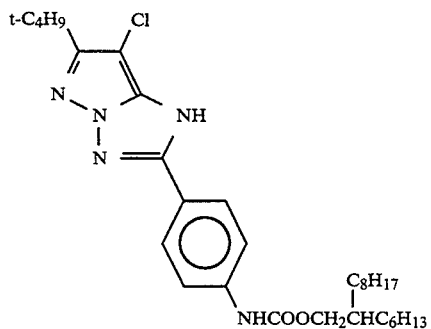 M-7
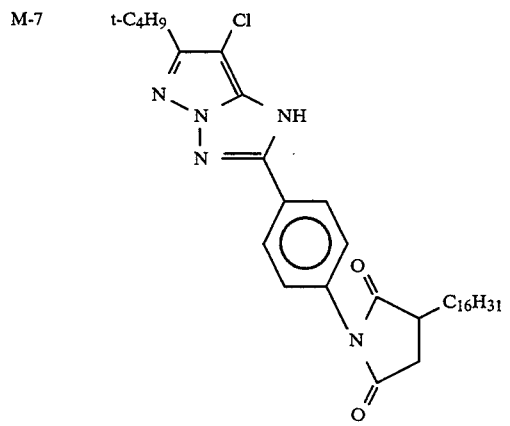 M-8

-continued
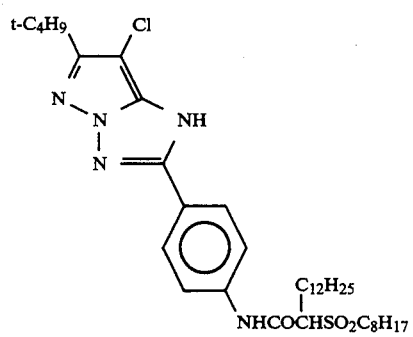
M-9
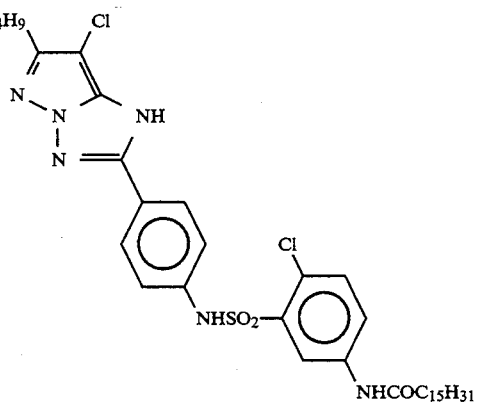
M-10
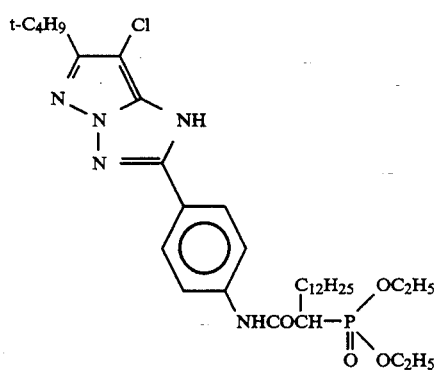
M-11
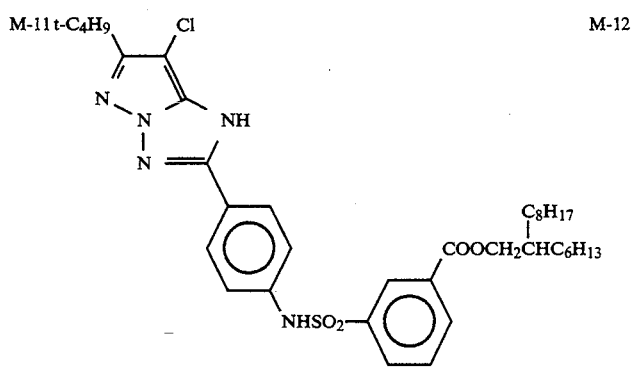
M-12
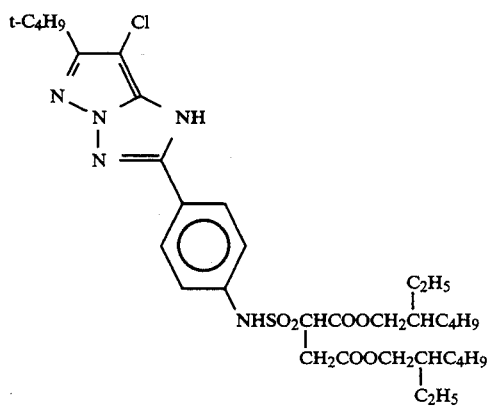
M-13
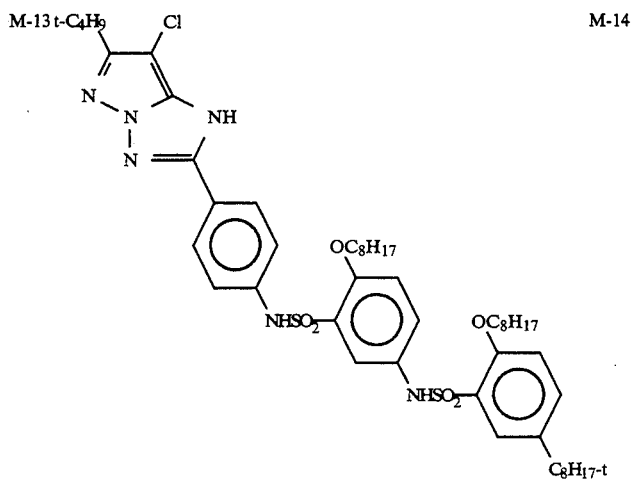
M-14
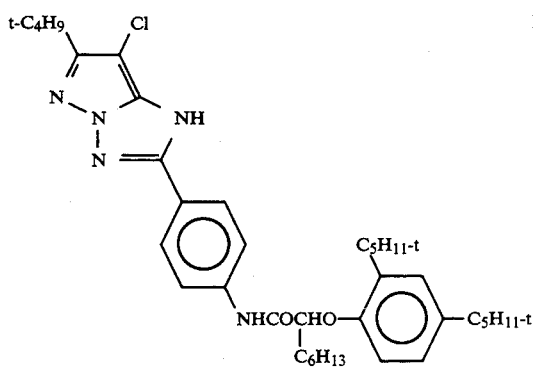
M-15
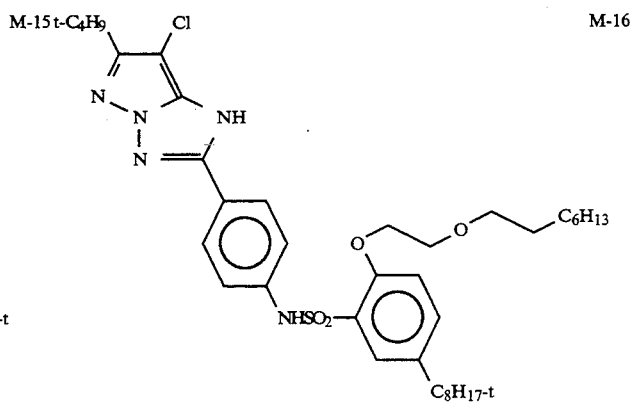
M-16

-continued
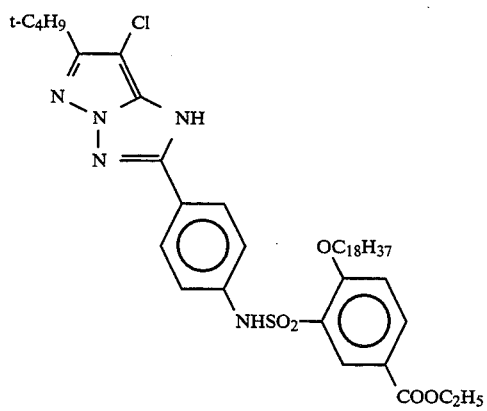 M-17
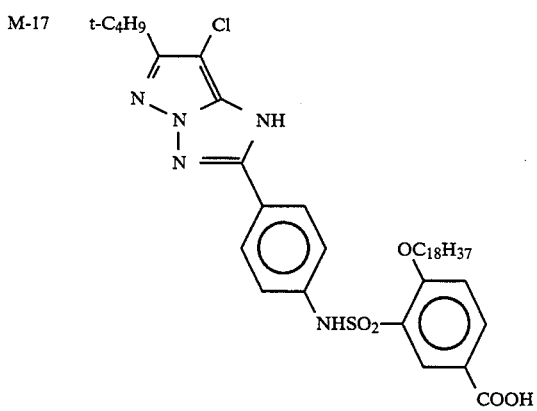 M-18
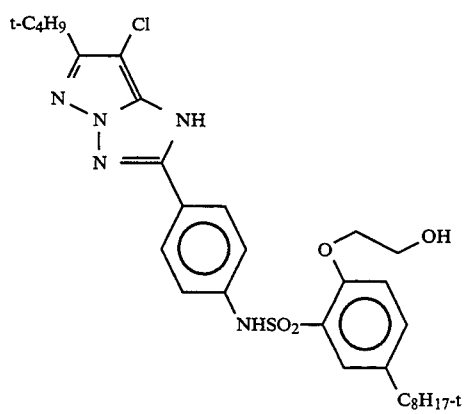 M-19
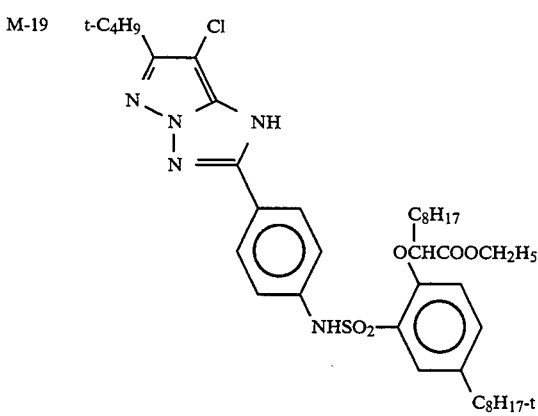 M-20
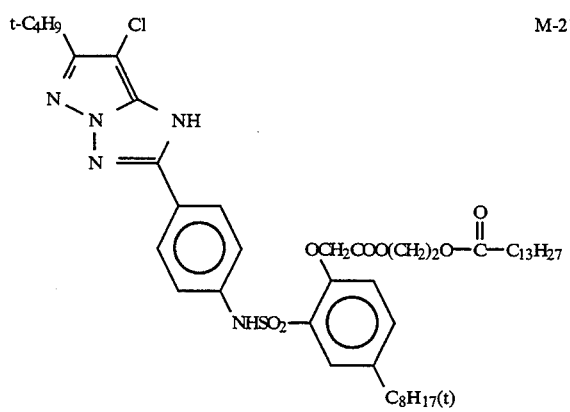 M-21
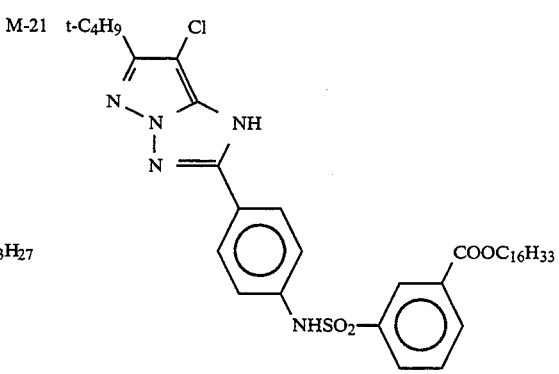 M-22
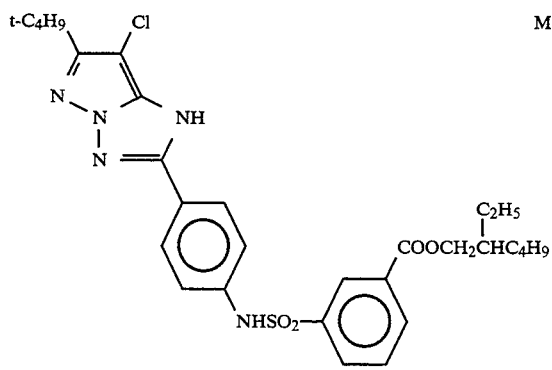 M-23
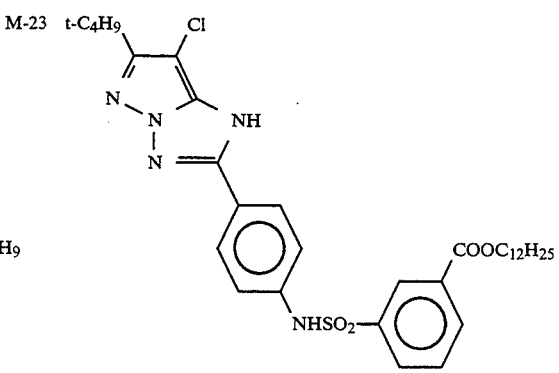 M-24

-continued
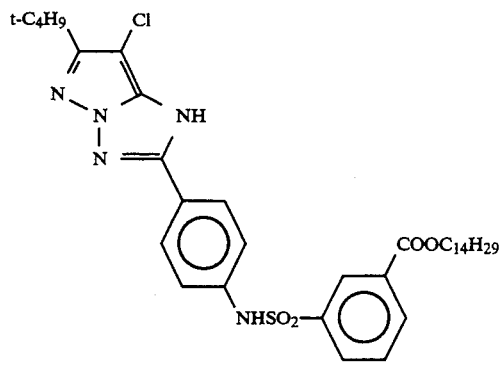
M-25
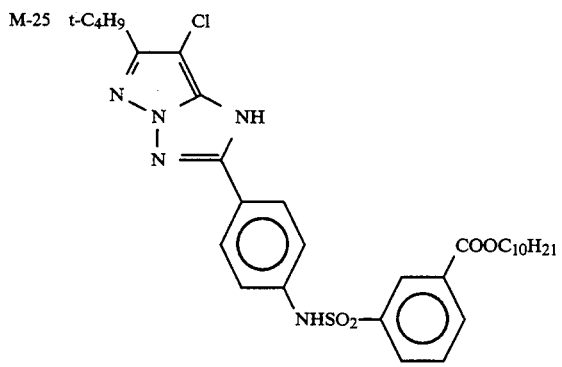
M-26
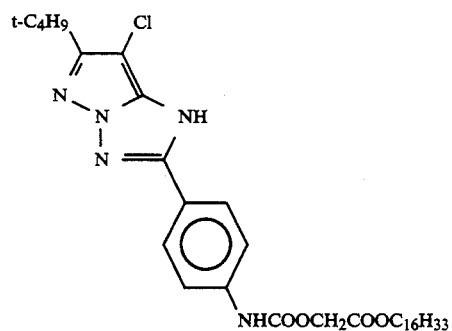
M-27
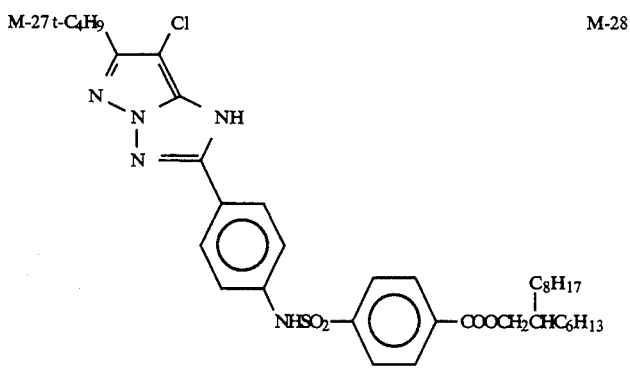
M-28
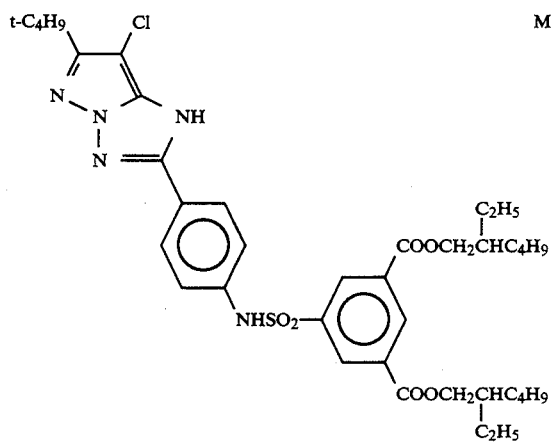
M-29
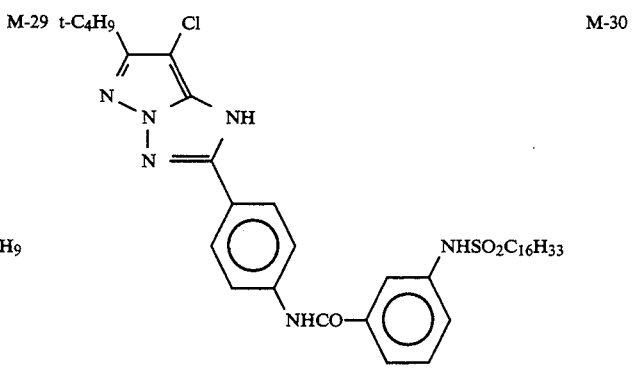
M-30
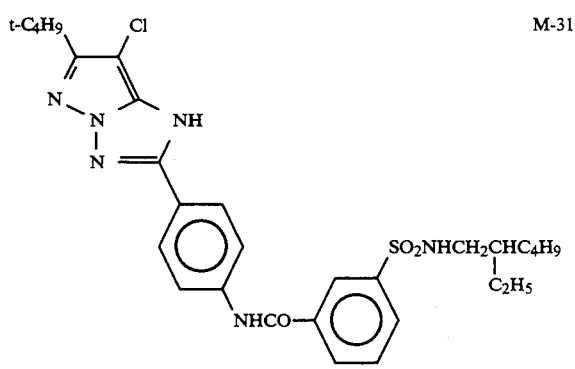
M-31

-continued
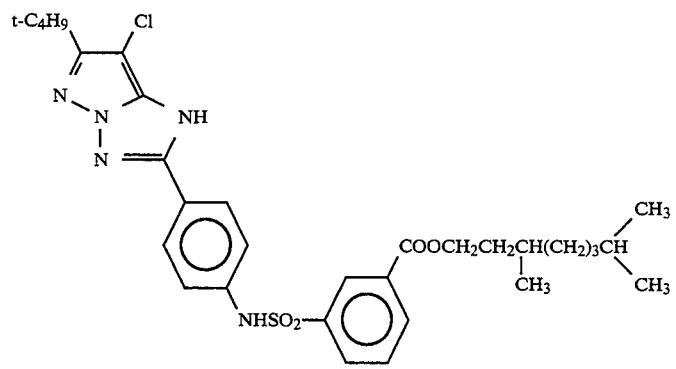
M-32
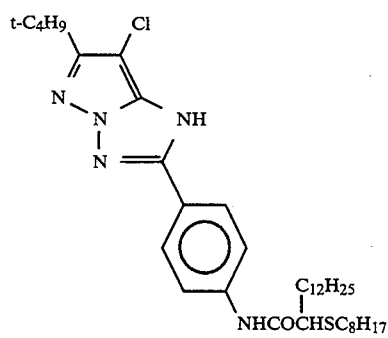
M-33
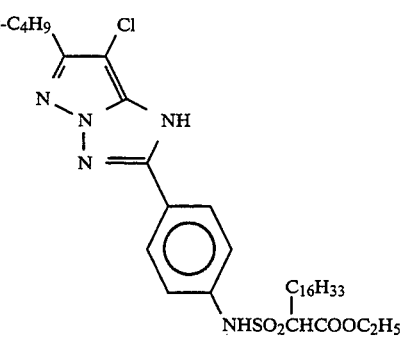
M-34
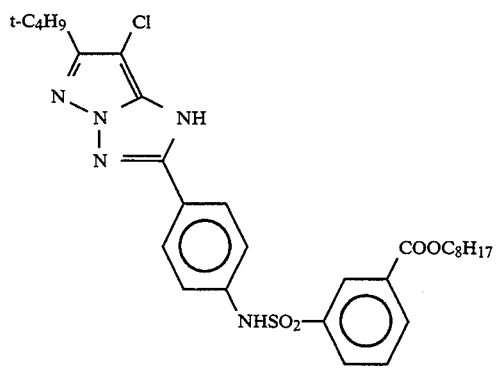
M-35
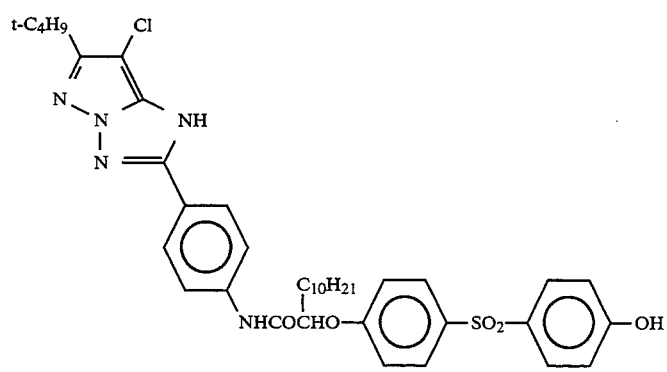
M-36

-continued
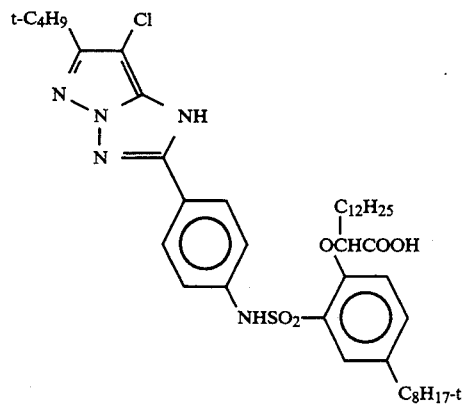
M-37
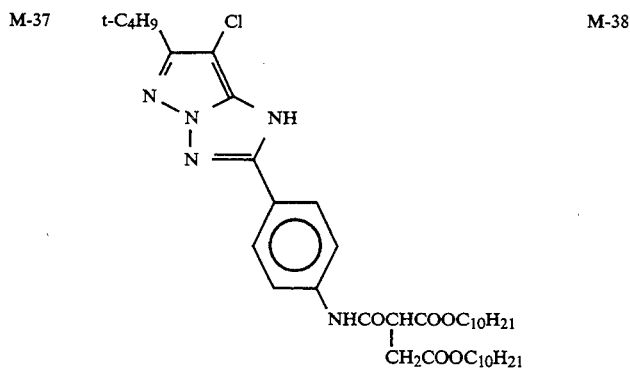
M-38
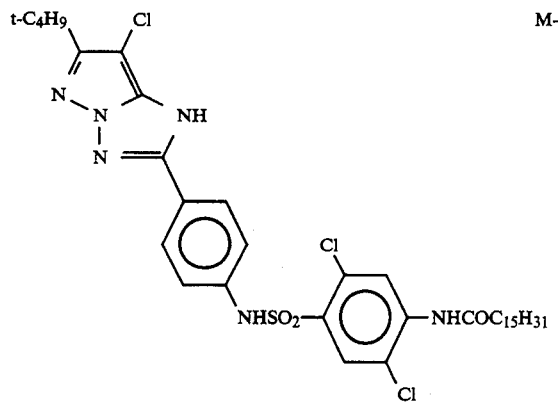
M-39
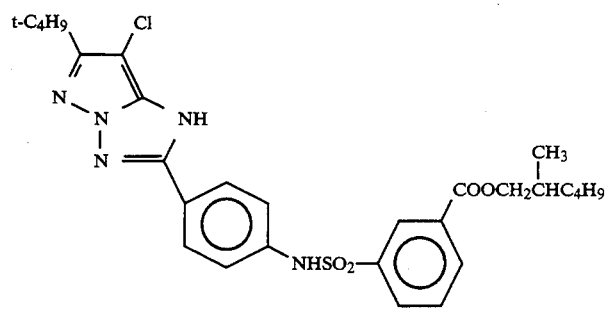
M-40
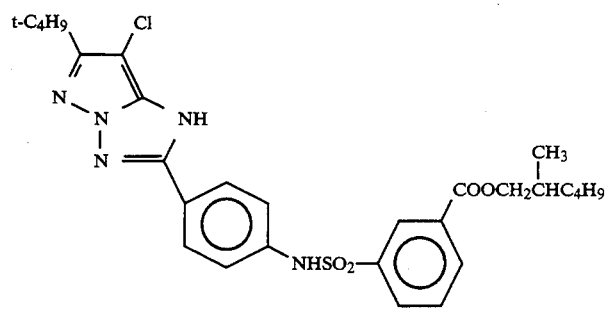
M-41
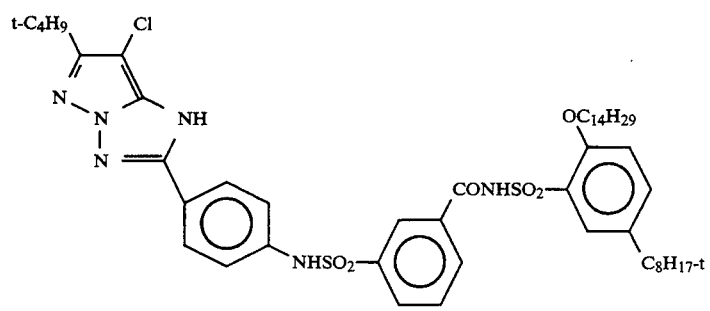
M-42

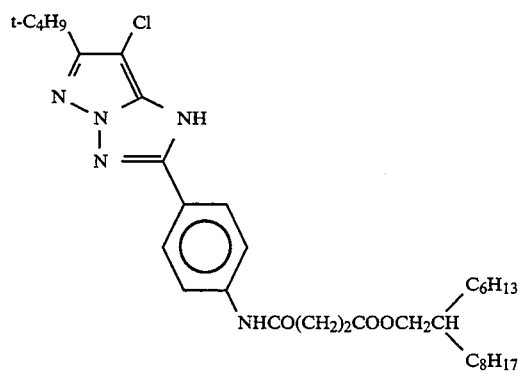
M-43
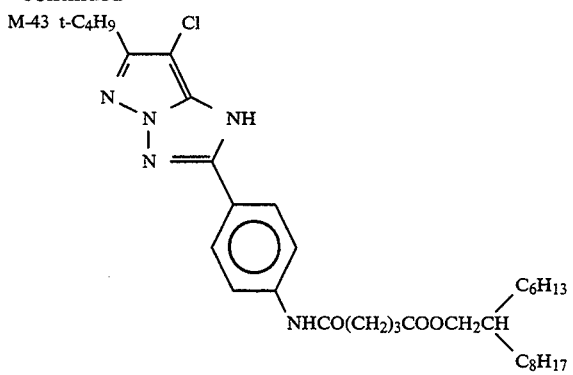
M-44
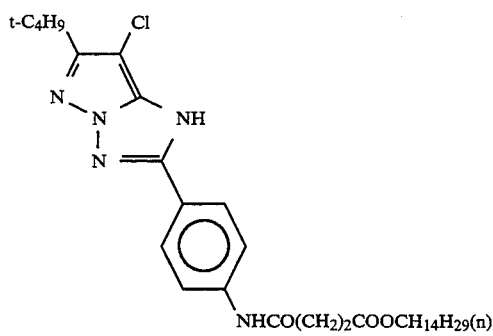
M-45
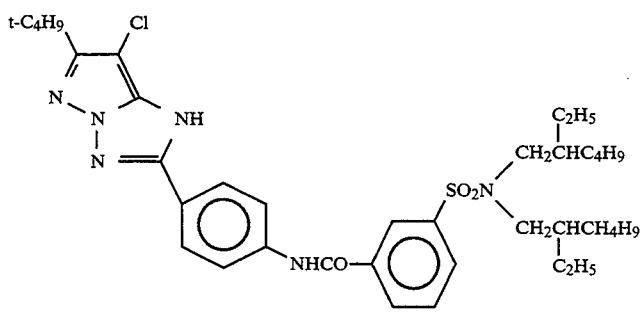
M-46
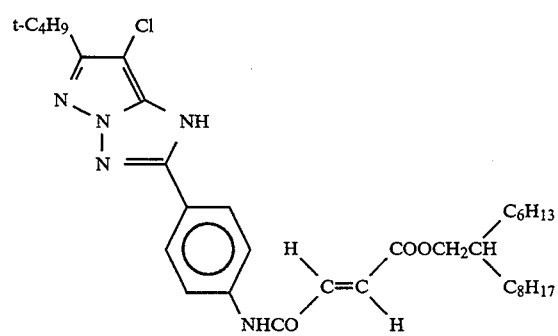
M-47
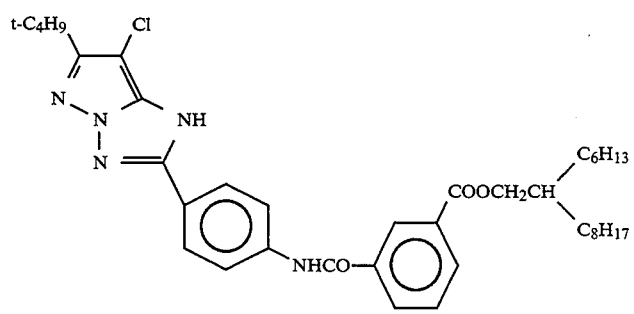
M-48

-continued
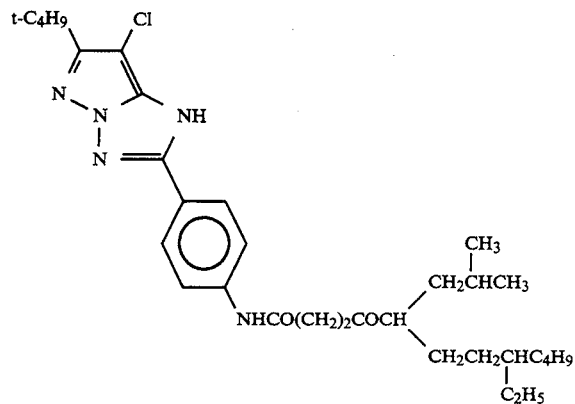
M-49
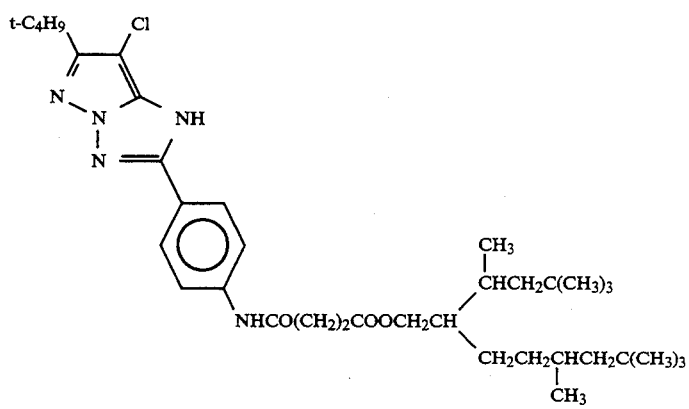
M-50
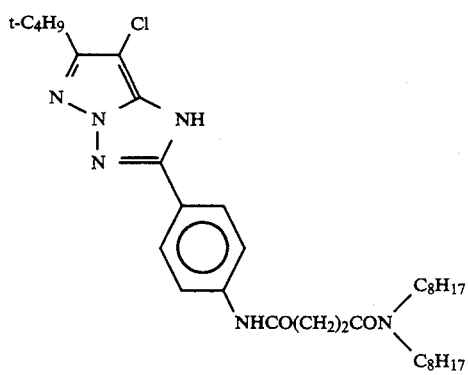
M-51
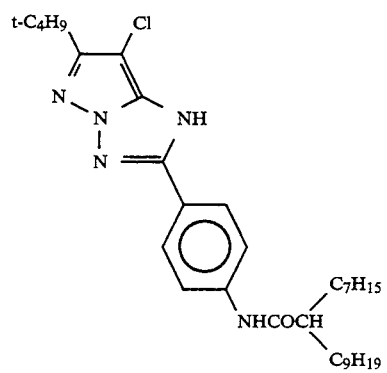
M-52
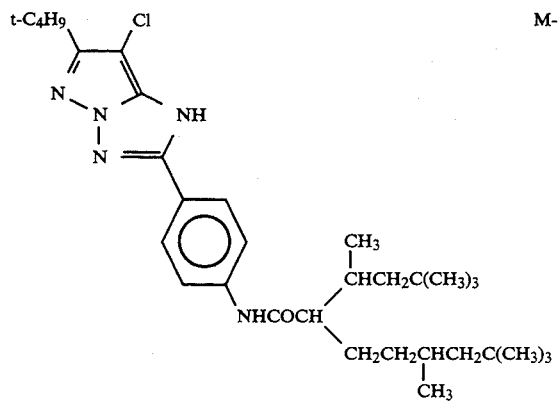
M-53
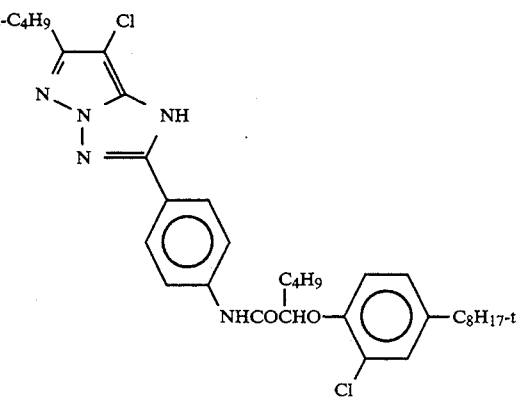
M-54

-continued
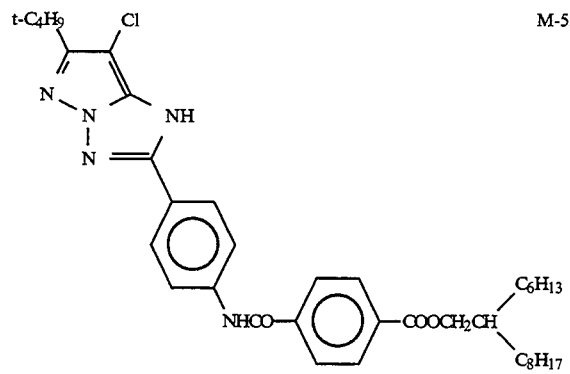 M-55
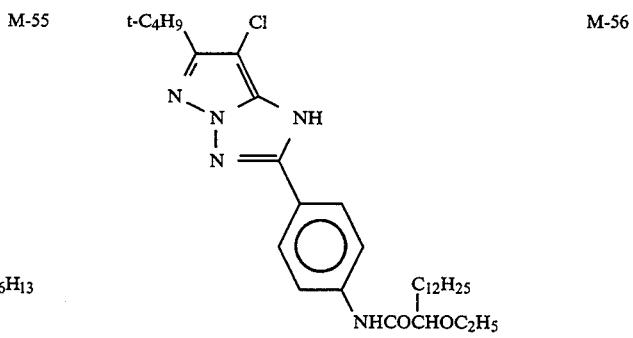 M-56
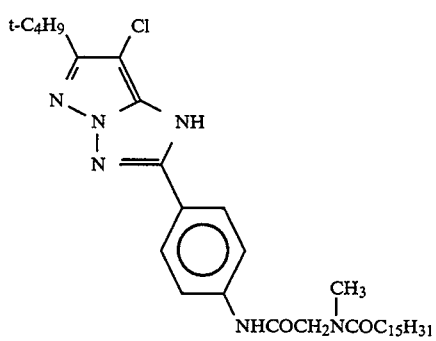 M-57
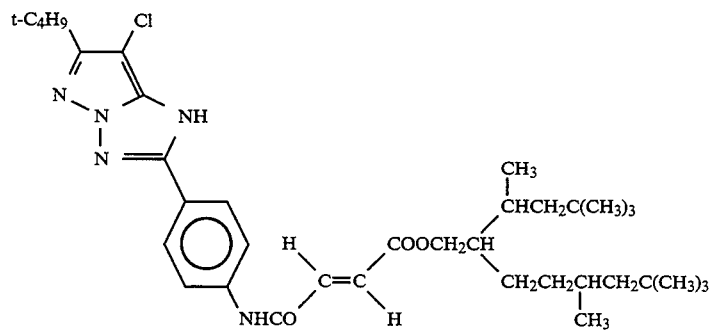 M-58
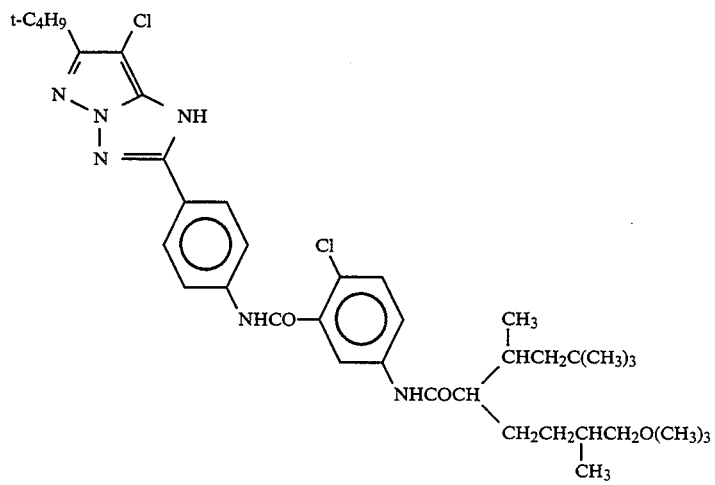 M-59

-continued
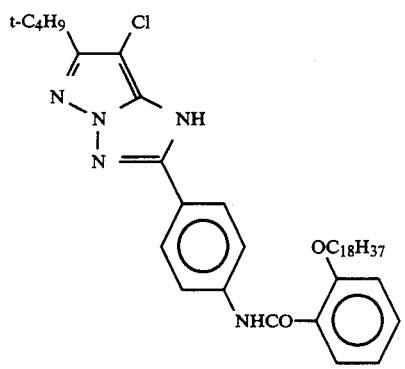
M-60
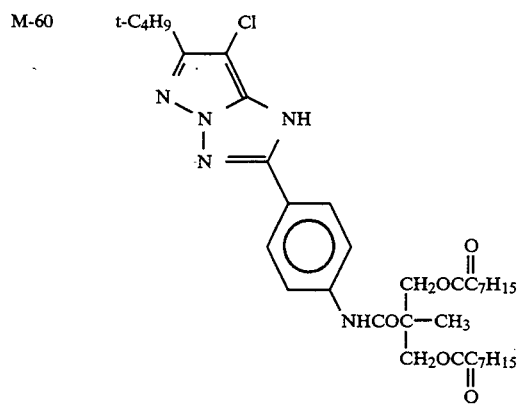
M-61
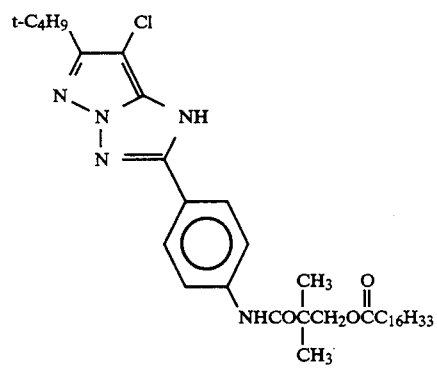
M-62
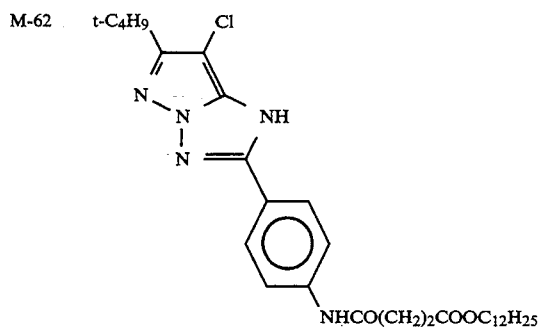
M-63
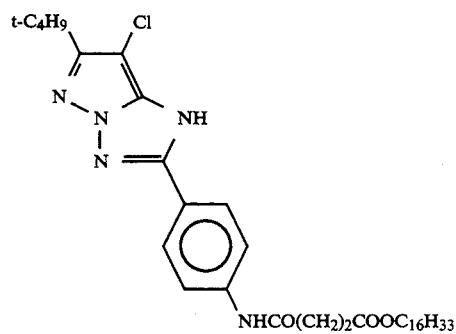
M-64
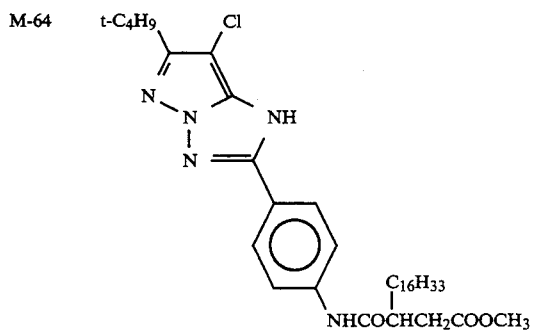
M-65
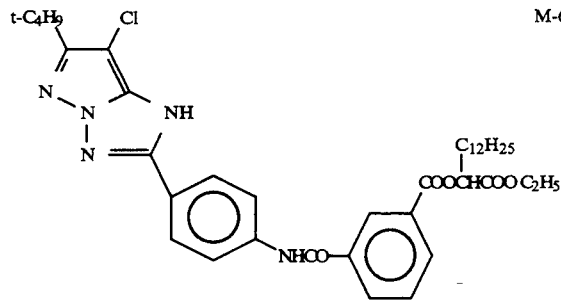
M-66
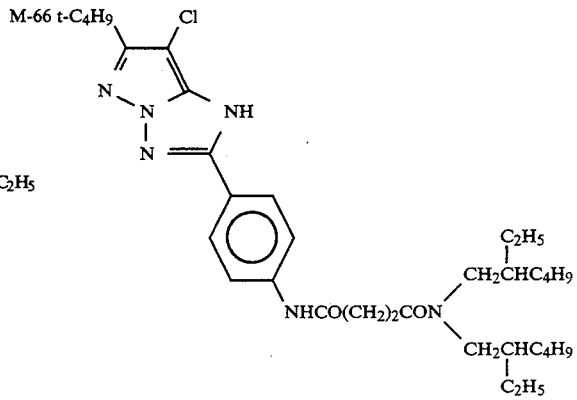
M-67

-continued
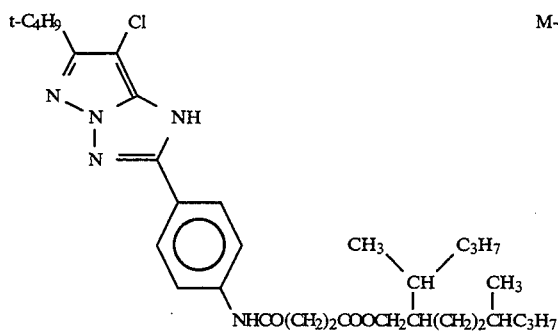
M-68
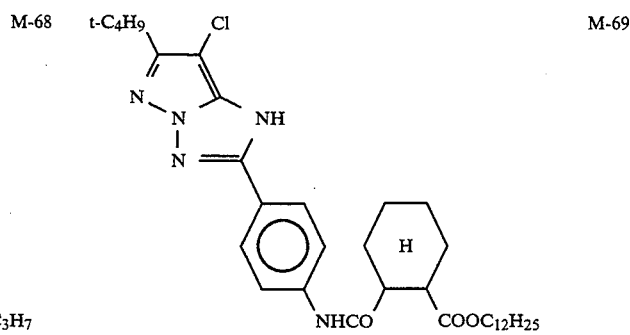
M-69
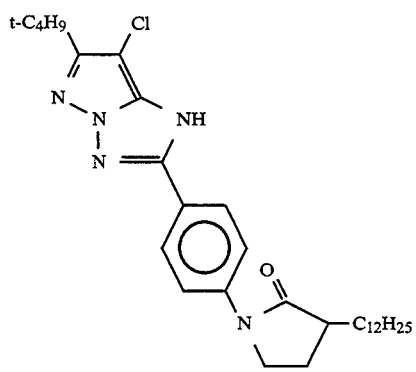
M-70
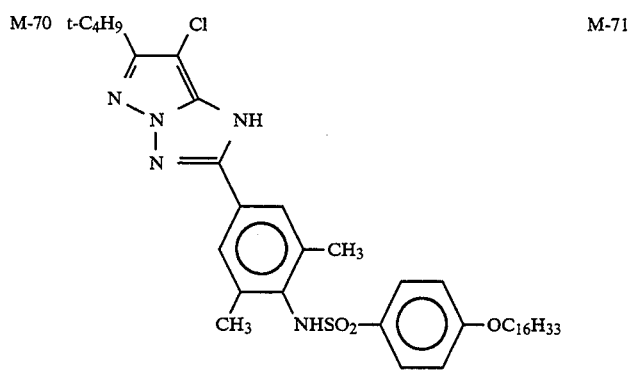
M-71
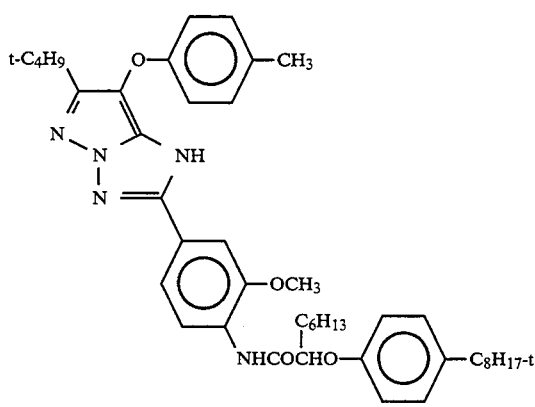
M-72
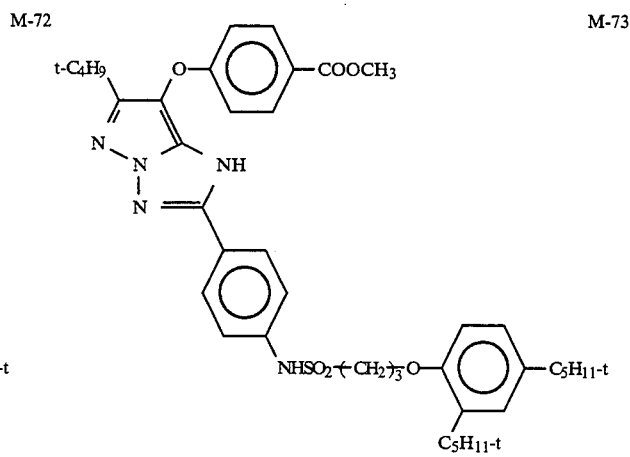
M-73
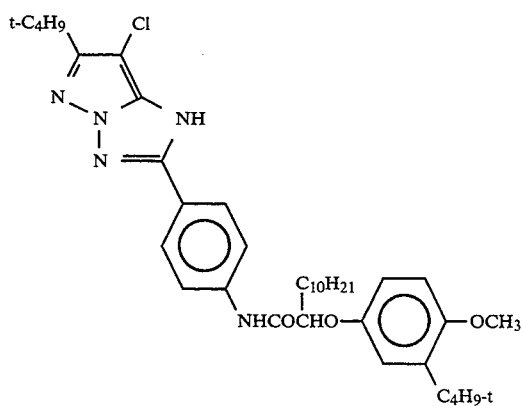
M-74
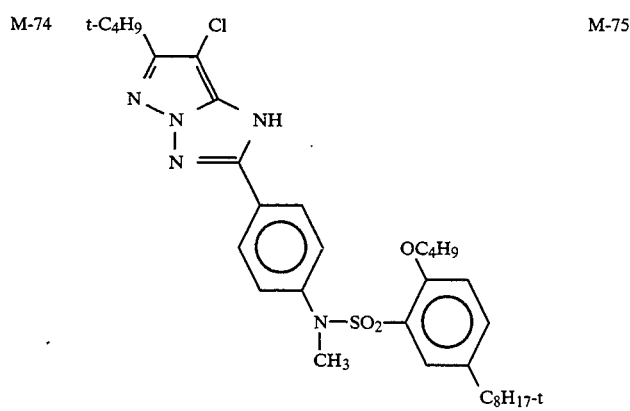
M-75

-continued
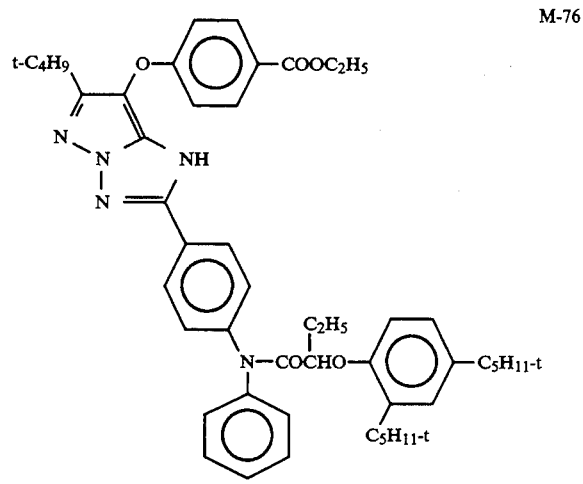
M-76
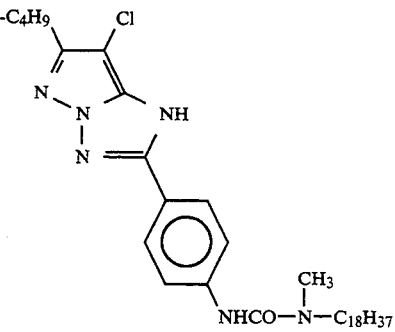
M-77
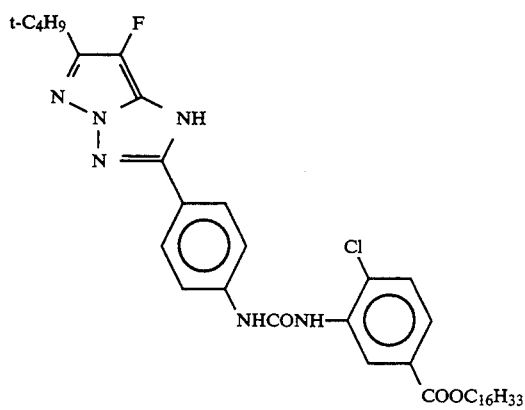
M-78
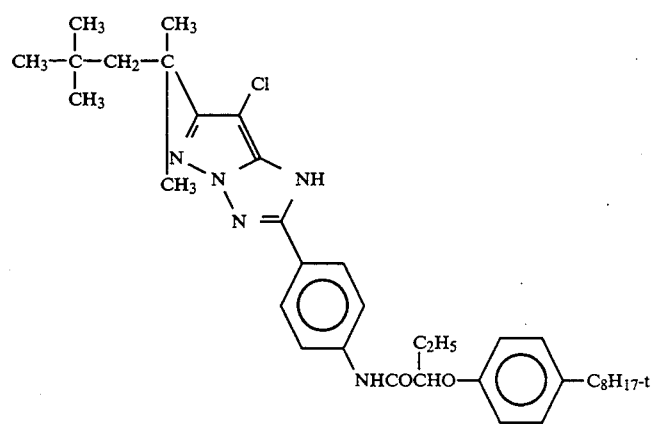
M-79

M-80 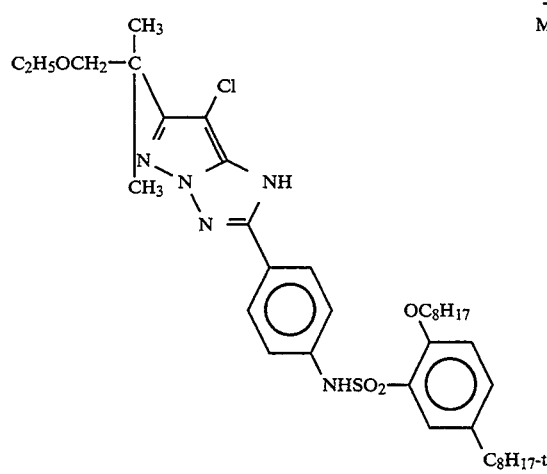
M-81 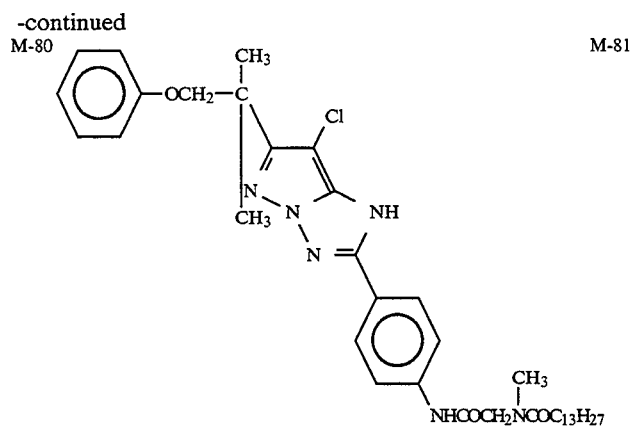
M-82 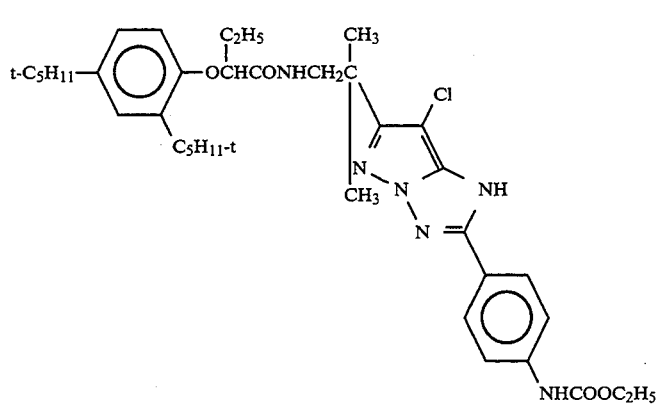
M-83 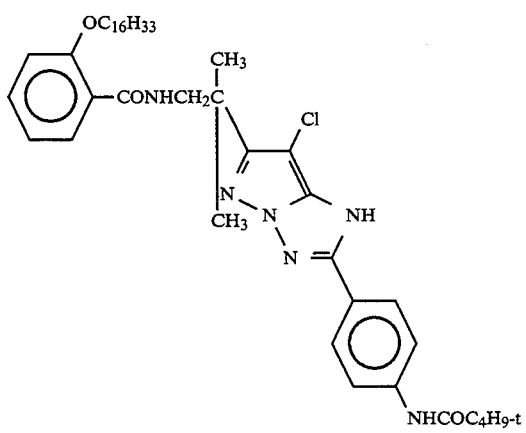
M-84 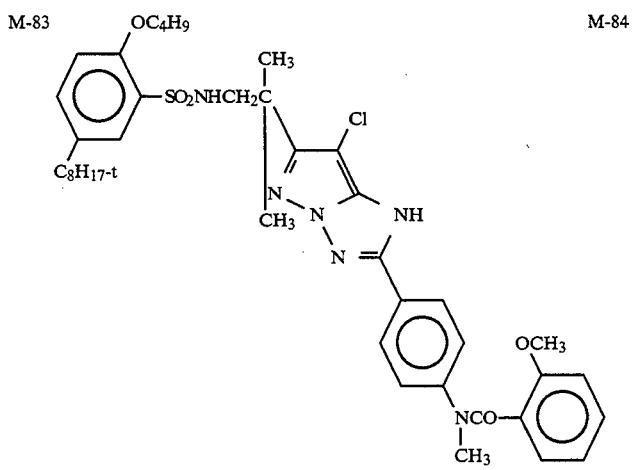
M-85 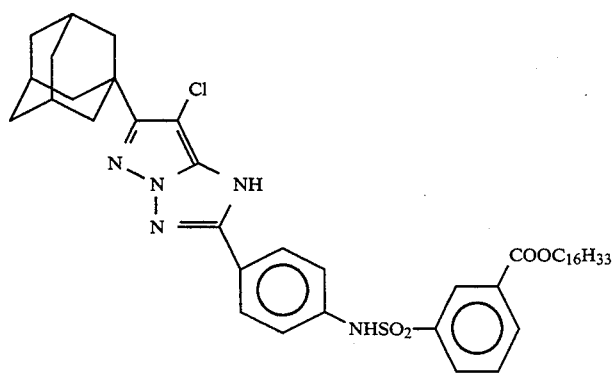

-continued
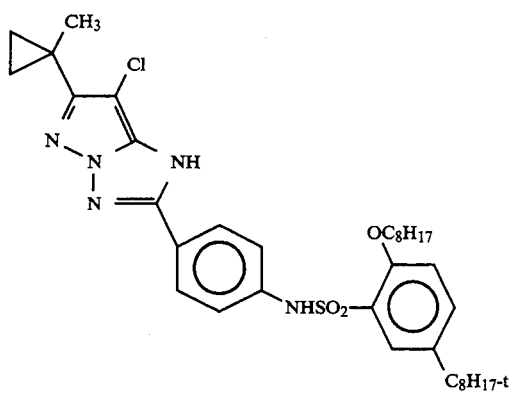
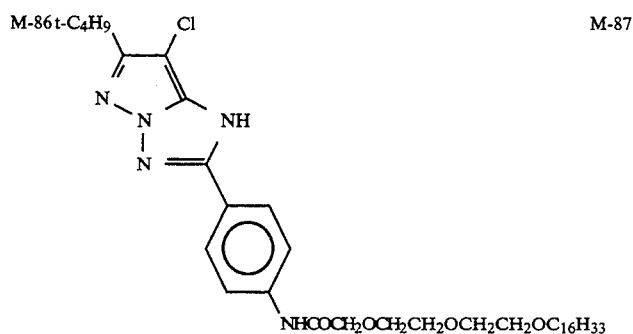
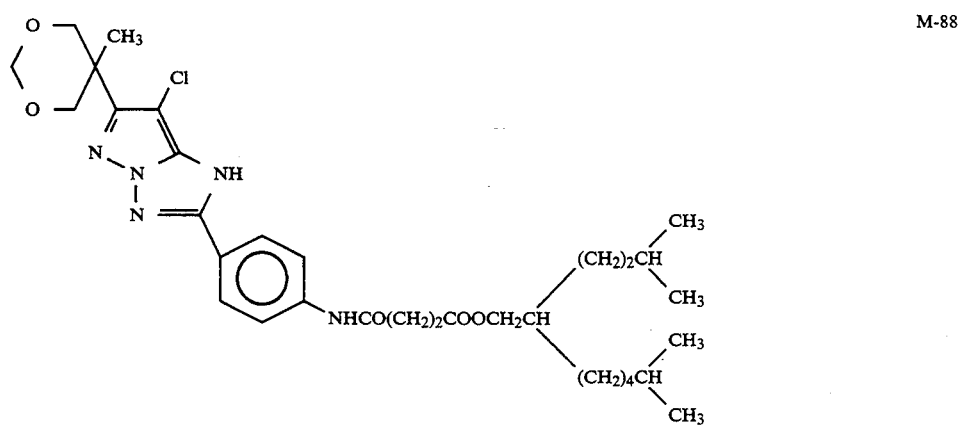
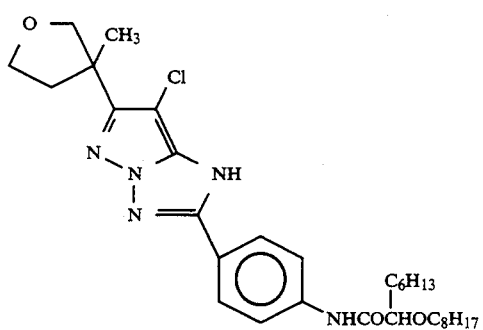
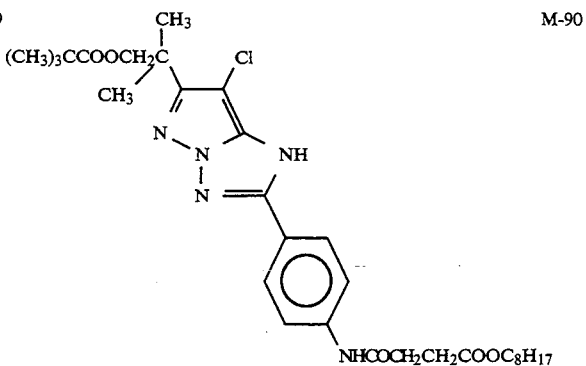
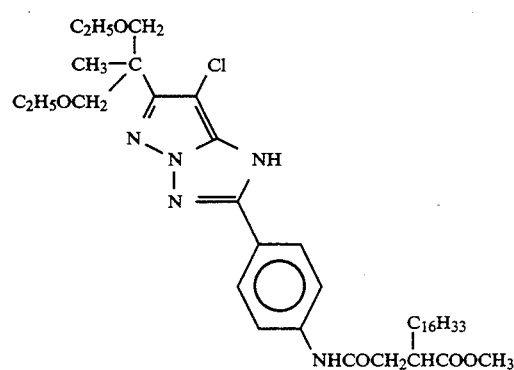

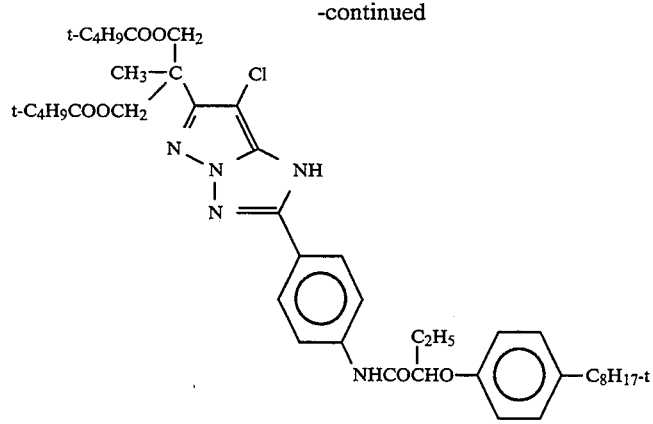

M-92

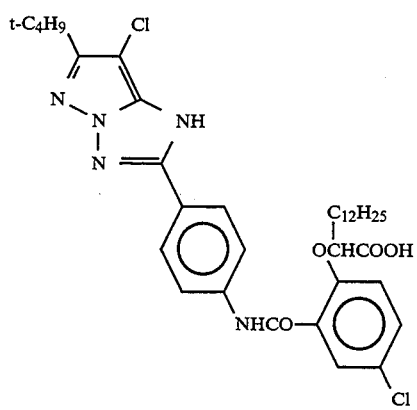

M-93

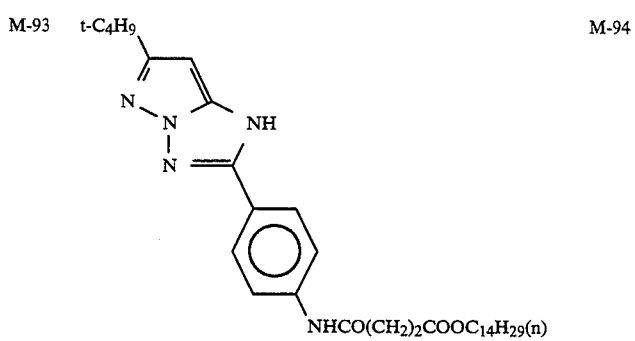

M-94

General synthesis methods of the couplers of the present invention will be illustrated below.

The 1H-pyrazolo[1,5-b][1,2,4]triazole couplers of the present invention can be synthesized according to the methods described in JP-A-60-197688 and JP-A-3-184980.

Namely, the couplers of the present invention can be synthesized according to the following synthesis scheme A and synthesis scheme B.

Synthesis scheme A

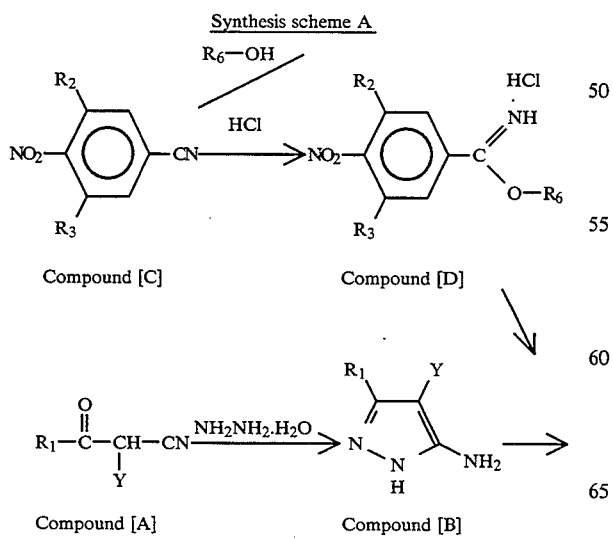

-continued
Synthesis scheme A

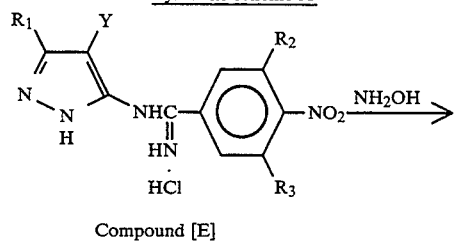

Compound [E]

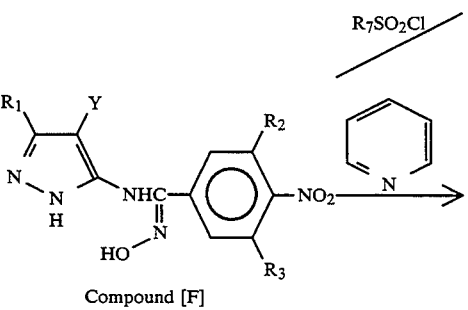

Compound [F]

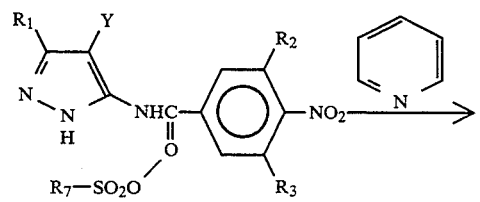

Compound [G]

-continued
Synthesis scheme A

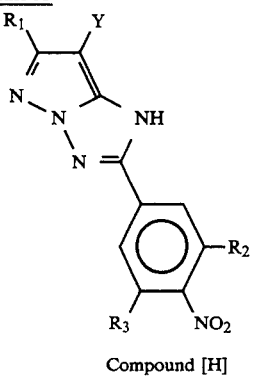

Compound [H]

Synthesis scheme B

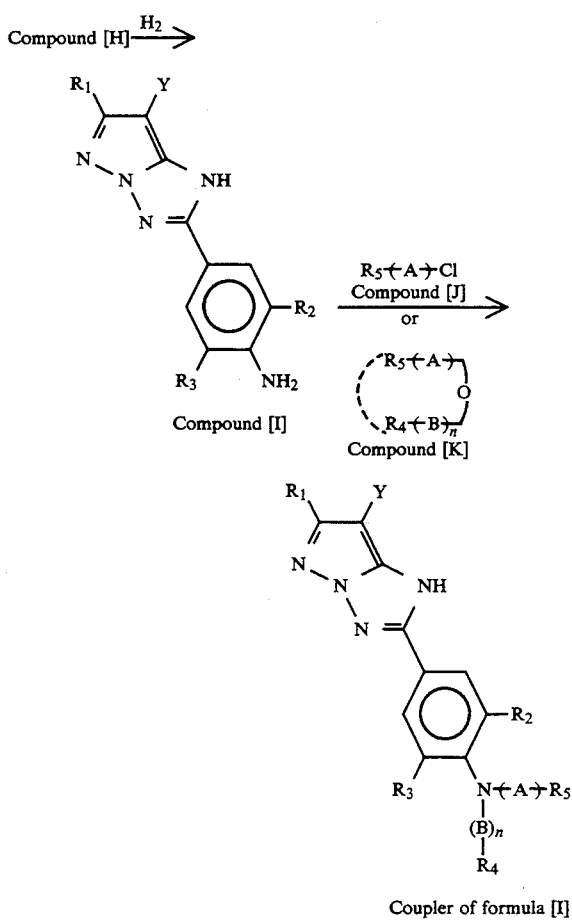

Coupler of formula [I]

wherein Y represents hydrogen atom, a halogen atom or an aryloxy group; $R_6$ represents a straight-chain or branched alkyl group having 1 to 10 carbon atoms or phenyl group; and $R_7$ represents a straight-chain or branched alkyl group having 1 to 4 carbon atoms or a substituted or unsubstituted aryl group.

A β-keto-nitrile compound (compound [A]) is reacted with hydrazine to obtain an aminopyrazole (compound [B]). Separately, a benzonitrile (compound [C]) is reacted with an alcohol in the presence of hydrogen chloride to obtain an imidic acid ester (compound [D]). The imidic acid ester (compound [D]) is reacted with the above aminopyrazole (compound [B]) to obtain an amidine (compound [E]). The amidine is then reacted with hydroxylamine to obtain an amidoxime (compound [F]). The amidoxime (compound [F]) is then reacted with an alkyl- or arylsulfonyl chloride in the presence of a base to obtain a sulfonate (compound [G]). The sulfonate (compound [G]) is intramolecularly cyclized in the presence of a base to obtain a 1H-pyrazolo[1,5-b]-[1,2,4]triazole (compound [H]). The nitro group of the 1H-pyrazolo[1,5]b][1,2,4]triazole (compound [H]) is reduced to obtain an amine (compound [I]). The reduction of nitro group can be carried out by various reduction methods such as catalytic reduction with hydrogen gas in the presence of a palladium-carbon catalyst, reduction with ammonium formate in the presence of a palladium-carbon catalyst, or neutral reduction with reduced iron and ammonium chloride. The amine (compound [I]) is reacted with an acid chloride (compound [J]) or acid anhydride (compound [K]) or a lactone (compound [K]), whereby the coupler of the present invention can be easily the obtained. When compound [J] is used, (B)$_n$- $R_4$ in the coupler (I) represents a hydrogen atom (n=0, $R_4$=a hydrogen atom).

When a compound where Y is a halogen atom is to be produced, the releasable group Y can be easily introduced into the compound by reacting a compound, where the position-7 of 1H-pyrazolo[1,5-b][1,2,4]triazole skeleton is hydrogen, with an appropriate halogenating compound. Examples of the halogenating agent include chlorine gas, sulfuryl chloride, N-chlorosuccinimide, bromine gas and N-bromosuccinimide. If desired, an intermediate, 3-amino-5-t-butyl-pyrazole is reacted with the halogenating agent to synthesize a 3-amino-5-t-butyl-4-halogenopyrazole, and the pyrazolotriazole skeleton can be then synthesized according to the above synthesis scheme.

When a coupler where Y is an aryloxy group is to be synthesized, an acyl-2-aryloxyacetonitrile is prepared according to the method described in JP-A-2-300195, and the desired compound can be synthesized according to the above synthesis method. Alternatively, a 1H-pyrazolo[1,5-b][1,2,4]triazole compound where the position-7 is halogenated is reacted with a phenol in the presence of a base, whereby the desired compound can be synthesized.

Synthesis method is illustrated by reference to the following synthesis examples.

Synthesis scheme [C]

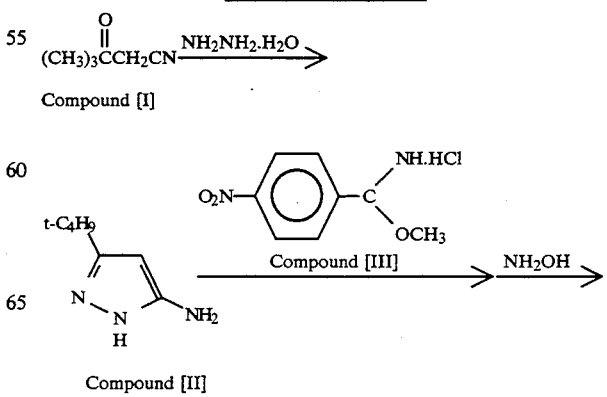

-continued
Synthesis scheme [C]

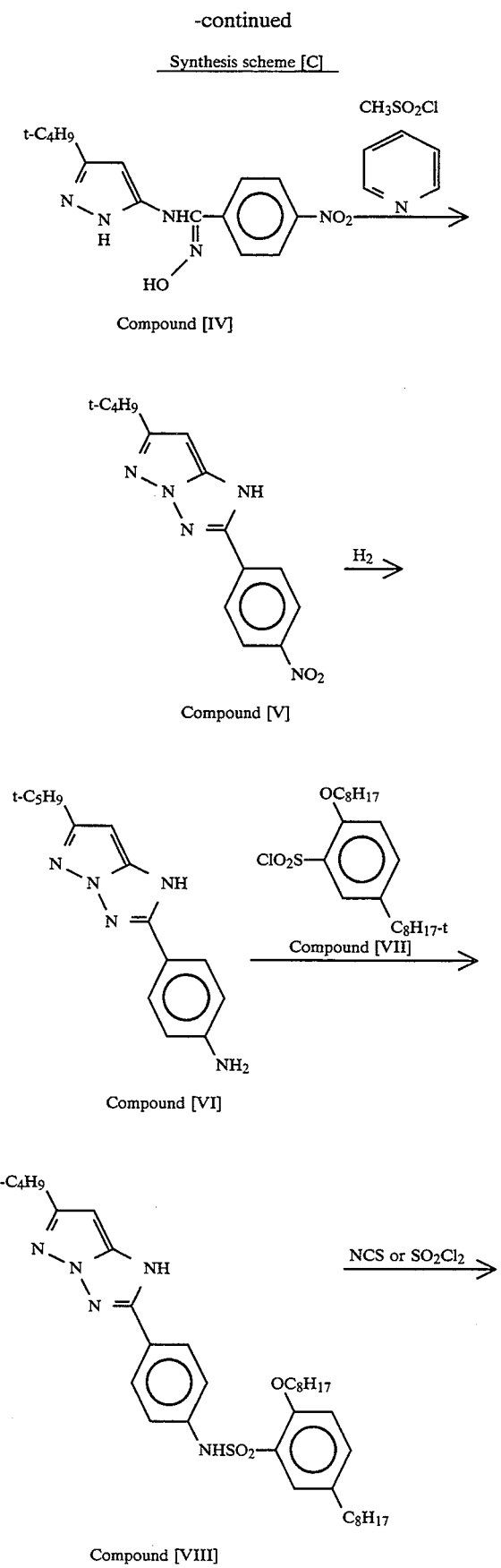

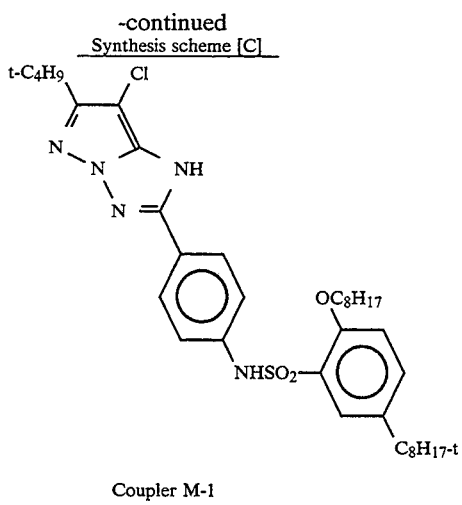

Coupler M-1

SYNTHESIS EXAMPLE 1

Synthesis of coupler M-1

To 600 g of pivaloyl acetonitrile (compound I), there was added 800 ml of isopropanol. The mixture was heated with stirring, and 288 g of hydrazine hydrate was added dropwise thereto. The mixture was heated with stirring for 3 hours. After completion of the reaction, 400 ml of isopropanol was distilled off under reduced pressure. To the residue, there were added 2000 ml of ethyl acetate and saturated brine. The mixture was stirred and then left to stand for a while. The aqueous layer was removed, and the ethyl acetate layer was washed with saturated brine twice. The ethyl acetate solution was then dried over anhydrous magnesium sulfate, and then concentrated under reduced pressure. Subsequently, 2000 ml of n-hexane was added to the residue to precipitate a crystal. The crystal was recovered by filtration and dried. There was obtained 643 g (96.2%) of 3-amino-5-t-butylpyrazole (compound II). Melting point: 74.0° to 75.0° C.

To 250 g of 3-amino-5-t-butylpyrazole prepared above, there was added 2800 ml of acetonitrile. The mixture was stirred at room temperature. To the resulting solution, there was added 390 g of methyl 4-nitrophenylimidate hydrochloride (compound III). The mixture was stirred at room temperature for 7 hours. Subsequently, a methanol solution of hydroxylamine (prepared from 150 g of hydroxylamine hydrochloride and 430 ml of a 28 wt % methanol solution of sodium methylate) was added thereto, and the mixture was stirred for 8 hours. After completion of the reaction, 8000 ml of water was added to the resulting solution. The precipitated crystal was recovered by filtration and dried. There was obtained 421.7 g (77.2%) of an amidoxime (compound IV). Melting point: 175° to 177° C.

To 364 g of the amidoxime (compound IV), there was added 900 ml of dimethylacetamide. The mixture was cooled to 10° C. and then stirred. To the mixture, there was added 144.3 g of methanesulfonic acid chloride. Further, 233 ml of pyridine was added thereto. The mixture was stirred at room temperature for 2 hours, and 2600 ml of methanol was added thereto. The resulting mixture was stirred with heating at 55° C. for 5 hours. After completion of the reaction, the reaction mixture was cooled to room temperature, and 1800 ml of water was added thereto to precipitate a crystal. The crystal was recovered by filtration and dried. There was obtained 249 g (72.8%) of a cyclized product (compound V). Melting point: 259° to 260° C.

To 209 g of reduced iron and 20 g of ammonium chloride, there were added 120 ml of water and 1200 ml of isopropanol. The mixture was heated with stirring. To the resulting solution, there was added portionwise 202 g of the compound V prepared above. After completion of the addition, the mixture was stirred with heating for one hour. The reaction mixture (solution) was filtered while it was still hot to remove insoluble matters. The filtrate was concentrated under reduced pressure. To the residue, there was added 3000 ml of water was added to thereby precipitate a crystal. The crystal was recovered by filtration and dried. There was obtained 167.9 g (92.9%) of an amine (compound VI). Melting point: 263° to 265° C.

To 58.0 g of the amine (compound VI) prepared above, there was added 180 ml of dimethylacetamide. The mixture was stirred at room temperature. To the resulting solution, there was added dropwise 100 g of 2-octyl-oxy-5-t-octylbenzenesulfonic acid chloride (compound VII), and further 22 ml of pyridine was added dropwise thereto. After completion of the addition, the mixture was continuously stirred at room temperature for 5 hours. Subsequently, ethyl acetate and water were added thereto to conduct extraction. The ethyl acetate solution was washed with saturated brine, dried over anhydrous magnesium sulfate and stirred at room temperature. To the ethyl acetate solution, there was then added portionwise 30.7 g of N-chlorosuccinimide. After completion of the addition, the mixture was stirred at room temperature for one hour and washed with 800 ml of water. The ethyl acetate solution was concentrated to dryness under reduced pressure. The residue was recrystallized from a mixed solvent of ethyl acetate and n-hexane. There was obtained 112.3 g (72.3%) of the coupler M-1. Melting point: 127° to 129° C.

Proton NMR, δ (ppm) (multiplicity, integral value) (CDCl$_3$) 10.73 (br, 1H), 7.78 (d, 1H), 7.65 (d, 2H), 7.44 (dd, 1H), 7.07 (d, 2H), 6.89 (d, 1H), 4.14 (t, 2H), 2.05–1.78 (m, 2H), 1.65–1.15 (m, 18H), 1.43 (s, 9H), 0.88 (t, 3H), 0.49 (s, 9H)

Synthesis scheme [D]

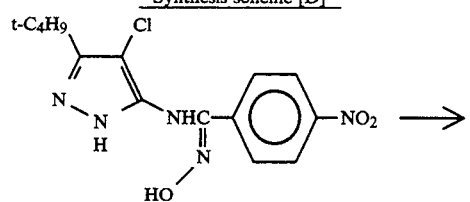

Compound [II]

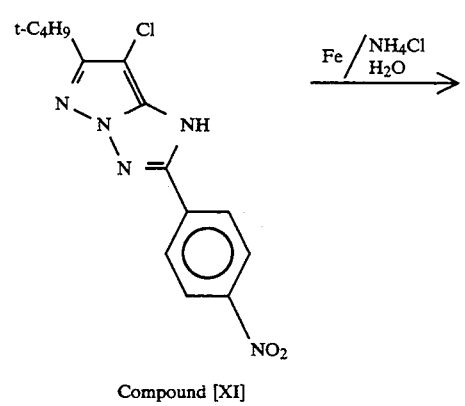

Compound [IX]

-continued
Synthesis scheme [D]

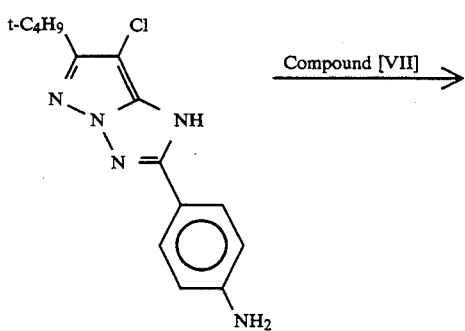

Compound [X]

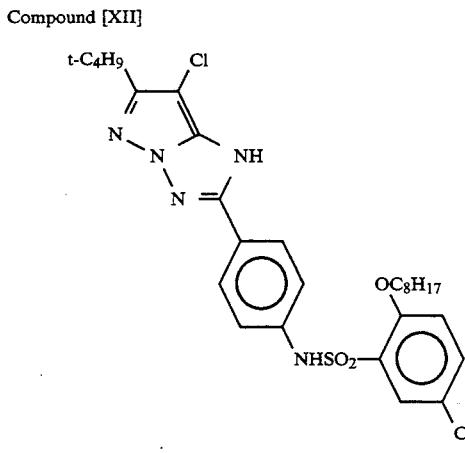

Compound [XI]

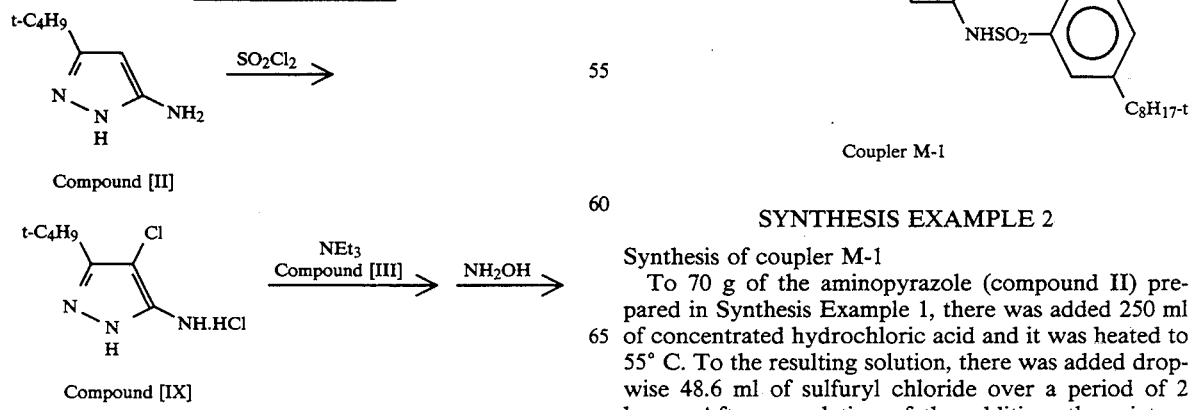

Compound [XII]

Coupler M-1

SYNTHESIS EXAMPLE 2

Synthesis of coupler M-1

To 70 g of the aminopyrazole (compound II) prepared in Synthesis Example 1, there was added 250 ml of concentrated hydrochloric acid and it was heated to 55° C. To the resulting solution, there was added dropwise 48.6 ml of sulfuryl chloride over a period of 2 hours. After completion of the addition, the mixture was stirred for one hour and then concentrated under reduced pressure. To the residue, there was added 300 ml of toluene, and the mixture was further concentrated under reduced pressure. Subsequently, 250 ml of ethyl acetate was added to the residue to precipitate a crystal. The crystal was recovered by filtration and dried. There was obtained 100.2 g (94.8%) of a chlorinated product (compound IX). Melting point: 160° to 167° C.

To 112 g of the chlorinated product (compound IX), there was added 700 ml of acetonitrile. The mixture was stirred at room temperature and then neutralized with 75 ml of triethylamine. To the resulting solution, there was added 116 g of methyl 4-nitrophenylimidate hydrochloride (compound III). The mixture was stirred at room temperature for 8 hours. Subsequently, a methanol solution of hydroxylamine (prepared from 46.3 g of hydroxylamine hydrochloride and 134 ml of a 28 wt % of methanol solution of sodium methylate) was added thereto. The mixture was stirred for 8 hours. After completion of the reaction, 2600 ml of water was added thereto to precipitate a crystal. The crystal was recovered by filtration and dried. There was obtained 123 g (68.3%) of an amidoxime (compound X). Melting point: 158° to 162° C.

To 20.0 g of the amidoxime (compound X) prepared above, there was added 60 ml of dimethylacetamide. The mixture was stirred at room temperature, and 11.9 g of p-toluenesulfonic acid chloride was added thereto. Further, 5.3 ml of pyridine was added dropwise thereto, and the mixture was stirred at room temperature for 3 hours. To the resulting solution, there were added 150 ml of methanol and 4.8 ml of pyridine. The mixture was heated with stirring for 3 hours. After completion of the reaction, the reaction mixture was poured into water to precipitate a gummy product, the gummy product was separated from the mixture. Acetonitrile was added to the gummy product. The mixture was stirred to crystallize the product. The crystal was recovered by filtration and dried. There was obtained 11.8 g (62.3%) of a cyclized product (compound XI). Melting point: 249° to 252° C.

To 18 g of reduced iron and 1.7 g of ammonium chloride, there were added 15 ml of water and 150 ml of isopropanol. The mixture was heated with stirring. To the resulting solution, there was added portionwise 20.0 g of the cyclized product (compound XI) prepared above. After completion of the addition, the mixture was stirred with heating for 30 minutes. After completion of the reaction, the reaction mixture was filtered while it was still hot to remove insoluble matters. Subsequently, 1000 ml of water was added to the filtrate to precipitate a crystal. The crystal was recovered by filtration and dried. There was obtained 15.0 g (82.8%) of an amine (compound XII). Melting point: 261° to 263° C.

To 8.69 g of the amine (compound XII) prepared above there was added 25ml of dimethylacetamide. The mixture was stirred at room temperature, and 15.0 g of 2-octyloxy-5-tert-octylbenzenesulfonic acid chloride (compound VII) was added dropwise thereto. Further, 2.9 ml of pyridine was added dropwise thereto. After completion of dropwise addition, the mixture was stirred for 5 hours and extracted with ethyl acetate. The ethyl acetate solution was washed with saturated brine and concentrated under reduced pressure. The residue was recrystallized from a mixed solvent of ethyl acetate and n-hexane. There was obtained 17.5 g (87.1%) of coupler M-1. Melting point: 127°–129° C. The melting point was the same as that of the product obtained in Synthesis Example 1. Further, NMR spectrum data were identical with those of the product obtained in Synthesis Example 1.

SYNTHESIS EXAMPLE 3

Synthesis of coupler M-43

Succinic anhydride (145.2 g) and 2-octyloctal (291 g) were stirred with heating at 120° to 130° C. for 3 hours and then cooled to 80° C. Subsequently, 300 ml of water was added thereto. The mixture was stirred for additional one hour and then cooled to room temperature. The reaction mixture was extracted with 500 ml of ethyl acetate. The ethyl acetate solution was washed with water twice and then concentrated under reduced pressure sure. There was obtained 409.8 g (99.7%) of 3-(2-octyloctyloxycarbonyl)propionic acid as an oily product.

To 409.8 g of 3-(2-octyloctyloxycarbonyl)propionic acid obtained above, there was added 500 ml of toluene. The mixture was stirred with heating at 70° to 80° C. To the resulting solution, there was added dropwise 132 ml of thionyl chloride. The mixture was heated with stirring for 3 hours. After completion of the reaction, toluene and an excess amount of thionyl chloride were distilled off under reduced pressure to obtain 429.5 g (99.5%) of 3-(2-octyloctyloxycarbonyl)propionic acid chloride as an oily product.

To 25.5 g of the amine (compound VI) prepared in Synthesis Example 1, there were added 50 ml of dimethylacetamide and 50 ml of ethyl acetate. The mixture was stirred at room temperature. To the resulting solution, there was added dropwise 40 g of 3-(2-octyloctyloxycarbonyl)propionic acid chloride prepared above. Further, 10 ml of pyridine was added dropwise thereto. After completion of dropwise addition, the reaction was carried out at room temperature for 2 hours, and 100 ml of ethyl acetate was added thereto. Further, 14.0 g of N-chlorosuccinimide was added portionwise thereto. After completion of the addition, the mixture was stirred at room temperature for 2 hours. After completion of the reaction, the ethyl acetate solution was washed with warm water (40° to 60° C.) three times and then concentrated under reduced pressure to precipitate a crystal. The crystal was recrystallized from a mixed solvent of ethyl acetate and acetonitrile (1:1) to obtain 55.7 g (90.7%) of coupler M-43. Melting point and NMR data are shown in Table 9.

SYNTHESIS EXAMPLE 4

Synthesis of coupler M-45

Succinic anhydride (24.2 g) and tetradecanol (42.9 g) were molten by heating them at 120° to 130° C. and stirred for 3 hours. After completion of the reaction, the reaction mixture was cooled to 80° C., and 50 ml of water was added thereto. The mixture was stirred for one additional hour. The reaction mixture was cooled to room temperature and extracted with 200 ml of ethyl acetate. The ethyl acetate solution was washed with 200 ml of water three times and concentrated to dryness under reduced pressure. There was obtained 60.9 g (96.8%) of 3-tetradecyloxycarbonylpropionic acid. Melting point: 48° to 49° C.

To 25.5 g of the amine (compound VI) obtained in Synthesis Example 1, 33.0 g of 3-tetradecyloxycarbonylpropionic acid prepared above and 19.5 ml of pyridine, there was added 250 ml of ethyl acetate. The mixture was stirred at room temperature. Subsequently, 5.5 g of phosphorus trichloride was added dropwise thereto, and the mixture was stirred at room temperature for 2 hours and then at 60° to 77° C for one hour. There was synthesized a compound where the position-7 of coupler M-45 was a hydrogen atom. The reaction mixture was cooled to room temperature, and 16.2 ml of sulfuryl chloride was added dropwise thereto. The mixture was stirred for 2 hours. There was synthesized a chlorinated compound where the position-7 of coupler M-45 was chlorinated. After completion of the reaction, the mixture was extracted with 200 ml of hot water (60° to 70° C). The ethyl acetate solution was washed with an aqueous solution of sodium bicarbonate. Subsequently, 25.0 g of sodium bicarbonate, 20 g of sodium sulfite, 200 ml of water and 50 ml of methanol were added thereto. The mixture was stirred at 40° to 50° C. for 2 hours. After completion of the reaction, the aqueous layer was removed, and the ethyl acetate solution was washed with hot water (60° to 70° C.) twice. The ethyl acetate solution was concentrated under reduced pressure to precipitate a crystal. The crystal was recrystallized from a mixed solvent of ethyl acetate and acetonitrile (5:1) to obtain 49.5 (84.4%) of coupler M-45. Melting point and NMR data are shown in Table 9.

SYNTHESIS EXAMPLE 5 TO 66

Couplers M-2 to M-41 and M-43 to M-51 were synthesized in the same manner as described in Synthesis Example 1. Further, couplers M-52 to M-68 were synthesized in the same manner as described in Synthesis Example 2, 3 or 4.

The melting points and NMR spectrums of these couplers are shown in Tables 1 to 14.

TABLES 1 TO 14

| Coupler No. | Melting point | Proton NMR δ (ppm) (multiplicity, integral value) |
|---|---|---|
| M-2 | 126–131 | (DMSO) 13.33 (s, 1H), 10.32 (s, 1H), 7.90–7.73 (m, 3H), 7.55 (dd, 1H), 7.23 (d, 2H), 7.09 (d, 1H), 3.95 (d, 2H), 1.90–1.12 (m, 17H), 1.49 (s, 9H), 0.98–0.75 (m, 6H), 0.59 (s, 9H) |
| M-3 | 170–173 | (DMSO) 13.43 (s, 1H), 10.50 (s, 1H), 7.96 (d, 2H), 7.81 (d, 2H), 7.19–6.98 (m, 2H), 6.71 (d, 1H), 4.87 (t, 1H), 2.09–1.05 (m, 26H), 1.40 (s, 9H), 0.87 (t, 3H), 0.61 (t, 6H) |
| M-4 | 184–186 | (DMSO) 13.40 (s, 1H), 10.22 (s, 1H), 7.90 (d, 2H), 7.78 (d, 2H), 4.00 (t, 2H), 2.55–2.25 (m, 4H), 1.96–1.75 (m, 2H), 1.65–1.00 (m, 28H), 1.40 (s, 9H), 0.85 (t, 3H) |
| M-5 | 155–156 | (CDCl$_3$) 13.33 (s, 1H), 10.25 (s, 1H), 7.90–7.70 (m, 3H), 7.21 (d, 2H), 6.67–6.53 (m, 2H), 4.08 (t, 2H), 3.49 (t, 2H), 1.68 (br, 4H), 1.50–1.08 (m, 20H), 1.38 (s, 9H), 0.98–0.75 (m, 6H) |
| M-6 | 152–153 | (DMSO) 13.35 (brs, 1H), 10.80 (brs, 1H), 8.05–7.04 (m, 4H), 7.84 (d, 2H), 7.25 (d, 2H), 4.20 (d, 2H), 1.85–1.60 (m, 1H), 1.39 (s, 9H), 1.45–1.00 (m, 24H), 0.81 (t, 6H) |
| M-7 | 157–160 | (CDCl$_3$) 11.65 (br, 1H), 7.76 (d, 2H), 7.38 (d, 2H), 7.12 (s, 1H), 4.12 (d, 2H), 1.65 (dr, 1H), 1.49 (s, 9H), 1.28 (brs, 24H), 0.86 (t, 6H) |
| M-8 | 174–175 | (CDCl$_3$) 11.39 (br, 1H), 7.88 (d, 2H), 7.31 (d, 2H), 5.75–5.52 (m, 1H), 4.98–5.23 (ip, 1H), 3.27–2.92 (m, 2H), 2.80–2.58 2H), 2.57–2.37 (m, 1H), 2.16–1.88 (m, 2H), 1.48 (s, 9H), 1.40–1.05 (br, 22H), 0.88 (t, 3H) |
| M-9 | 187–188 | (CDCl$_3$) 11.35 (br, 1H), 9.04 (s, 1H), 7.65 (d, 2H), 7.47 (d, 2H), 4.05–3.92 (m, 1H), 3.3 5–3.00 (m, 2H), 2.32–1.75 (m, 4H), 1.57–1.04 (m, 30H), 1.45 (s, 9H), 0.87 (t, 6H) |
| M-10 | 190–192 | (CDCl$_3$) 12.66 (s, 1H), 10.12 (s, 1H), 9.73 (s, 1H), 8.20 (d, 1H), 8.11 (d.d, 1H), 7.84 (d, 2H), 7.37 (d.d, 1H), 7.25 (d, 2H), 2.36 (t, 2H), 1.79–1.55 (m, 2H), 1.46 (s, 9H), 1.50–1.05 (m, 24H), 0.87(t, 3H) |
| M-11 | 169–170 | (DMSO) 13.40 (s, 1H), 10.40 (s, 1H), 7.95 (d, 2H), 7.79 (d, 2H), 4.20–4.02 (m, 4H), 3.25–2.95 (m, 1H), 2.10–1.05 (m, 28H), 1.40 (s, 9H), 0.82 (t, 3H) |
| M-12 | 103–105 | (CDCl$_3$) 11.54 (br, 1H), 8.51 (s, 1H), 8.25–7.95 (m, 3H), 7.69–7.44 3H), 7.09 (d, 2H), 4.25 (d, 2H), 1.85–1.65 (br, 1H), 1.47 (s, 9H), 1.55–1-05 (m, 24H), 0.84 (t, 6H) |
| M-13 | 110–111 | (CDCl$_3$) 11.62 (br, 1H), 7.63 (d, 2H), 7.50 (s, 1H), 7.25 (d, 2H), 4.37–4.23 (m, 1H), 4.20–3.90 (m, 4H), 3.34–3.00 (m, 2H), 1.58 (br, 2H), 1.53 (s, 9H), 1.45–1.10 (m, 16H), 0.88 (t, 12H) |
| M-14 | 199–200 | (DMSO) 13.32 (s, 1H), 10.30 (s, 1H), 9.65 (s, 1H), 7.76 (d, 2H), 7.65–7.53 (m, 2H), 7.47 (dd, 1H), 7.25 (dd, 1H), 7.10 (d, 3H), 6.97 (d, 1H), 4.08 (t, 2H), 3.94 (t, 2H), 1.86–1.00 (m, 32H), 1.40 (s, 9H), 0.95–0.72 (m, 6H), 0.39 (s, 9H) |
| M-15 | 144–147 | (DMSO) 13.44 (s, 1H), 9.53 (s, 1H), 7.91–7.75 (m, 2H), 7.70 (d, 1H), 7.20–7.00 (m, 2H), 6.81 (d, 1H) 4.95 (t, 1H), 2.25 (s, 3H), 2.11–1.10 (m, 26H), 1.40 (s, 9H), 0.99 (t, 3H) 0.61 (t, 6H) |
| M-16 | 159–160 | (DMSO) 13.30 (s, 1H), 9.80 (s, 1H), 7.86–7.70 (m, 3H), 7.55 (d.d, 1H), 7.28 (d, 2H), 7.12 (d, 2H), 4.36–4.15 (m, 2H), 3.95–3.75 (m, 2H), 3.70–3.51 (m, 4H), 3.37–3.20 (t, 2H), 1.80–1.05(m, 16H), 1.39 (s, 9H) 0.80 (t, 3H), 0.52 (s, 9H) |
| M-17 | 109–110 | (DMSO) 13.31 (s, 1H), 10.54 (s, 1H), 8.44 (d, 1H), 8.12 (d.d, 1H), 7.83 (d, 2H), 7.31 (d, 1H), 7.25 (d, 2H), 4.31 (q, 2H), 4.18 (t, 2H), 1.72–1.50 (br, 2H), 1.50–1.00 (m, 35H), 1.38 (s, 9H), 0.86 (t, 3H) |
| M-18 | 135–140 | (DMSO) 13.31 (s, 1H), 10.52 (s, 1H), 8,45 (d, 1H), 8.11 (dd, 1H), 7.84 (d, 2H), 7.38–7.18 3H), 3.38 (br, 1H), 4.17 (t, 2H), 1.75–1.52 (br, 2H), 1.45–1.00 (m, 30H), 1.39 (s, 9H), 0.85 (t, 3H) |
| M-19 | 165–170 | (DMSO) 13.34 (s, 1H), 10.06 (s, 1H), 7.88–7.67 (m, 3H), 7.58 (dd, 1H), 7.26 (d, 2H), 7.12 (d, 1H), 5.20 (brs, 1H), 4.14 (t, 2H), 3.85 (t, 2H), 1.72–1.10 (m, 8H), 1.38 (s, 9H), 0.52 (s, 9H) |
| M-20 | 163–164 | (CDCl$_3$) 11.25 (br, 1H), 8.16 (s, 1H), |

TABLES 1 TO 14-continued

| Coupler No. | Melting point | Proton NMR δ (ppm) (multiplicity, integral value) |
|---|---|---|
| M-21 | 146–147 | (DMSO) 7.80 (d, 1H), 7.68 (d, 2H), 7.44 (d.d, 1H), 7.21 (d, 2H), 6.78 (d, 1H), 4.94 (t, 1H), 4.41–4.15 (m, 2H), 2.16–1.97 (br, 2H), 1.70–1.10 (m, 23H), 1.45 (s, 9H), 0.86 (t, 3H), 0.49 (s, 9H) 13.32 (s, 1H), 10.39 (s, 1H), 7.90–7.70 (m, 3H), 7.50 (d.d, 1H), 7.25 (d, 2H), 6.9 6 (d, 1H), 4.95 (s, 2H), 4.52–4.07 (m, 4H), 2.25 (t, 2H), 1.75–1.00 (m, 30H), 1.39 (s, 9H), 0.84 (t, 3H), 0.54 (s, 9H) |
| M-22 | 105–107 | (DMSO) 13.40 (brs, 1H), 10.85 (brs, 1H), 8.38–8.03 (m, 3H), 7.85 (d, 2H), 7.7 5 (t, 1H), 7.29 (d, 2H), 4.07 (t, 2H), 1.78–1.55 (br, 2H), 1.58–1.05 (m, 26H), 1.39 (s, 9H), 0.82 (t, 3H) |
| M-23 | 176–177 | (DMSO) 13.40 (brs, 1H), 10.90 (brs, 1H), 8.38–8.03 (m, 3H), 7.88 (d, 2H), 7.78 (t, 1H), 7.30 (d, 2H), 4.21 (d, 2H), 1.76–1.13 (m, 9H), 1.39 (s, 9H), 0.97–0.75 (m, 6H) |
| M-24 | 156–157 | (DMSO) 13.40 (brs, 1H), 10.89 (brs, 1H), 8.40–8.07 (m, 3H), 7.89 (d, 2H), 7.75 (t, 1H), 7.30 (d, 2H), 4.28 (t, 2H), 1.80–1.56 (br, 2H), 1.45–1.05 (m, 18H), 1.39 (s, 9H), 0.82 (t, 3H) |
| M-25 | 100–104 | (DMSO) 13.40 (brs, 1H), 10.89 (brs, 1H), 8.39–8.05 (m, 3H), 7.89 (d, 2H), 7.75 (t, 1H), 7.31 (d, 2H), 4.28 (t, 2H), 1.78–1.57 (m, 2H), 1.45–1.05 (m, 22H), 1.39 (s, 9H), 0.83 (t 3H) |
| M-26 | 181–182 | (CDCl$_3$) 12.60 (s, 1H), 10.20 (s, 1H), 8.55 (s, 1H), 8.17 (d.d, 1H), 8.00 (d.d, 1H), 7.86 (d, 2H), 7.53 (d.d, 1H), 7.28 (d, 2H), 4.31 (t, 2H), 1.85–1.63 (m, 2H), 1.50–1.10 (m, 14H), 1.46 (s, 9H), 0.89 (t, 3H) |
| M-27 | 137–138 | (DMSO) 13.35 (brs, 1H), 10.31 (s, 1H), 7.91 (d, 2H), 7.66 (d, 2H), 4.72 (s, 2H), 4.11 (t, 2H), 1.68–1.02 (m, 28H), 1.50 (s, 9H), 0.85 (t, 3H) |
| M-28 | 137–138 | (DMSO) 13.39 (s, 1H), 10.95 (s, 1H), 8.12 (d, 2H), 8.00 (d, 1H), 7.89 (d, 2H), 7.31 (d, 2H), 4.18 (d, 2H), 1.80–1.00 (m, 25H), 1.49 (s, 9H), 0.86 (t, 6H) |
| M-29 | 125–127 | (DMSO) 13.43 (brs, 1H), 11.02 (brs, 1H), 8.67–8.46 (m, 3H), 7.91 (d, 2H), –i.33 (d, 2H), 4.24 (d, 4H), 1.78–1.55 (br, 2H), 1.50–1.10 (m., 16H), 1.40 (s, 9H), 1.00–0.72 (m, 12H) |
| M-30 | 212–215 | (DMSO) 13.42 (s, 1H), 10.55 (s, 1H), 10.05 (s, 1H), 8.00 (s, 4H), 7.83–7.67 (m, 2H), 7.59–7.40 (m, 2H), 3.21–3.02 (m, 2H), 1.82–1.57 (br, 2H), 1.50–1.02 (m, 26H), 1.51 (s, 9H), 0.82 (t, 3H) |
| M-31 | 225–228 | (DMSO) 13.48 (brs, 1H), 10.80 (s, 1H), 8.50–8.20 (m, 2H), 8.15–7.9 8 (m, 5H), 7.81 (t, 1H), 7.70 (t, 2H), 2.70 (t, 2H), 1.55–1.05 (m, 9H), 1.42 (s, 9H), 0.93–0.69 (m, 6H) |
| M-32 | 157–158 | (CDCl$_3$) 12.62 (s, 1H), 10.25 (s, 1H), 8.55 (s, 1H), 8.17 (d.d, 1H), 8.02 (d.d 1H), 7.87 (d, 2H), 7.54 (d.d, 1H), 7.28 (d, 2H), 4.35 (t, 2H), 1.90–1.05 (m, 10H), 1.46 (s., 9H), 0.95 (d, 3H), 0.85 (d, 6H) |
| M-33 | 192–194 | (CDCl$_3$) 12.04 (s, 1H), 9.11 (s, 1H), 8.18 (d, 2H), 7.74 (d, 2H), 3.81 (t, 1H), 2.60 (t, 2H), 2.05–1.05 (m, 34H), 1.48 (s, 9H), 0.95–0.70 (m, 6H) |
| M-34 | 77–80 | (CDCl$_3$) 11.50 (br, 1H), 7.76 (d, 2H), 7.49 (s, 1H), 7.27 (d, 2H), 4.28–4.05 (m, 3H), 2.16–1.89 (m, 2H), 1.48 (s, 9H), 1.38–1.00 (m, 31H), 0.87 (t, 3H) |
| M-35 | 196–197 | (CDCl$_3$) 12.67 (s, 1H), 10.35 (s, 1H), 8.54 (s, 1H), 8.18 (d.d, 1H), 8.00 (d.d, 1H), 7.85 (d, 2H), 7.54 (d.d, 1H), 7.28 (d, 2H), 4.32 (t, 2H), 1.86–1.63 (m, 2H), 1.52–1.15 (m, 10H), 1.45 (s, 9H), 0.89 (t, 3H) |
| M-36 | 172–175 | (DMSO) 13.42 (s, 1H), 10.58 (s, 1H), 10.50 (s, 1H), 7.97 (d, 2H), 7.91–7.79 (m, 4H), 7.75 (d, 2H), 7.12 (d, 2H), 6.92 (d, 2H), 4.90 (t, 1H), 2.05–1.85 (br, 2H), 1.61–1.06 (m, 16H), 1.40 (s, 9H), 0.83 (t, 3H) |
| M-37 | 167–170 | (CDCl$_3$) 11.50 (br, 1H), 8.45 (br, 1H), 7.79 (s, 1H), 7.30–7.23 (m, 3H), 6.96 (d, 2H), 6.83 (d, 1H), 5.00(t, 1H), 2.23–1.96 (m, 2H), 1.75–1.00 (m, 28H), 1.40 (s, 9H), 0.88 (t, 3H), 0.50 (s, 9H) |
| M-38 | 95–98 | (DMSO) 13.35 (s, 1H), 10.31 (s, 1H), 7.92 (d, 2H), 7.67 (d, 2H), 5.48–5.32 (m, 1H), 4.25–3.92 m, 4H), 3.10–2.85 (m, 2H), 1.70–1.02 (m, 32H), 1.40 (s, 9H), 0.90–0.70 (m, 6H) |
| M-39 | 120–121 | (CDCl$_3$) 12.62 (s, 1H), 10.29 (s, 1H), 8.63 (s, 1H), 8.18 (s, 1H), 8.14 (s, 1H), 7.87 (d, 2H), 7.28 (d, 2H), 2.95 (t, 2H), 1.80–1.60 (m, 2H), 1.50–1.10 (m, 24H), 1.45 (s, 9H), 0.86 (t, 3H) |
| M-40 | 94–98 | (CDCl$_3$) 11.85 (br, 1H), 8.30 (s, 1H), 8.19 (d, 1H), 7.82 (d.d, 1H), 7.48 (d, 2H), 7.05 (d, 2H), 6.90 (d, 1H), 4.28 (t, 2H), 3.98 (t, 2H), 1.83–1.56 (m, 4H), 1.50–1.00 (m, 20H), 1.46 (s, 9H), 0.85 (t, 6H) |
| M-41 | 162–164 | (CDCl$_3$) 12.68 (s, 1H), 10.33 (s, 1H), 8.54 (s, 1H), 8.18 (d.d, 1H), 8.03 (d.d, 1H), 7.85 (d, 2H), 7.55 (d.d, 1H), 7.29 (d, 2H), 4.30–4.00 (m, 2H) 2.00–1.77 (m, 1H), 1.50–1.10 (m, 7H), 1.44 (s, 9H), 1.05–0.75 6H) |
| M-43 | 160–161 | (CDCl$_3$) 12.03 (brs, 1H), 8.90 (s, 1H), 7.80 (d, 2H), 7.49 (d, 2H), 4.02 (d, 2H), 2.95–2.68 (br, 4H), 2.50–2.17 (br, 1H), 1.72–1.05 (m, 24H), 1.48 (s, 9H), 1.00–0.70 (m, 6H) |
| M-44 | 181–182 | (DMSO-d$_6$) 13.47 (s, 1H), 10.20 (s, 1H), 7.92 (d, 2H), 7.78 (d, 2H), 3.92 (d, 2H), 2.50–2.25 (br, 4H), 2.00–1.75 (m, 2H), 1.68–1.03 (m, 25H), 1.40 (s, 9H), 0.93–0.70 (m, 6H) |
| M-45 | 182–183 | (DMSO-d$_6$) 13.38 (s, 1H), 10.30 (s, 1H), 7.92 (d, 2H), 7.77 (d, 2H), 4.00 (t,2H), 2.75–2.50 (br, 4H), 1.65–1.02 (m, 24H), 1.40 |

TABLES 1 TO 14-continued

| Coupler No. | Melting point | Proton NMR δ (ppm) (multiplicity, integral value) | |
|---|---|---|---|
| M-46 | 195-197 | (CDCl$_3$) | (s, 9H), 0.84 (t, 3H) 9.19 (s, 1H), 8.26 (s, 1H), 8.13 (d, 1H), 7.88 (d, 1H), 7.72 (d, 2H), 7.67-7.42 (m, 3H), 3.08-2-75 (m, 4H), 1.67-1.45 (br, 2H), 1.45-1.00 25H), 0.95-0-62 (m, 12H) |
| M-47 | 169-170 | (CDCl$_3$) | 12.88-12.55 (br, 1H), 10.31 (s,, 1H), 7.98 (d, 2H), 7.84 (d, 2H), 7.30 (d, 1H), 6.93 (d, 1H), 4.13 (d, 2H), 1.80-1.55 (br, 1H), 1.49 (s, 9H), 1.45-1.05 (br, 24H), 0.86 (t, 6H) |
| M-48 | 239-240 | (DMSO-d$_6$) | 13.43 (brs, 1H), 10.69 (s, 1H), 8.23-7.90 (m, 8H), 4.21 (d, 2H), 1.87-1.05 (m, 25H), 1.41 (s, 9H), 1.00-0.70 (m, 6H) |
| M-49 | 168-169 | (DMSO-d$_6$) | 13.39 (s, 1H), 10.30 (s, 1H), 7.92 (d, 2H), 7.78 (d, 2H), 4.9 7-4.7 5(br, 1H), 2.75-2.50 (br, 4H), 1.67-0.65 (m, 28H), 1.41 (s, 9H) |
| M-50 | 153-154 | (CDCl$_3$) | 12.08 (brs, 1H), 9.88 (s, 1H), 7.8 9 (d, 2H), 7.53 (d, 2H), 4.15-3.90 (br, 2H), 2.95-2.70 (br, 4H), 1.80-0.65 (m, 35H), 1.47 (s, 9H) |
| M-51 | 172-174 | (CDCl$_3$) | 12.35-12.15 (br, 1H), 10.04-9.80 (br, 1H), 7.94 (d, 2H), 7.54 (d, 2H), 3.40-2.98 (br, 4H), 2.97-2.68 (br, 4H), 1.85-0.95 (m, 24H), 1.49 (s, 9H), 0.88 (t, 3H), 0.81 (t, 3H) |
| M-52 | 210-211 | (CDCl$_3$) | 12.66 (s, 1H), 9.20 (s, 1H), 7.96 (d, 2H), 7.76 (d, 2H), 2.43-2.23 (m, 1H), 1.82-1.05 (m, 37H), 0.86 (t, 6H) |
| M-53 | decomp. at 300° C. | (CDCl$_3$) | 13.41 (s, 1H), 10.15 (s, 1H), 7.92 (d, 2H), 7.80 (d, 2H), 2.29-2.04 (dr, 1H), 1.92-0.72 (m, 43H) |
| M-54 | 152-153 | (CDCl$_3$) | 12.80-12.57 (br, 1H), 8.93 (s, 1H), 8.01 (d, 1H), 7.72 (d, 2H), 7.41 (d, 1H), 7.22 (d.d, 1H), 6.91 (d, 1H), 4.79 (t, 1H), 2.20-2.02 (m, 2H), 1.69 (s, 2H), 1.62-1.17 (m, 4H), 1.47 (s, 9H), 1.34 (s, H), 0.92 (t, 3H), 0.72 (s, 9H) |
| M-55 | 235-236 | (DMSO) | 13.49 (s, 1H), 10.73 (s, 1H), 8.30-7.95 (m, 8H), 4.25 (d, 2H), 1.90-1.68 (br, 1H), 1.67-1.10 (m, 33H), 0.87 (t, 6H) |
| M-56 | 151-152 | (CDCl$_3$) | 12.31 (brs, 1H), 8.71 (s, 1H), 8.11 (d, 2H), 7.71 (d, 2H), 4.15-4.02 (m, 1H), 3.68 (q, 2H), 2.00-1.06 (m, 25H), 1.49 (s, 9H), 0.86 (t, 3H) |
| M-57 | 161-162 | (CDCl$_3$) | 9.31 (s, 1H), 7.92 (d, 2H), 7.61 (d, 2H), 4.18 (s, 2H), 3.19 (s, 3H), 2.42 (t, 2H), 1.78-1.55 (br, 2H), 1.48 (s, 9H), 1.50-1.05 (br, 24H), 0.89 (t, 3H) |
| M-58 | 123-128 | — | |
| M-59 | 238-240 | (DMSO-d$_6$) | 13.47 (s, 1H), 10.84 (s, 1H), 10.22-10.02 (br, 1H), 8.10-7.70 6H), 7.50 (d, 1H), 2.27-2.00 (br, 1H), 1.85-0.65 34H), 1.40 (s, 9H) |
| M-60 | 127-128 | (CDCl$_3$) | 12.03 (s, 1H), 10.30 (s, 1H), 8.31 (dd, 1H), 7.96 (d, 2H) 7.61 (d, 2H), 7.54-7.40 (m, 1H), 7.10 (t, 1H), 6.99 (d, 1H), 4.10 (t, 2H), 2.08-1.85 |
| M-61 | 164-165 | (CDCl$_3$) | (br, 2H), 1.65-1.07 (m, 30H), 1.48 (s, 9H), 0.88 (t, 3H) 8.18 (s, 1H), 7.75 (d, 2H), 7.50 (d, 2H), 4.38 (s, 4H), 2.36 (t, 4H), 1.75-1.50 (br, 4H), 1.48 (s, 9H), 1.40-1.05 (m, 16H), 1.38 (s, 3H), 0.85 (t, 6H) |
| M-62 | 163-164 | (CDCl$_3$) | 7.94 (s.1H), 7.73 (d, 2H), 7.45 (d, 2H), 4.23 (s, 2H), 2.46 (t, 2H), 1.70-1.50 (br, 2H), 1.48 (s, 9H), 1.37 (s, 6H), 1.40-1.05 (m, 26H), 0.87 (t, 3H) |
| M-63 | 181-182 | (CDCl$_3$) | 12.17 (brs, 1H), 9.03 (brs, 1H), 7.83 (d, 2H), 7.50 (d, 2H), 4.09 (t, 2H), 2.94-2.65 (br, 4H), 1.70-1.05 (m, 20H), 1.47 (s, 9H), 0.87 (t, 3H) |
| M-64 | 182-183 | (DMSO-d$_6$) | 13.35 (s, 1H), 10.29 (s, 1H), 7.91 (d, 2H), 7.77 (d, 2H), 4.00 (t, 2H), 2.7 5-2.47 (br, 4H), 1.64-0.98 (m, 28H), 1.40 (s, 9H), 0.84 (t, 3H) |
| M-65 | 157-159 | (CDCl$_3$) | 11.90 (brs, 1H), 8.70 (s, 0.3H), 8.59 (s, 0.7H), 7.81-7.62 (m, 2H), 7.51-7.34 (m, 2H), 3.66 (s, 0.9H), 3.62 (s, 2.1H), 3.10-2.40 (m, 3H), 1.90-1.00 (m, 30H), 1.47 (s, 9H), 0.88 (t, 3H) |
| M-66 | 227-229 | (DMSO-d$_6$) | 13.44 (s, 1H), 10.79 (s, 1H), 8.65-8.52(br, 1H), 8.36-8.15 (m, 2H), 8.10-7.90 (m, 4H), 7.75 (t, 1H), 5.70 (t, 1H), 4.20 (q, 2H), 2.05-1.80 (br, 2H), 1.65-1.02 (m, 23H), 1.40 (s, 9H), 0.81 (t, 3H) |
| M-67 | 135-136 | (CDCl$_3$) | 12.45-12.22 (br, 1H), 9.79 (s, 1H), 8.02 (d, 2H), 7.61 (d, 2H), 3.45-3.06 (m, 4H), 2.90 (s, 4H), 1.74-1.55 (br, 2H), 1.50 (s, 9H), 1.40-0.97 (br, 16H), 0.94-0.65 (m, 12H) |
| M-68 | 181-182 | (DMSO-d$_6$) | 713.39 (s, 1H), 10.30 (s, 1H), 7.92 (d, 2H), 7.79 (d, 2H), 4.12-3.80 (br, 2H), 2.78-2.45 (br, 4H), 1.70-0.65 (m, 27H), 1.40 (s, 9H) |

The light-sensitive materials of the present invention may have at least one layer containing the coupler of the present invention provided on a support. The layer in which the couplers of the present invention are to be contained may be any of the hydrophilic colloid layers provided on the support. Generally, the hydrophilic colloid layers provided on the support of the light-sensitive material include light-sensitive silver halide emulsion layers, interlayers (e.g., a color mixing inhibiting layer interposed between silver halide emulsion layers), ultraviolet light absorbing layers, antihalation layers, protective layers and back layers. However, the layers in which the couplers of the present invention are contained are preferably silver halide emulsion layers or interlayers adjacent thereto.

It is preferred that the couplers of the present invention are used as magenta couplers in green-sensitive silver halide emulsion layers when they are applied to light-sensitive-materials.

The couplers of the present invention are used in an amount of usually $1 \times 10^{-3}$ to 1 mol, preferably $2 \times 10^{-3}$ to $3 \times 10^{-1}$ mol per mol of silver halide in the same emulsion layer.

The light-sensitive material of the present invention may comprise a support having thereon at least one blue-sensitive silver halide emulsion layer, at least one green-sensitive silver halide emulsion layer and at least one red-sensitive silver halide emulsion layer in this order. However, these layers may be arranged in a different order from that described above. Further, an infrared-sensitive silver halide emulsion layer may be used in place of at least one of the above light-sensitive emulsion layers. There is no particular limitation with regard to the number of the silver halide emulsion layers. Color reproduction by subtractive color photography can be made by containing color couplers in these light-sensitive emulsion layers, said color couplers forming dyes having a relation of complementary colors to light which is sensitive to silver halide emulsions having sensitivity to respective wavelength regions. The light-sensitive layers may not correspond to the hue of developed color as described above.

Each unit light-sensitive layer comprising a plurality of silver halide emulsion layers may be a two-layer structure composed of a high-sensitivity emulsion layer and a low-sensitivity emulsion layer as described in West German Patent 1,121,470 and U.K. Patent 923,045. Such a two-layer structure as mentioned above can be preferably used. Usually, it is preferred that these layers are arranged so that light sensitivity becomes lower toward the support. Further, a non-sensitive layer may be provided between silver halide emulsion layers. If desired, the low-sensitivity emulsion layer may be provided on the side which is farther away from the support, and the high-sensitivity emulsion layer may be provided on the side which is nearer the support as described in JP-A-57-112751, JP-A-62-200350, JP-A-62-206541 and JP-A-62-206543.

Concretely, the arrangement of the layer may be made in order of low-sensitivity blue-sensitive layer (BL)/high-sensitivity blue-sensitive layer (BH)/high-sensitivity green-sensitive layer (GH)/low-sensitivity green-sensitive layer (GL)/high-sensitivity red-sensitive layer (RH)/low-sensitivity red-sensitive layer (RL), in order of BH/BL/GL/GH/RH/RL or in order of BH/BL/GH/GL/RL/RH from the side which is farthest away from the support.

Further, there may be used a three-layer structure composed of three layers having different light sensitivity so arranged that light sensitivity is lowered toward the support in such a manner that the uppermost layer is a silver halide emulsion layer having the highest light sensitivity, an intermediate layer is a silver halide emulsion layer having light sensitivity lower than that of the uppermost layer, and the lowermost layer is a silver halide emulsion layer having light sensitivity lower than that of the intermediate layer as described in JP-B-49-15495 (the term "JP-B" as used herein means an "examined Japanese patent publication"). Even when the unit light-sensitive layer comprises such a three-layer structure composed of three layers having different light sensitivity, the arrangement of the layers having the same color sensitivity may be made in order of intermediate-sensitivity emulsion layer/high-sensitivity emulsion layer/low-sensitivity emulsion layer from the side which is farther away from the support as described in JP-A-59-202464.

It is preferred that a donor layer (CL) having an interlayer effect and having different spectral sensitivity distribution from that of the main light-sensitive layer such as BL, GL, RL as described in U.S. Pat. Nos. 4,663,271, 4,705,744 and 4,707,436, JP-A-62-160448 and JP-A-63-89850 is provided adjacent to or in the vicinity of the main light-sensitive layer.

As mentioned above, various layer structures and arrangements can be used according to the purposes of the light-sensitive materials.

The couplers of the present invention can be introduced into the light-sensitive materials by various conventional dispersion methods. Among them, there is preferred an oil-in-water dispersion method wherein the couplers are dissolved in a high-boiling organic solvent (optionally together with a low-boiling organic solvent), the resulting solution is emulsified and dispersed in an aqueous gelatin solution, and the resulting emulsified dispersion is added to a silver halide emulsion.

Examples of the high-boiling solvent which can be used in the oil-in-water dispersion method are described in U.S. Pat. No. 2,322,027. The stages and effects of latex dispersion methods as a polymer dispersion method and examples of impregnating latexes are described in U.S. Pat. No. 4,199,363, West German Patent Application (OLS) Nos. 2,541,274 and 2,541,230, JP-B-53-41091 and European Patent Laid-Open No. 029104. A dispersion method using organic solvent-soluble polymers is described in PCT WO 88/00723.

Specific examples of the high-boiling organic solvent which can be used in the oil-in-water dispersion method include phthalic acid esters (e.g., dibutyl phthalate, dioctyl phthalate, dicyclohexyl phthalate, di-2-ethylhexyl phthalate, decyl phthalate, bis(2,4-di-tert-amylphenyl) isophthalate, bis(1,1-diethylpropyl) phthalate), phosphoric or phosphonic acid esters (e.g., diphenyl phosphate, triphenyl phosphate, tricresyl phosphate, 2-ethylhexyl diphenyl phosphate, dioctyl butyl phosphate, tricyclohexyl phosphate, tri-2-ethylhexyl phosphate, tridecyl phosphate, di-2-ethylhexyl phenyl phosphate), benzoic acid esters (e.g., 2-ethylhexyl benzoate, 2,4-dichlorobenzoate, dodecyl benzoate, 2-ethylhexyl p-hydroxybenzoate), amides (e.g., N,N-diethyldodecaneamide, N,N-diethyllaurylamide), alcohols and phenols (e.g., isostearyl alcohol, 2,4-di-tert-amylphenol), aliphatic acid esters (e.g., dibutoxyethyl succinate, di-2-ethylhexyl succinate, 2-hexyldecyl tetradecanoate, tributyl citrate, diethyl azelate, isostearyl lactate, trioctyl citrate), aniline derivatives (e.g., N,N-dibutyl-2-butoxy-5-tert-octylaniline), chlorinated paraffins (e.g., chlorinated paraffins having a chlorine content of 10 to 80%), trimesic acid esters (e.g., tributyl ester of trimesic acid), dodecylbenzene, diisopropylnaphthalene, phenols (e.g., 2,4-di-tert-amylphenol, 4-dodecyloxyphenol, 4-dodecyloxycarbonylphenol, 4-(4-dodecyloxyphenylsulfonyl)phenol, carboxylic acids (e.g., 2-(2,4-di-tert-amylphenoxybutyric acid, 2-ethoxyoctanedecanoic acid) and alkylphosphoric acids (e.g., di-(2-ethylhexyl)phosphoric acid, diphenylphosphoric acid), organic solvents having a boiling point of not lower than 30° C., but not higher than about 160° C. may be used as auxiliary solvents together with the high-boiling organic solvents. Examples of the organic solvents which can be used as auxiliary solvents include ethyl acetate, butyl acetate, ethyl propionate, methyl ethyl ketone, cyclohexanone, 2-ethylethyl acetate and dimethylformamide.

The high-boiling organic solvents are used in an amount of 0 to 10.0 times, preferably 0.2 to 6.0 times, more preferably 0.5 to 5.0 times by weight the amount of the coupler. It is preferred from the viewpoints of hue, fastness to light and color developability that the high-boiling organic solvents re used in an amount of 2.5 to 5.0 times by weight the amount of the coupler.

Silver halide emulsions, other materials (e.g., additives), photographic constituent layers (e.g., layer arrangement), processing methods and processing additives described in the following patent specifications, particularly EP 0,355,660A2 can be preferably applied to the light-sensitive materials of the present invention.

| Photographic constituent element, etc. | JP-A-62-215272 | JP-A-2-33144 | EP0,355,660A2 |
|---|---|---|---|
| Silver halide emulsion | The 6th line of right upper column of page 10 to the 5th line of left lower column of page 12; and the 4th line from the bottom of right upper column of page 12 to the 17th line of left upper column of page 13 | The 16th line of right upper column of page 28 to the 11th line of right lower column of page 29; and the 2nd line to the 5th line of page 30 | The 53th line of page 45 to the 3rd line of page 47; and the 20th line to the 22nd line of page 47 |
| Solvents for silver halide | The 6th line to the 14th line of left lower column of page 12; and the third line from the bottom of left upper column of page 13 to the bottom of left lower column of page 18 | — | — |
| Chemical sensitizing agent | The 3rd line from the bottom of left lower column of page 12 to the 5th line from the bottom of right lower column of page 12; and the first line of right lower column of page 18 to the 9th line from the bottom of right upper column of page 22 | The 12th line to the bottom of right lower column of page 29 | The 4th line to the 9th line of page 47 |
| Spectral sensitizing agent (spectral sensitization method) | The 8th line from the bottom of right upper column of page 22 to the bottom of page 38 | The first line to the 13th line of left upper column of page 30 | The 10th line to the 15th line of page 47 |
| Emulsion Stabilizer | The 1st line of left upper column of page 39 to the bottom of right upper column of page 72 | The 14th line of left upper column of page 30 to the first line of right upper column of page 30 | The 16th line to the 19th line of page 47 |
| Development accelerator | The 1st line of left lower column of page 72 to the 3rd line of right upper column of page 91 | — | — |
| Color coupler (cyan, magenta and yellow couplers) | The 4th line of right upper column of page 91 to the 6th line of left upper column of page 121 | The 14th line of right upper column of page 3 to the bottom of left upper column of page 18; and the 6th line of right upper column of page 30 to the 11th line of right lower column of page 35 | The 15th line to the 27th line of page 4; the 30th line of page 5 to the bottom of page 28; the 29th line to the 31st line of page 45; and the 23rd line of page 47 to the 50th line of page 63 |
| Supersensitizing agent | The 7th line of left upper column of page 121 to the first line of right upper column of page 125 | — | — |
| Ultraviolet light absorber | The 2nd line of right upper column of page 125 to the bottom of left lower column of page 127 | The 14th line of right lower column of page 37 to the 11th line of left upper column of page 38 | The 22nd line to the 31st line of page 65 |
| Anti-fading agent (image stabilizer) | The 1st line of right lower column of page 127 to the 8th line of left lower column of page 137 | The 12th line of right upper column of page 36 to the 19th line of left upper column of page 37 | The 30th line of page 4 to the 23rd line of page 5; the 1st line of page 29 to the 25th line of page 45; the 33rd line to the 40th line of page 45; and the 2nd line to the 21st line of page 65 |
| High-boiling and/or low-boiling organic solvent | The 9th line of left lower column of page 137 to the bottom of right upper column of page 144 | The 14th line of right lower column of page 35 to the 4th line from the bottom of left upper column of page 36 | The 1st line to the 51st line of page 64 |
| Dispersion method of | The 1st line of left lower column of page 144 to | The 10th line of right lower column of page 27 to the | The 51st line of page 63 to the 56th |

-continued

| Photographic constituent element, etc. | JP-A-62-215272 | JP-A-2-33144 | EP0,355,660A2 |
|---|---|---|---|
| photographic additive | the 7th line of right upper column of page 146 | bottom of left upper column of page 28; and the 12th line of right lower column of page 35 to the 7th line of right upper column of page 36 | line of page 64 |
| Hardening agent | The 8th line of right upper column of page 146 to the 4th line of left lower column of page 155 | — | — |
| Developing agent precursor | The 5th line of left lower column of page 155 to the 2nd line of right lower column of page 155 | — | — |
| Restrainer releasing compound | The 3rd line to the 9th line of right lower column of page 155 | — | — |
| Support | The 19th line of right lower column of page 155 to the 14th line of left upper column of page 156 | The 18th line of right upper column of page 38 to the 3rd line of left upper column of page 39 | The 29th line of page 66 to the 13th line of page 67 |
| Layer structure | The 15th line of left upper column of page 156 to the 14th line of right lower column of page 156 | The 1st line to the 15th line of right upper column of page 28 | The 41st line to the 52nd line of page 45 |
| Dye | The 15th line of right lower column of page 156 to the bottom of right lower column of page 184 | The 12th line of left upper column of page 38 to the 7th line of right upper column of page 38 | The 18th line to the 22nd line of page 66 |
| Color mixing inhibitor | The 1st line of left upper column of page 185 to the 3rd line of right lower column of page 188 | The 8th line to the 11th line of right upper column of page 36 | The 57th line of page 64 to the 1st line of page 65 |
| Gradation controller | The 4th line to the 8th line of right lower column of page 188 | — | — |
| Stain inhibitor | The 9th line of right lower column of page 188 to the 10th line of right lower column of page 193 | The bottom of left upper column of page 37 to the 13th line of right lower column of page 37 | The 32th line of page 65 to the 17th line of page 66 |
| Surfactant | The 1st line of left lower column of page 201 to the bottom of right upper column of page 210 | The 1st line of right upper column of page 18 to the bottom of right lower column of page 24; and the 10th line from the bottom of left lower column of page 27 to the 9th line of right lower column of page 27 | — |
| Fluorine-containing compound (antistatic agent, coating aid, lubricant, anti-sticking agent, etc.) | The 1st line of left lower column of page 210 to the 5th line of left lower column of page 222 | The 1st line of left upper column of page 25 to the 9th line of right lower column of page 27 | — |
| Binder (hydrophilic colloid) | The 6th line of left lower column of page 222 to the bottom of left upper column of page 225 | The 8th line to the 18th line line of right upper column of page 38 | The 23rd line to the 28th line of page 66 |
| Thickener | The 1st line of right upper column of page 225 to the 2nd line of right upper column of page 227 | — | — |
| Antistatic agent | The 3rd line of right upper column of page 227 to the 1st line of left upper column of page 230 | — | — |
| Polymer latex | The 2nd line of left upper column of page 230 to the bottom of page 239 | — | — |
| Matting agent | The 1st line of left upper column of page 240 to the bottom of right upper column of page 240 | — | — |
| Photographic processing method (processing stage, | The 7th line of right upper column of page 3 to the 5th line of right upper column of page 10 | The 4th line of left upper column of page 39 to the bottom of left upper column of page 42 | The 14th line of page 67 to the 28th line of page 69 |

| -continued | | | |
|---|---|---|---|
| Photographic constituent element, etc. | JP-A-62-215272 | JP-A-2-33144 | EP0,355,660A2 |
| additive, etc.) | | | |

Note The cited places of JP-A-62-215272 include amendment dated March 16, 1987 and attached to the end of the publication. Among the above color couplers, short wave type yellow couplers described in JP-A-63-231451, JP-A-63-123047, JP-A-63-241547, JP-A-1-173499, JP-A-1-213648, and JP-A-1-250944 are preferred as the yellow couplers.

Any of silver chloride, silver bromide, silver chlorobromide, silver iodochloride, silver iodochlorobromide and silver iodobromide can be used as silver halide in the present invention. Among them, silver iodobromide, silver iodochloride or silver iodochlorobromide having a silver iodide content of 0.1 to 30 mol % are preferred and silver iodide or silver iodobromide having a silver iodide content of 1 to 25 mol % are particularly preferred when silver halide is applied to color light-sensitive materials for photographing or reversal color light-sensitive materials (e.g., color negative films, reversal films, reversal color paper). When silver halide is applied to direct positive color light-sensitive materials (e.g., color proofs containing previously fogged internal latent image type emulsions), silver chloride, silver bromide or silver chlorobromide is preferred, and silver bromide is particularly preferred. When silver halide is applied to light-sensitive materials for paper, silver chloride or silver chlorobromide containing substantially no silver iodide is preferred, and silver chlorobromide having a silver chloride content of preferably not lower than 80 mol%, more preferably not lower than 95 mol %, most preferably not lower than 98 mol % or pure silver chloride emulsion is particularly preferred.

The light-sensitive materials of the present invention may contain various color couplers in the same layer or in different layers, so long as the effect of the present invention can be obtained. Concrete examples of the color couplers are described in patent specifications cited in Research Disclosure (RD) No. 17643, item VII-C to G and ibid. No. 307105, item VII-C to G, JP-A-62-215272, JP-A-3-33847, JP-A-2-33144 and European Patent Laid-Open Nos. 447,969A and 482,552A.

Examples of yellow couplers include those described in U.S. Pat. Nos. 3,933,501, 4,022,620, 4,326,024, 4,401,752 and 4,248,961, JP-B-58-10739, U.K. Patents 1,425,020 and 1,476,760, U.S. Pat. Nos. 3,973,968, 4,314,023, 4,511,649 and 5,118,599, European Patents 249, 473A and 0,447,969, JP-A-63-23145, JP-A-63-123047, JP-A-1-250944 and JP-A-1-213648.

Particularly preferred examples of yellow couplers include yellow couplers of general formula (Y) described in JP-A-2-139544 (left upper column of page 18 to left lower column of page 22), acylacetamide yellow couplers (characterized by acyl group) described in Japanese Patent Application No. 3-179042 and European Patent Laid-Open No. 0,447,969, and yellow couplers of general formula (Cp-2) described in Japanese Patent Application No. 3-203545 and European Patent Laid-Open No. 0,446,863A2.

Preferred magenta couplers include 5-pyrazolone compounds and pyrazoloazole compounds. Magenta couplers described in U.S. Pat. Nos. 4,310,619 and 4,351,897, European Patent 73,636, U.S. Pat. Nos. 3,061,432 and 3,725,067, Research Disclosure No. 24220 (June 1984), JP-A-60-33552, Research Disclosure No. 24230 (June 1984), JP-A-60-43659, JP-A-61-72238, JP-A-60-35730, JP-A-55-118024, JP-A-60-185951, U.S. Pat. Nos. 4,500,630, 4,540,654 and 4,556,630 and PCT WO88/04795 are more preferred.

Particularly preferred magenta couplers are pyrazoloazole magenta couplers of general formula (I) described in JP-A-2-139544 (right lower column of page 3 to right lower column of page 10) and 5-pyrazolone magenta couplers of general formula (M-1) described in JP-A-2-139544 (left lower column of page 17 to left upper column of page 21). Most preferred are the above-described pyrazoloazole magenta couplers.

Cyan couplers include phenol couplers and naphthol couplers. Cyan couplers described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Laid-Open No. 3,329,729, European Patents 0,121,365A and 0,249,453A, U.S. Pat. Nos. 3,446,622, 4,333,999, 4,775,616, 4,451,559, 4,427,767, 4,690,889, 4,254,212 and 4,296,199 and JP-A-61-42658 are preferred. Further, there can be used pyrazoloazole couplers described in JP-A-64-553, JP-A-64-554, JP-A-64-555 and JP-A-64-556; pyrrolotriazole couplers described in European Patent Laid-Open Nos. 0,488,248 and 0,491,197; pyrroloimidazole couplers described in European Patent Laid-Open No. 0,456,226A; pyrazolopyrimidine couplers described in JP-A-64-46753; imidazole couplers described in U.S. Pat. No. 4,818,672 and JP-A-2-33144; cyclic active methylene type cyan couplers described in JP-A-64-32260; and couplers described in JP-A-1-183658, JP-A-2-262655, JP-A-2-85851 and JP-A-3-48243.

Typical examples of dye forming polymer couplers are described in U.S. Pat. Nos. 3,451,820, 4,080,211, 4,367,282, 4,409,320 and 4,576,910, U.K. Patent 2,102,137 and EP 341,188A.

Preferred examples of couplers which give developed dyes having proper diffusibility include those described in U.S. Pat. No. 4,366,237, U.K. Patent 2,125,570, EP 96,570 and West German Patent Laid-Open No. 3,234,533.

Couplers which release photographically useful residual group by coupling can be used in the present invention. Preferred examples of DIR couplers which release a restrainer include those described in patent specifications cited in the aforesaid RD No. 17643, item VII-F, JP-A-57-151944, JP-A-57-154234, JP-A-60-184248, JP-A-63-37346 and U.S. Pat. Nos. 4,248,962 and 4,782,012.

Preferred examples of couplers which release imagewise a nucleating agent or a development accelerator during development include those described in U.K. Patents 2,097,140 and 2,131,188, JP-A-59-157638 and JP-A-59-170840.

Examples of other couplers which can be used in the color photographic elements of the present invention include competitive couplers described in U.S. Pat. No. 4,130,427; polyequivalent type couplers described in U.S. Pat. Nos. 4,283,472, 4,338,393 and 4,310,618; DIR redox compound-releasing couplers, DIR coupler releasing couplers, DIR coupler-releasing redox compounds and DIR redox-releasing redox compounds described in JP-A-60-185950 and JP-A-62-24252; couplers which release a dye whose color is restored to the original color after elimination as described in European Patent 173,302A; bleaching accelerator-releasing couplers described in RD No. 11449, ibid. No. 24241 and JP-A-61-201247; ligand-releasing couplers described in U.S. Pat. No. 4,553,477; leuco dye-releasing couplers described in JP-A-63-75747; and fluorescent dye releasing couplers described in U.S. Pat. No. 4,774,181.

It is preferred that the hydrophilic colloid layers of the light-sensitive materials of the present invention contain dyes decolorizable by processing (particularly oxonol dyes) (as described in EP 0,337,490A2, pages 27 to 76) in such an amount as to give an optical reflection density of at least 0.70 at 680 nm to improve the sharpness of image, or that at least 12 wt % (more preferably at least 14 wt %) of titanium oxide having a surface treated with a divalent to tetravalent alcohol (e.g., trimethylol ethane) is contained in the water-resistant resin layer of the support to improve the sharpness of image.

When various anti-fading agents in combination are contained in the light-sensitive materials of the present invention, properties with regard to fading in high density developed color area as well as in low density developed color area can be improved, and well-balanced color with regard to fading of three colors of yellow, magenta and cyan can be obtained.

Examples of organic anti-fading agents for cyan, magenta and/or yellow dye images include hydroquinones, 6-hydroxy chromans, 5-hydroxycoumarans, spiro-chromans, p-alkoxyphenols, hindered phenols such as typically bisphenols, gallic acid derivatives, methylenedioxybenzenes, aminophenols and ether or ester derivatives obtained by silylating or alkylating the phenolic hydroxy group of these compounds. Further, metal complexes such as typically (bissalicyl-aldoximato)-nickel complex and (bis-N,N-dialkyldithiocarbamato)-nickel complex can be used.

Specific examples of the organic anti-fading agents include hydroquinones described in U.S. Pat. Nos. 2,360,290, 2,418,613, 2,700,453, 2,701,197, 2,728,659, 2,732,300, 2,735,765, 3,982,944 and 4,430,425, U.K. Patent 1,363,921 and U.S. Pat. Nos. 2,710,801 and 2,816,028; 6-hydroxychromans, 5-hydroxycoumarans and spiro-chromans described in U.S. Pat. Nos. 3,432,300, 3,573,050, 3,574,627, 3,698,909 and 3,764,337 and JP-A-52-152225; spiro-indanes described in U.S. Pat. No. 4,360,589; p-alkoxyphenols described in U.S. Pat. No. 2,735,765, U.K. Patent 2,066,975, JP-A-59-10539 and JP-B-57-19765; hindered phenols described in U.S. Pat. Nos. 3,700,455 and 4,228,235, JP-A-52-72224 and JP-B-52-6623; gallic acid derivatives described in U.S. Pat. No. 3,457,079; methylenedioxybenzenes described in U.S. Pat. No. 4,332,886; aminophenols described in JP-B-56-21144; hindered amines described in U.S. Pat. Nos. 3,336,135 and 4,268,593, U.K. Patents 1,326,889, 1,354,313 and 1,410,846, JP-B-51-1420, JP-A-58-114036, JP-A-59-53846, JP-A-59-78344, JP-A-1-250955 (compounds of formula III), JP-A-2-208635 (compounds of formula II) and JP-A-2-217845 (compounds of formula III); metal complexes described in U.S. Pat. Nos. 4,050,938 and 4,241,155 and U.K. Patent 2,027,731(A); and phosphorus compounds described in JP-A-1-287564 (compounds of formula A-1)
and JP-A-3-25438 (compounds of formula II). These compounds (in an amount of usually 5 to 100% by weight based on the amount of the corresponding coupler) are co-emulsified together with couplers and added to the light-sensitive layers, whereby the object thereof can be achieved. These compounds may be used in combinations of two or more of them to improve their effect. For example, these compounds may be used together with pyrazoloazole couplers described in JP-A-2-139544 and can be preferably used together with the couplers of the present invention.

It is preferred that the light-sensitive materials of the present invention contain dye image preservability-improving compounds of general formulas (IV), (V) and (VI) described in EP 0,277,589A2 and JP-A-3-48845 together with the couplers. Namely, it is preferred that the light-sensitive materials of the present invention contain a compound (F) and/or a compound (G), said compound (F) being chemically bonded to an aromatic amine developing agent left behind after color development to form a compound which is chemically inert and substantially colorless, and said compound (G) being chemically bonded to the oxidation product of an aromatic amine developing agent left behind after color development to form a compound which is chemically inert and substantially colorless. The use of these compounds is preferred from the viewpoint of preventing stain from being formed by a developed dye produced by the reaction of the coupler with a color developing agent or the oxidant thereof left behind in the layer during storage after processing or to prevent other side effects from being caused. It is preferred that the aforesaid anti-fading agents and these dye image preservability-improving compounds are used together with the couplers of the present invention. For example, a method described in JP-A-3-48845 may be mentioned and can be preferably applied to the couplers of the present invention.

The light-sensitive materials of the present invention may contain, as color fogging inhibitors, hydroquinone derivatives, aminophenol derivatives, gallic acid derivatives and ascorbic acid derivatives.

It is more effective in preventing cyan dye image from being deteriorated by heat and particularly light that ultraviolet light absorbers are contained in the cyan color forming layer and both layers adjacent thereto. Examples of the ultraviolet light absorbers include aryl group-substituted benztriazole compounds (e.g., those described in U.S. Pat. No. 3,533,794), 4-thiazolidone compounds (e.g., those described in U.S. Pat. Nos. 3,314,794 and 3,352,681), benzophenone compounds (e.g., those described in JP-A-46-2784), cinnamic esters (e.g., those described in U.S. Pat. Nos. 3,705,805 and 3,707,395), butadiene compounds (e.g., those described in U.S. Pat. No. 4,045,229), triazine compounds (e.g., those described in JP-A-46-3335) and benzoxazole compounds (e.g., those described in U.S. Pat. Nos. 3,406,070 and 4,271,307) . Ultraviolet light absorbing couplers (e.g., α-naphthol cyan dye forming couplers) and ultraviolet light absorbing polymers may be used. These ultraviolet light absorbers may be mordanted into a specific layer. Among these compounds, the aryl group-substituted benztriazole compounds are preferred.

It is preferred that the hydrophilic colloid layers of the light-sensitive materials of the present invention contain antifungal agents as described in JP-A-63-271247 to prevent image from being deteriorated by the growth of mold and bacteria in the layers.

Examples of suitable supports which can be used in the present invention include those described in the aforesaid *Research Disclosure* (RD) No. 17643, page 28 and ibid. No. 18716 (right column of page 647 to left column of page 648).

As supports used for the light-sensitive materials of the present invention, there may be used white polyester supports for display and supports wherein a white pigment-containing layer is provided on the silver halide emulsion layer side thereof. It is preferred that an antihalation layer is provided on the silver halide emulsion layer-coated side of the support or on the back sides thereof. It is also preferred that the transmission density of the support is set to a value in the range of 0.35 to 0.8 so as to allow display to be enjoyed by reflected light as well as transmitted light.

The light-sensitive materials of the present invention may be exposed to visible light or infrared light. Exposure method may be low illumination exposure or high illumination short, time exposure. In the latter case in particular, a laser beam scanning exposure system wherein exposure time per one pixel is shorter than $10^{-4}$ seconds is preferred.

It is preferred that a band stop filter described in U.S. Pat. No. 4,880,726 is used when exposure is conducted. When this filter is used, light color mixing can be eliminated and color reproducibility can be improved.

After imagewise exposure, the light-sensitive materials of the present invention are subjected to color development, desilverization and rinsing and/or stabilization.

The details of the processing methods of the light-sensitive materials are described in *Research Disclosure* No. 17643, pp. 28 to 29, *Research Disclosure* No. 17643 (left column to right column of page 651), *Research Disclosure* No. 307105, pp. 880 to 881, JP-A-2-207250 (the first line of right lower column of page 26 to the 9th line of right upper column of page 34), JP-A-4-97355 (the 17th line of left lower column of page 5 to the 20th line of right lower column of page 18), JP-A-3-33847, JP-A-3-213853, JP-A-3-237456, JP-A-3-293662 and JP-A-4-130432 in addition to the patent specifications listed hereinbefore.

Color developing gents described in the aforesaid *Research Disclosure* and patent specifications, European Patent Laid-Open No. 410450 and JP-A-4-11255 can be preferably used in the color development stage.

Generally, the desilverization stage comprises a bleaching stage, a bleaching-fixing stage and a-fixing stage. More specifically, examples of the desilverization stage include the following combinations.

Bleaching-fixing
Bleaching-rinsing-fixing
Bleaching-blixing
Bleaching-rinsing-blixing
Bleaching-blixing-fixing
Blixing
Fixing-bleaching-fixing Conventional bleaching agents can be used as bleaching agents in the bleaching solutions or in the blixing solutions. Preferred bleaching agents are iron(III) complex salts of organic acids. Examples of the organic acids which can be used in the preparation of the iron-(III) complex salts of the organic acids include ethylenediaminetetraacetic acid, 1,3-diaminopropanetetraacetic acid, 1,4-butylenediaminetetraacetic acid, diethylene thioether diaminetetraacetic acid, glycol ether diaminetetraacetic acid, diethylenetriaminepentaacetic acid, cyclohexanediaminetetraacetic acid, iminodiacetic acid, methylaminodiacetic acid and N-(2-acetamido)iminodiacetic acid. In addition to the iron-(III) complex salts of the organic acids, there can be preferably used the metal complex salts of organic acids described in JP-A-63-80256, JP-A-63-97952, JP-A-63-97953, JP-A-63-97954, JP-A-1-93740, JP-A-3-216650, JP-A-3-180842, JP-A-4-174432, JP-A-5-113631, JP-A-5-66527, European Patent Laid-Open Nos. 458,131A1, 461,413A1, 461,676A1, 468,325 and 430,000A1, West German Patent Laid Open No. 3,912,551, and Japanese Patent Application Nos. 2-196972 and 4-129769. These bleaching agents may be used either alone or in combination of two or more of them in the processing solutions having an ability of bleaching.

Generally, ammonium thiosulfate is used as the fixing agent in the blixing solutions or in the fixing solutions. However, there can be used other conventional fixing agents such as meso-ionic compounds, thioether compounds, thioureas, iodides and hypo. The details thereof are described in JP-A-60-61749, JP-A-60-147735, JP-A-64-21444, JP-A-1-201659, JP-A-1-210951, JP-A-2-44355 and U.S. Pat. No. 4,378,424.

Stabilizing solutions described in U.S. Pat. No. 4,786,583 can be used in the rinsing stage and stabilization stage of the present invention. Formaldehyde can be used as the stabilizing agent in the stabilizing solutions. However, N-methylol azoles, hexamethylenetetramine, formaldehyde bisulfite adducts, dimethylol urea and azolylmethylamine derivatives are preferred from the viewpoint of the safety of working atmosphere. These compounds are described in JP-A-2-153348, JP-A-5-34889, JP-A-4-214556 and JP-A-4-313753. Particularly, the use of a combination of azoles such as 1,2,4-triazole and azolylmethylamines such as 1,4-bis(1,2,4-triazol-1-ylmethyl)piperazine or derivatives thereof (described in JP-A-4-359249) is preferred because image stability is high and formaldehyde vapor pressure is low.

The present invention is now illustrated in greater detail by reference to the following examples which, however, are not to be construed as limiting the invention in any way.

EXAMPLE 1

The coupling reaction product, i.e., a dye, of the coupler M-1 of the present invention with the oxidation product of the developing agent (D-1) was synthesized according to the following reaction scheme (E).

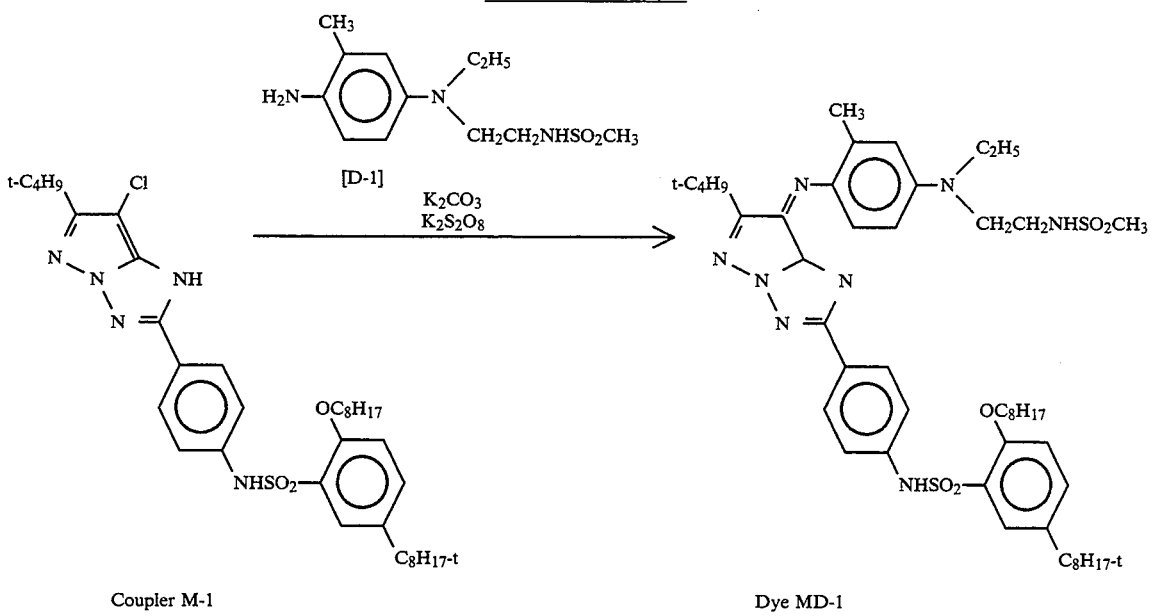

Coupler M-1     Dye MD-1

To 1.0 g of coupler M-1, 1.0 g of developing agent D-1 and 10 g of potassium carbonate, there were added 100 ml of water, 100 ml of ethyl acetate and 30 ml of ethanol. The mixture was stirred at room temperature. To the resulting solution, there was added 1.0 g of ammonium persulfate, and the mixture was stirred for one hour. After completion of the reaction, the aqueous layer was removed, and the ethyl acetate solution was washed with water and then concentrated under reduced pressure. The residue was separated from silica gel column chromatography and recrystallized from a mixed solvent of n-hexane and ethyl acetate. There was obtained 0.87 g of dye MD-1. Melting point: 158 to 162° C.

In the same manner as described above, dyes MD-2 to MD-18 were synthesized from couplers M-2 to M-13, M-15, M-28, M-29, M-43 and M-45, respectively.

In the same manner as described above, dyes MD-19, MD-20 and MD-21 were synthesized from comparative couplers a, b and c, respectively.

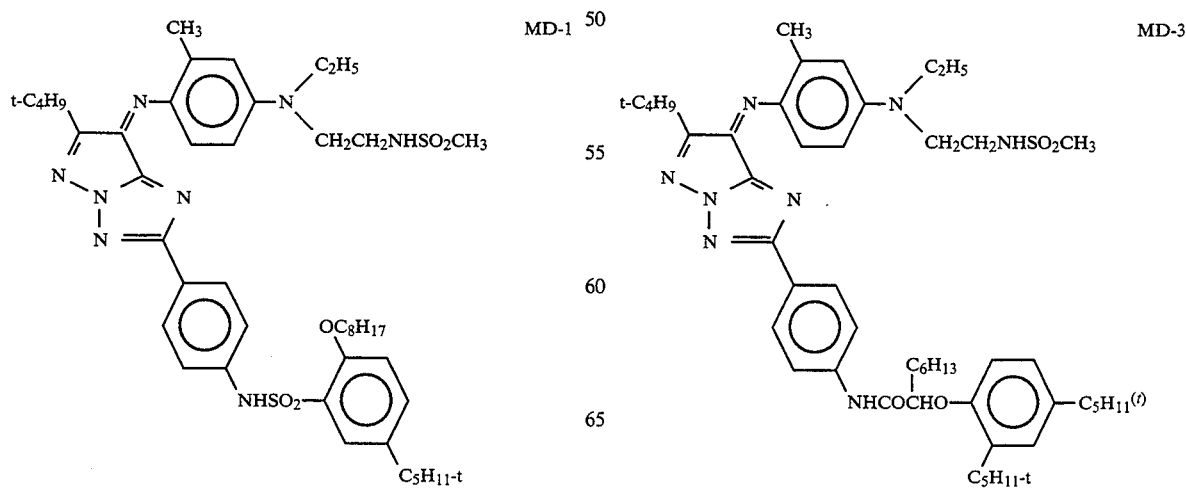

-continued
MD-4
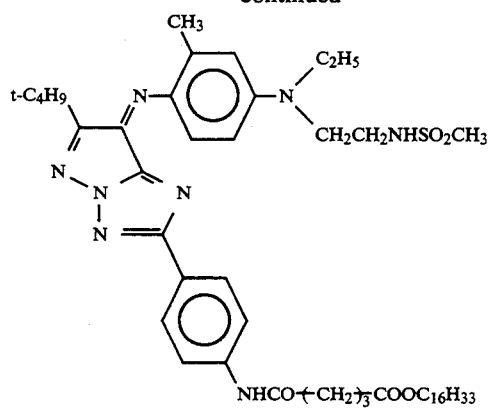
MD-5
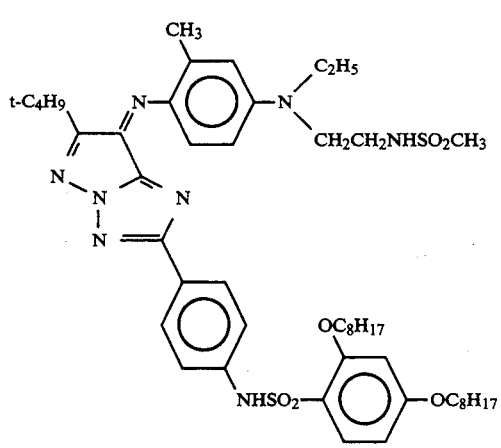
MD-6
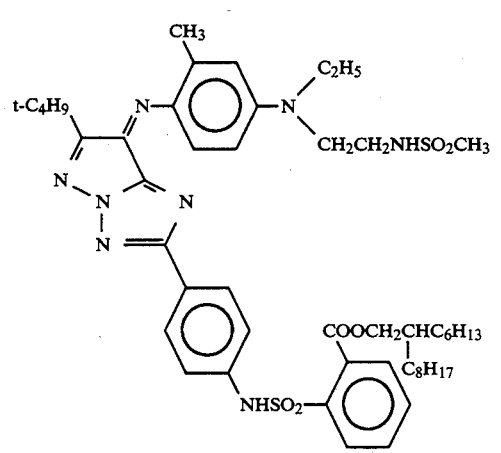
MD-7
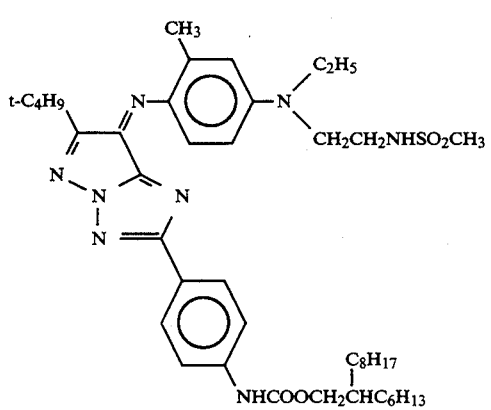
-continued
MD-8
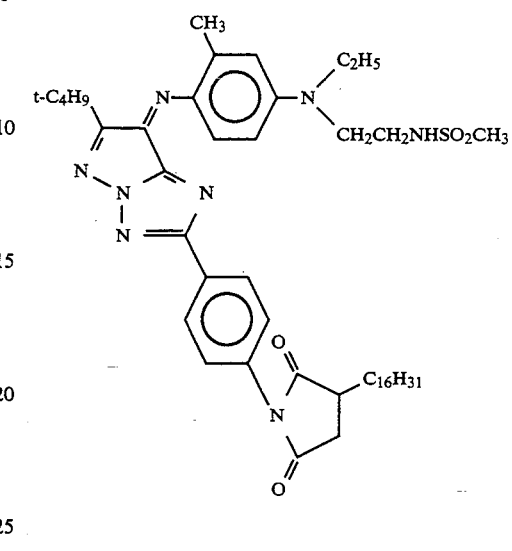
MD-9
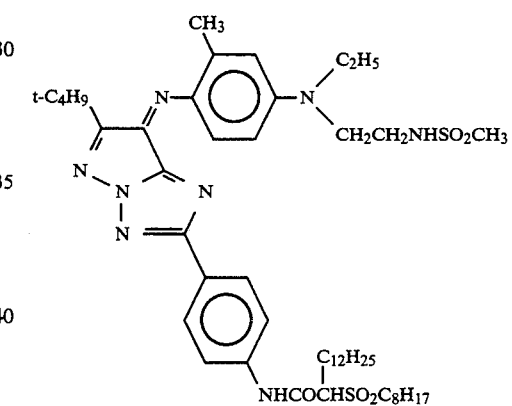
MD-10
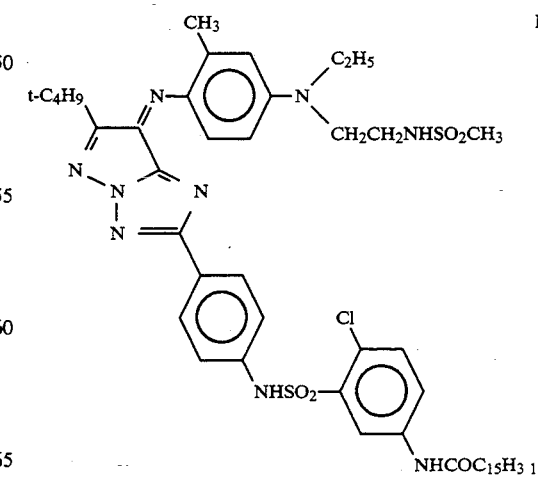

-continued
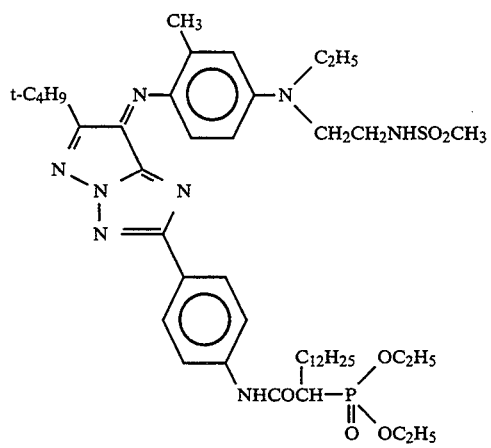
MD-11
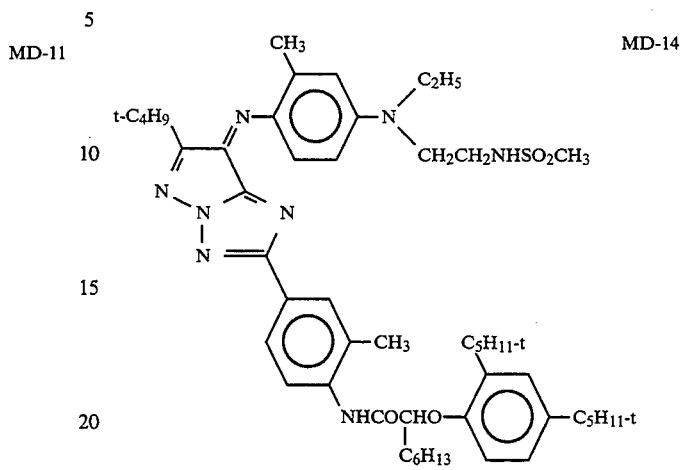
MD-14
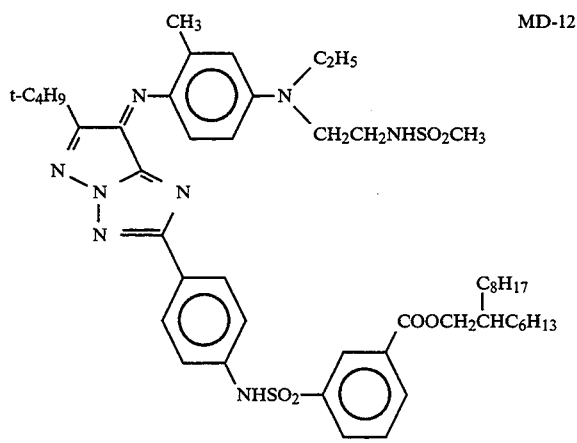
MD-12
MD-15
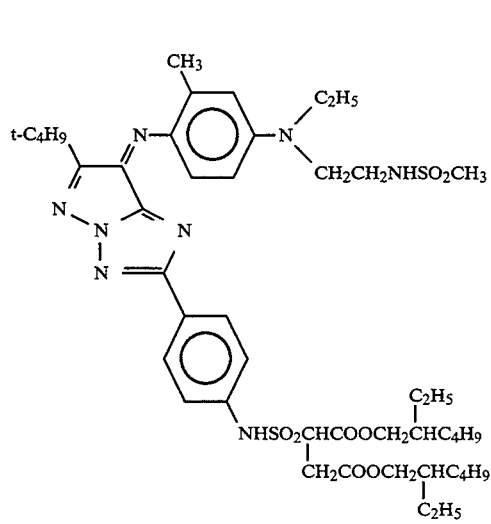
MD-13
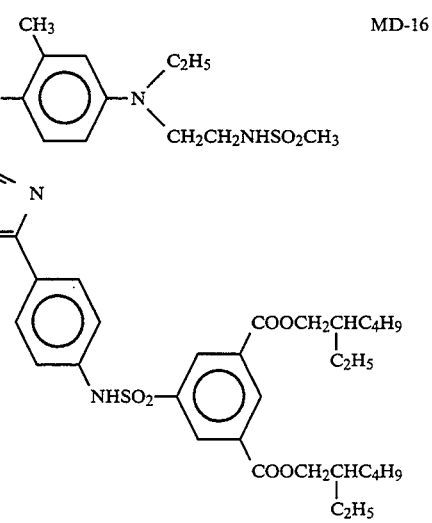
MD-16

-continued
MD-17
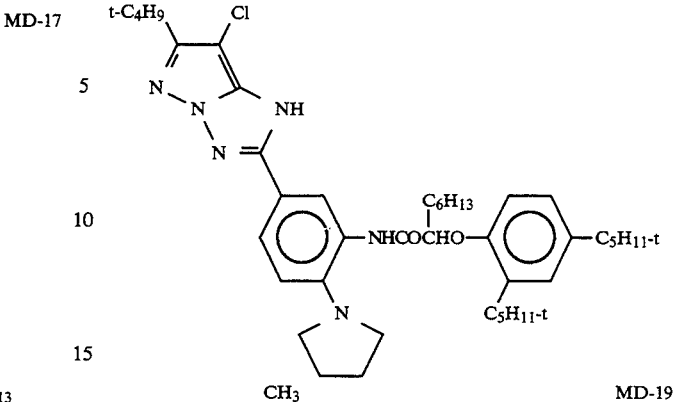
MD-18
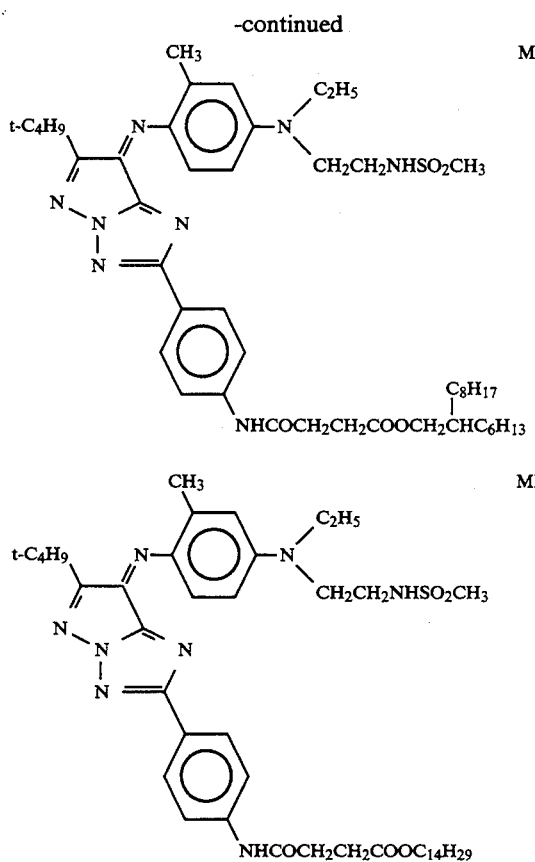
Comparative coupler (a) (coupler described in U.S. Pat. No. 4,882,266)
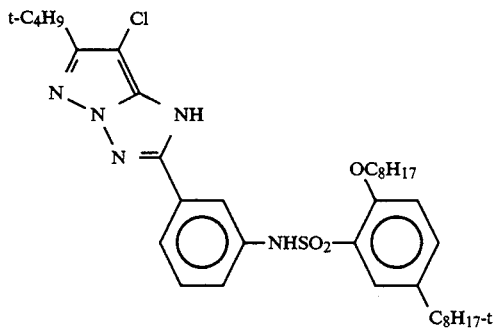
Comparative coupler (b)
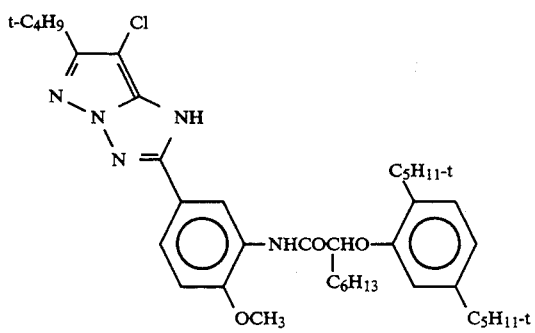
Comparative coupler (c)
-continued
MD-19
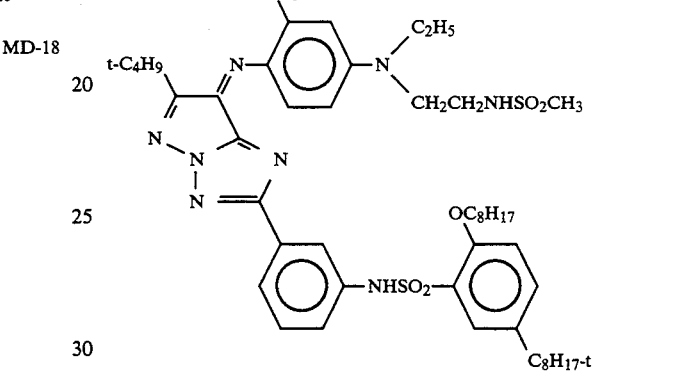
MD-20
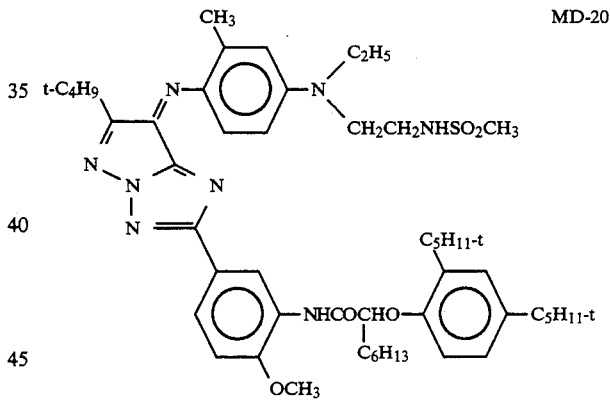
MD-21
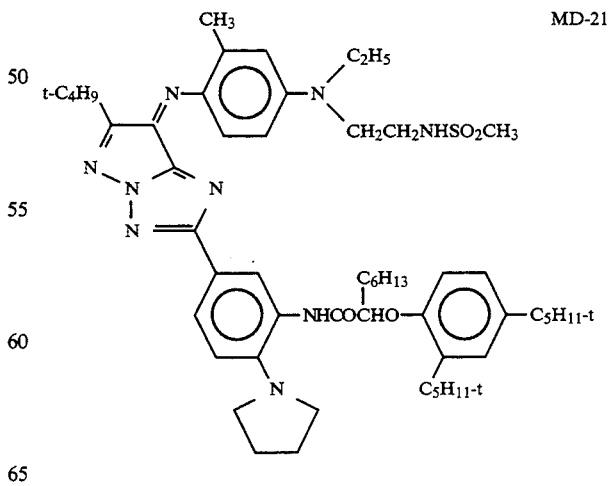
Each of dyes M-1 to M-21 synthesized above was dissolved in ethyl acetate, and visible absorption spectrum was measured. Maximum absorption wavelength (λmax), an extinction coefficient (ε), a half width (λ/2), a value (Δλ₁) which represents a degree of the cut of the foot on the short wavelength side and a value (Δλ₂) which represents a degree of the cut of the foot on the long wavelength side, are shown in Table 15.

Each of the values λ/2, Δλ₁ and Δλ₂ was measured by controlling the concentration of the dye to a value which gave absorbance of 1.0. The values of λ/2, Δλ₁ and Δλ₂ were determined from the visible absorption spectrum curve as shown in FIG. 1. Namely, λ/2 is a value of the width of absorption at an absorbance of 0.5; the value Δλ₁ is a difference (Δλ₁=λmax-a) between λmax and the value of long wave at an absorbance of 0.1 on the short wavelength side; and the value Δλ₂ is a difference (Δλ₂=b-λmax) between λmax and the value of long wave at an absorbance of 0.1 on the long wavelength side.

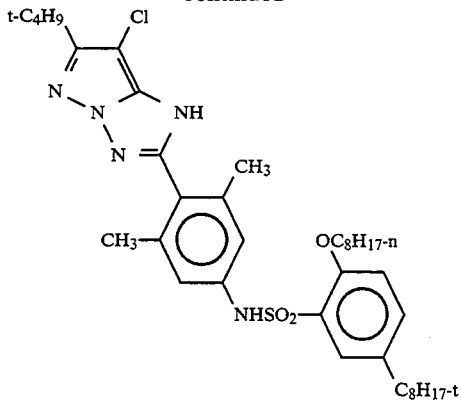
-continued

TABLE 15

| Dye No. | Coupler No. | Melting point (°C.) | Extinction coefficient (ε) | Maximum absorption wavelength (λmax) (nm) | Half width (λ½) (nm) | Δλ₁ (nm) | Δλ₂ | |
|---|---|---|---|---|---|---|---|---|
| MD-1 | M-1 | 158–162 | 5.35 × 10⁴ | 540.2 | 68.9 | 82.7 | 54.9 | Invention |
| MD-2 | M-2 | 157–158 | 5.33 × 10⁴ | 540.3 | 69.0 | 83.0 | 55.4 | " |
| MD-3 | M-3 | 140–141 | 5.23 × 10⁴ | 540.7 | 69.0 | 83.7 | 55.7 | " |
| MD-4 | M-4 | 92–97 | 5.31 × 10⁴ | 539.7 | 69.4 | 83.7 | 55.8 | " |
| MD-5 | M-5 | 170–171 | 5.41 × 10⁴ | 540.5 | 69.0 | 83.4 | 55.5 | " |
| MD-6 | M-6 | 123–124 | 5.40 × 10⁴ | 541.9 | 68.3 | 83.0 | 55.3 | " |
| MD-7 | M-7 | 150–151 | 5.30 × 10⁴ | 539.0 | 69.7 | 81.7 | 54.6 | " |
| MD-8 | M-8 | 155–157 | 5.42 × 10⁴ | 542.2 | 67.6 | 82.7 | 55.1 | " |
| MD-9 | M-9 | 151–152 | 5.30 × 10⁴ | 540.5 | 69.0 | 83.4 | 55.9 | " |
| MD-10 | M-10 | 153–155 | 5.32 × 10⁴ | 541.6 | 68.5 | 83.4 | 55.4 | " |
| MD-11 | M-11 | 140–143 | 5.32 × 10⁴ | 540.0 | 69.4 | 83.7 | 55.9 | " |
| MD-12 | M-12 | 118–120 | 5.46 × 10⁴ | 541.7 | 68.1 | 83.1 | 54.7 | " |
| MD-13 | M-13 | 63–72 | 5.40 × 10⁴ | 541.6 | 68.3 | 83.1 | 55.3 | " |
| MD-14 | M-15 | 130–132 | 5.25 × 10⁴ | 540.4 | 69.2 | 83.2 | 55.8 | " |
| MD-15 | M-28 | 120–124 | 5.32 × 10⁴ | 541.8 | 68.3 | 82.9 | 55.2 | Invention |
| MD-16 | M-29 | 186–188 | 5.30 × 10⁴ | 542.3 | 67.8 | 82.7 | 54.5 | " |
| MD-17 | M-43 | 109–111 | 5.20 × 10⁴ | 539.3 | 69.6 | 83.8 | 55.8 | " |
| MD-18 | M-45 | 135–137 | 5.59 × 10⁴ | 539.5 | 68.3 | 83.5 | 55.3 | " |
| MD-19 | Comparative coupler a | 147–156 | 4.85 × 10⁴ | 541.6 | 68.5 | 82.8 | 59.8 | Comp. Ex. |
| MD-20 | Comparative coupler b | 133–134 | 4.81 × 10⁴ | 538.4 | 71.3 | 84.2 | 61.9 | " |
| MD-21 | Comparative coupler c | 136–138 | 4.83 × 10⁴ | 538.4 | 71.6 | 84.1 | 62.5 | " |

It has been found in Table 15 that the dyes obtained from the couplers of the present invention have a high extinction coefficient and a small Δλ₂ value in particular and are excellent in the cut of the foot on the long wavelength side in comparison with the dyes obtained from comparative couplers. It can be considered that the couplers of the present invention scarcely cause color turbidity, are excellent in color reproducibility and can give a high density.

EXAMPLE 2

An undercoated triacetyl cellulose support was used, and single layer light-sensitive materials 101 to 129 having the following structure for evaluation were prepared by using couplers M-1 to M-15, M-22 to M-26, M-29, M-34, M-43 and M-45 and Comparative couplers a, b, c and d as indicated in Table 16. The same comparative couplers a, b and c as those used in Example 1 were used. Comparative coupler (d) was the following compound.

Comparative coupler (d) (coupler described in JP-A-3-48845)

Preparation of coating solution for emulsion layer

There was dissolved 1.85 mmol of coupler in 10 cc of ethyl acetate and 2 g of tris(2-ethylhexyl) phosphate (solvent). The resulting solution was emulsified and dispersed in 33 g of a 14% aqueous gelatin solution containing 3 cc of a 10% sodium dodecylbenzenesulfonate solution. Separately, a silver chlorobromide (silver bromide content: 70 mol%) emulsion was prepared and sulfur-sensitized. The emulsion and the emulsified dispersion prepared above were mixed and dissolved, and a coating solution was prepared so as to give the following composition. Sodium salt of 1-oxy-3,5-di-chloro-s-triazine was used as a hardening agent.

Layer structure

Samples used in this experiment had the following layer structure (numerals being coating weight per m²).

Support

Triacetyl cellulose support

| Emulsion layer | |
|---|---|
| The above silver chlorobromide-emulsion | 4.0 mmol |
| Coupler | 1.0 mmol |
| Tris(2-ethylhexyl) phosphate | 1.08 g |

-continued

| | |
|---|---|
| Gelatin protective layer | 5.2 g |
| Gelatin | 1.3 g |
| Acrylic-modified copolymer of polyvinyl alcohol (a degree of modification: 17%) | 0.17 g |
| Liquid paraffin | 0.03 g |

Samples were imagewise exposed to light through an optical wedge and processed in the following processing stage.

| Processing stage | Temperature (°C.) | Time (min) |
|---|---|---|
| Color Development | 33 | 2 |
| Bleaching-fixing | 33 | 1.5 |
| Rinse | 33 | 3 |

| Composition of processing solution | |
|---|---|
| Color developing solution | |
| Distilled water | 800 ml |
| Triethanolamine | 8.1 g |
| Diethylhydroxylamine | 4.2 g |
| Potassium bromide | 0.6 g |
| Sodium hydrogencarbonate | 3.9 g |
| Sodium sulfite | 0.13 g |
| N-Ethyl-N-(β-methanesulfonamido-ethyl)-3-methyl-4-aminoaniline sulfate | 5.0 g |
| Potassium carbonate | 18.7 g |
| Water to make | 1000 ml |
| pH | 10.25 |
| Bleaching-fixing solution | |
| Distilled water | 400 ml |
| Ammonium thiosulfate (700 g/l) | 150 ml |
| Sodium sulfate | 18.0 g |
| Ammonium ethylenediaminetetraacetato ferrate | 55.0 g |
| Disodium ethylenediaminetetraacetate | 5.0 g |
| Water to make | 1000 ml |
| pH | 6.70 |

The visible spectral absorption spectrum of each of the thus-obtained samples 101 to 129 was measured at a dye concentration which gave an absorbance of 1.0. In the same manner as in Example 1, λmax, λ/2, Δλ$_1$ and Δλ$_2$ were determined. The results are shown in Table 16.

TABLE 16

| Sample No. | Coupler No. | Maximum absorption wavelength (λmax) (nm) | λ½ (nm) | Δλ$_1$ (nm) | Δλ$_2$ (nm) |
|---|---|---|---|---|---|
| 101 | M-1 | 548.0 | 73.1 | 95.3 | 54.5 |
| 102 | M-2 | 548.0 | 73.2 | 95.3 | 54.7 |
| 103 | M-3 | 547.0 | 74.0 | 96.1 | 54.1 |
| 104 | M-4 | 547.0 | 75.0 | 95.9 | 54.2 |
| 105 | M-5 | 549.2 | 75.0 | 97.3 | 56.1 |
| 106 | M-6 | 551.0 | 75.0 | 96.2 | 56.4 |
| 107 | M-7 | 547.0 | 74.5 | 96.7 | 53.2 |
| 108 | M-8 | 552.0 | 74.9 | 97.7 | 54.7 |
| 109 | M-9 | 549.0 | 74.9 | 96.3 | 53.7 |
| 110 | M-10 | 549.1 | 75.0 | 97.4 | 56.1 |
| 111 | M-11 | 550.0 | 75.0 | 97.3 | 54.3 |
| 112 | M-12 | 549.1 | 75.0 | 96.1 | 56.0 |
| 113 | M-13 | 549.3 | 74.9 | 96.3 | 53.7 |
| 114 | M-14 | 549.4 | 74.5 | 95.1 | 54.2 |
| 115 | M-15 | 546.8 | 74.4 | 95.0 | 53.8 |
| 116 | M-22 | 549.9 | 75.0 | 97.3 | 53.5 |
| 117 | M-23 | 550.0 | 75.0 | 97.2 | 56.5 |
| 118 | M-24 | 549.8 | 75.0 | 97.1 | 55.1 |
| 119 | M-25 | 550.0 | 75.0 | 98.0 | 55.1 |
| 120 | M-26 | 549.8 | 75.0 | 97.0 | 54.6 |
| 121 | M-29 | 550.0 | 75.0 | 97.3 | 54.1 |

TABLE 16-continued

| Sample No. | Coupler No. | Maximum absorption wavelength (λmax) (nm) | λ½ (nm) | Δλ$_1$ (nm) | Δλ$_2$ (nm) |
|---|---|---|---|---|---|
| 123 | M-34 | 549.1 | 74.8 | 96.1 | 54.2 |
| 124 | M-43 | 547.0 | 74.4 | 95.8 | 54.1 |
| 125 | M-45 | 547.0 | 74.5 | 95.8 | 54.2 |
| 126 | Comparative coupler a | 552.3 | 75.0 | 98.3 | 60.6 |
| 127 | Comparative coupler b | 549.0 | 75.1 | 98.6 | 61.1 |
| 128 | Comparative coupler c | 549.1 | 75.1 | 98.8 | 61.5 |
| 129 | Comparative coupler d | 544.2 | 75.0 | 98.2 | 58.3 |

It could be confirmed that the couplers of the present invention are excellent couplers which can form dyes which have small Δλ$_2$ value, are excellent in the cut of the foot on the long wavelength side and scarcely cause color turbidity as in Example 1.

EXAMPLE 3

Both sides of a paper support were laminated with polyethylene. The surface of the polyethylene-laminated paper support was subjected to a corona discharge treatment. A gelation undercoat layer containing sodium dodecylbenzenesulfonate was provided thereon, and various photographic constituent layers were coated thereon to prepare a multi-layer color photographic paper having the following layer structure (sample 201). Coating solutions were prepared in the following manner.

Preparation of coating solution for third layer 5.10 g of magenta coupler M-2 of the present invention, 21.0 g of the dye image stabilizer (Cpd-5), 12.0 g of dye image stabilizer (Cpd-2), 6.0 g of dye image stabilizer (Cpd-6), 24.0 g of dye image stabilizer (Cpd-8), 21.0 g of dye image stabilizer (Cpd-1), 9.0 g of dye image stabilizer (Cpd-7) and 10 g of sodium dodecylbenzenesulfonate were dissolved in 180 g of solvent (Solv-3) and 150 cc of ethyl acetate. The resulting solution was emulsified and dispersed in 600 g of a 18% aqueous solution of gelatin, and water was then added thereto to make the whole amount 2,000 g, thus preparing an emulsified dispersion A.

Separately, a silver chlorobromide emulsion B (cubic; a 1:3 (by mol of Ag) mixture of a larger-size emulsion B having a mean grain size of 0.55 μm and a smaller-size emulsion B having a mean grain size of 0.39 μm; a coefficient of variation in a grain size distribution: 0.10 and 0.08, respectively; 0.8 mol % of silver bromide being localized on a part of the surface of the grain in each size emulsion) was prepared. The following sensitizing dye C ($4.0 \times 10^{-4}$ mol was added to the larger-size emulsion, and $5.6 \times 10^{31\ 4}$ mol was added to the smaller-size emulsion, each amount being per mol of silver halide) and the following sensitizing dye D ($7.0 \times 10^{-5}$ mol was added to the larger-size emulsion, and $1.0 \times 10^{-5}$ mol was added to the smaller-size emulsion, each amount being per mol of silver halide) were added to the emulsion. The chemical ripening of the emulsion was carried out by adding a sulfur sensitizing agent and a gold sensitizing agent. The above emulsified dispersion A and the silver chlorobromide emulsion B were mixed and dissolved, and a coating solution for the third layer was prepared so as to give the following composition.

Coating solutions for the first layer, the second layer and the fifth layer through the seventh layer were prepared in the same manner as described above.

Sodium salt of 1-oxy-3,5-dichloro-s-triazine was used as a hardening agent for gelatin in each layer. Cpd-14 and Cpd-15 were added to each layer in such an amount as to give 25.0 mg/m² and 50 mg/m² in total, respectively.

The following spectral sensitizing dyes were used in the silver chlorobromide emulsion of each light-sensitive emulsion layer.

Blue-sensitive emulsion layer

Sensitizing dye A

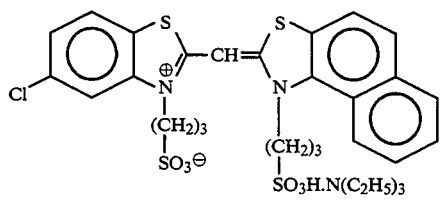

Sensitizing Dye B

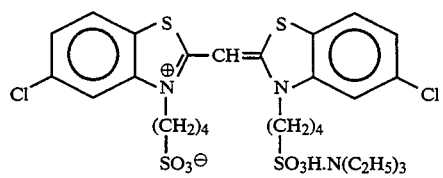

(2.0×10⁻⁴ mol of each of the dyes being added to the larger-size emulsion, and 2.5×10⁻⁴ mol of each of the dyes being added to the smaller-size emulsion, each amount being per mol of silver halide)

Green-sensitive emulsion layer

Sensitizing dye C

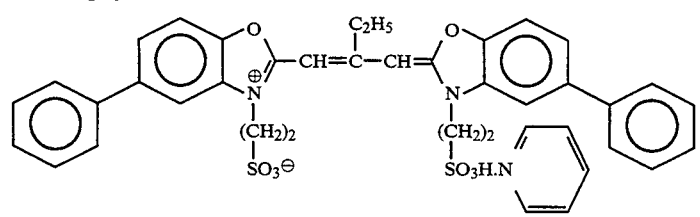

4.0×10⁻⁴ mol being added to the larger-size emulsion, and 5.6×10⁻⁴ mol being added to the smaller-size emulsion, each amount being per mol of silver halide)

Sensitizing dye D

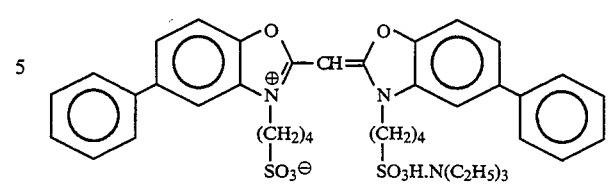

(7.0×10⁻⁵ mol being added to the larger-size emulsion, and 1.0×10⁻⁵ mol being added to the smaller-size emulsion, each amount being per mol of silver halide)

Red-Sensitive emulsion layer

Sensitizing dye E

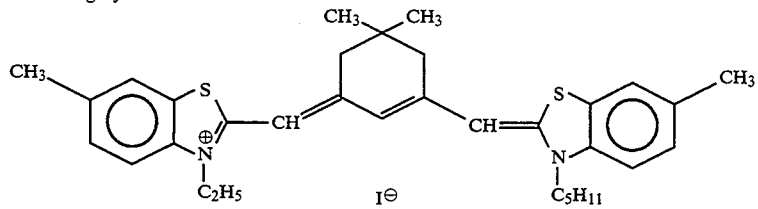

(9.033 10⁻⁴ mol being added to the larger-size emulsion, and 1.1×10⁻⁴ mol being added to the smaller-size emulsion, each amount being per mol of silver halide) Further, 2.6×10⁻³ mol of the following compound per mol of silver halide was added

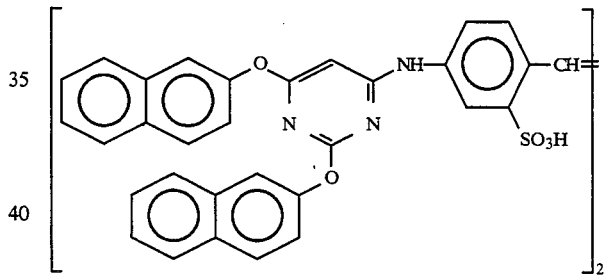

Further, 8.5×10⁻⁶ mol, 7.7×10⁻⁴ mol and 2.5×10⁻⁴ mol of 1-(5-methylureidophenyl)-5-mercaptotetrazole were added to the blue-sensitive emulsion layer, the green-sensitive emulsion layer and the red-sensitive emulsion layer, respectively, each amount being per mol of silver halide.

Furthermore, 1×10⁻⁴ mol and 2×10⁻⁴ mol of 4-hydroxy-6-methyl-1,3,3a,7-tetrazaindene were added to the blue-sensitive emulsion layer and the green-sensitive emulsion layer, respectively, each amount being per mol of silver halide.

The following dyes (parenthesized numeral being coating weight) were added to the emulsion layers to prevent irradiation.

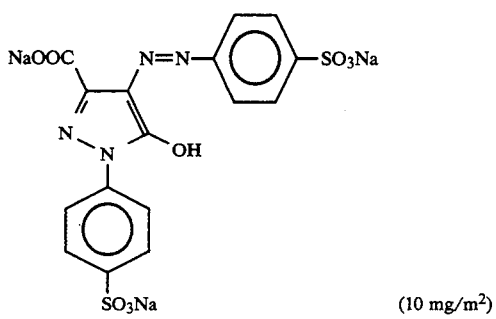

(10 mg/m²)

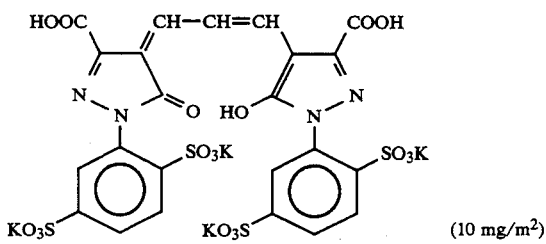

(10 mg/m²)

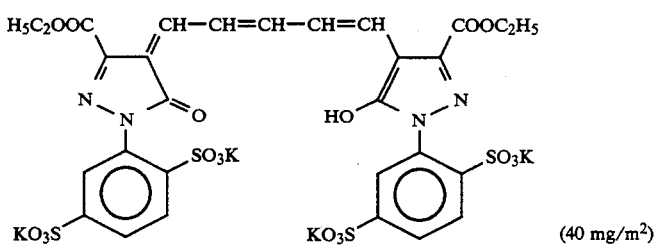

(40 mg/m²)

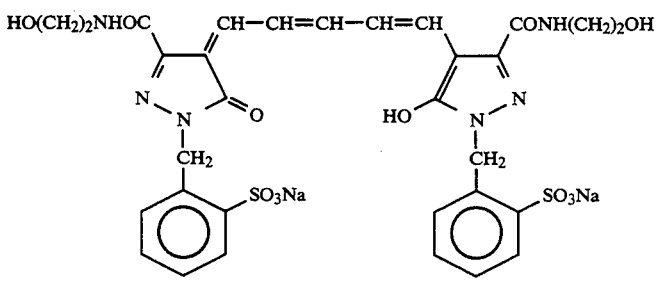

(20 mg/m²)

Layer structure

Each layer had the following composition. Numerals represent coating weight (g/m²). The amount of silver halide emulsion is represented by coating weight in terms of silver.

Support
  Polyethylene-laminated paper
  (Polyethylene on the first layer side contained white pigment (TiO₂) and bluish dye (ultra-marine))

| First layer (blue-sensitive emulsion layer) | |
|---|---|
| Silver chlorobromide emulsion (cubic; a 3:7 (by mol of Ag) mixture of a larger-size emulsion A having a mean grain size of 0.88 μm and a smaller-size emulsion A having a mean grain size of 0.70 μm; a coefficient of variation in a grain size distribution: 0.08 and 0.10, respectively; 0.3 mol % of silver bromide being localized on a part of the surface of the grain in each size emulsion) | 0.27 |
| Gelatin | 1.36 |
| Yellow coupler (ExY) | 0.67 |
| Dye image stabilizer (Cpd-1) | 0.08 |
| Dye image stabilizer (Cpd-2) | 0.04 |
| Dye image stabilizer (Cpd-3) | 0.08 |
| Solvent (Solv-1) | 0.12 |
| Solvent (Solv-2) | 0.12 |
| Second layer (color mixing inhibiting layer) | |
| Gelatin | 1.10 |
| Color mixing inhibitor (Cpd-4) | 0.08 |
| Solvent (Solv-2) | 0.53 |
| Dye image stabilizer (Cpd-7) | 0.03 |
| Third layer (green-sensitive emulsion layer) | |
| The above-described silver chlorobromide emulsion B | 0.13 |
| Gelatin | 1.45 |
| Magenta Coupler (M-2) | 0.17 |
| Dye image stabilizer (Cpd-5) | 0.07 |
| Dye image stabilizer (Cpd-2) | 0.04 |
| Dye image stabilizer (Cpd-6) | 0.02 |
| Dye image stabilizer (Cpd-8) | 0.08 |
| Dye image stabilizer (Cpd-1) | 0.07 |
| Dye image stabilizer (Cpd-7) | 0.03 |

-continued

| | |
|---|---|
| Solvent (Solv-3) | 0.60 |
| Fourth layer (color mixing inhibiting layer) | |
| Gelatin | 0.70 |
| Color mixing inhibitor (Cpd-4) | 0.05 |
| Solvent (Solv-2) | 0.37 |
| Dye image stabilizer (Cpd-7) | 0.02 |
| Fifth layer (red-sensitive emulsion layer) | |
| Silver chlorobromide emulsion (cubic; a 1:4 (by mol of Ag) mixture of a larger-size emulsion C having a mean grain size of 0.50 μm and a smaller-size emulsion C having a mean grain size of 0.4 μm; a coefficient of variation in a grain size distribution: 0.09 and 0.11, respectively; 0.8 mol % of silver bromide being localized on a part of the surface of the grain in each size emulsion) | 0.20 |
| Gelatin | 0.90 |
| Cyan coupler (ExC) | 0.33 |
| Ultraviolet light absorber (Uv-2) | 0.18 |
| Dye image stabilizer (Cpd-8) | 0.01 |

-continued

| | |
|---|---|
| Dye image stabilizer (Cpd-10) | 0.01 |
| Dye image stabilizer (Cpd-11) | 0.01 |
| Solvent (Solv-4) | 0.22 |
| Dye image stabilizer (Cpd-8) | 0.01 |
| Dye image stabilizer (Cpd-6) | 0.01 |
| Solvent (Solv-1) | 0.01 |
| Dye image stabilizer (Cpd-1) | 0.33 |
| Sixth layer (ultraviolet light absorbing layer) | |
| Gelatin | 0.55 |
| Ultraviolet light absorber (Uv-1) | 0.38 |
| Dye image stabilizer (Cpd-12) | 0.15 |
| Dye image stabilizer (Cpd-5) | 0.02 |
| Seventh layer (protective layer) | |
| Gelatin | 1.33 |
| Acrylic-modified copolymer of polyvinyl alcohol (a degree of modification: 17%) | 0.05 |
| Liquid paraffin | 0.02 |
| Dye image stabilizer (Cpd-13) | 0.01 |

Compounds used in the above layers are the following compounds.

(ExY) Yellow Coupler

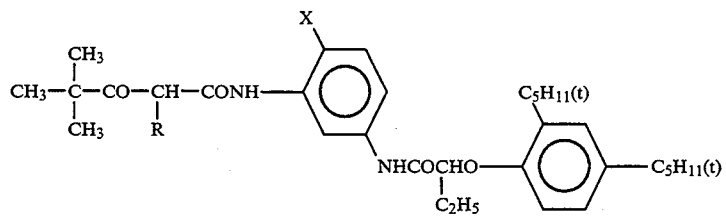

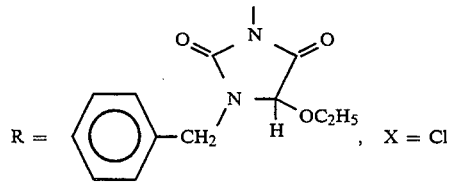

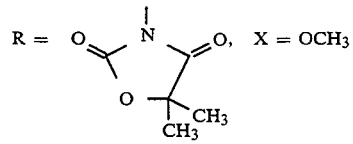

1:1 mixture (by mol)

(ExM) Magenta Coupler

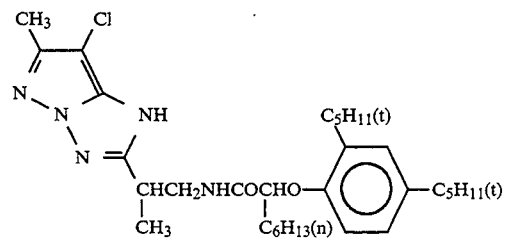

(ExC) Cyan Coupler

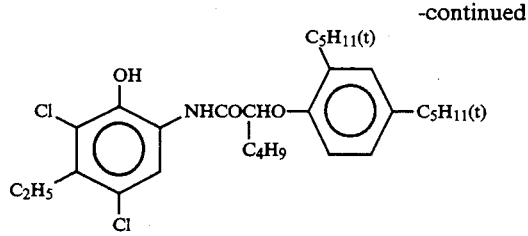
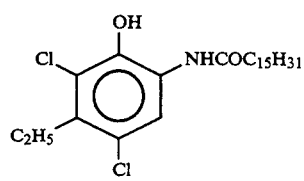
3:7 mixture (by mol)
(Cpd-1) Dye image stabilizer
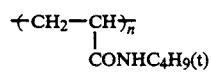
Average mol. wt. 60,000
(Cpd-2) Dye image stabilizer
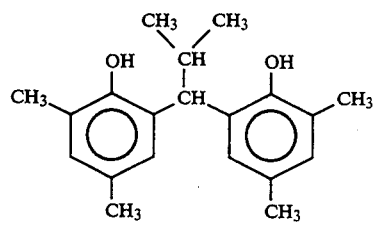
(Cpd-3) Dye image stabilizer
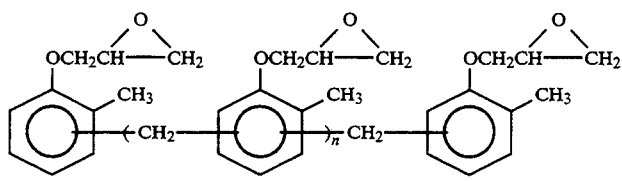
n = 7 to 8 (mean value)
(Cpd-4) Color mixing inhibitor
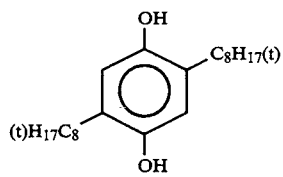
(Cpd-5) Dye image stabilizer
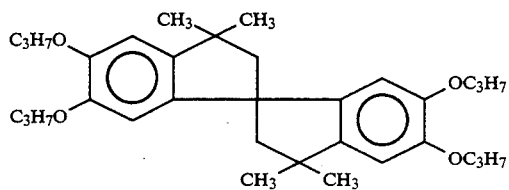
(Cpd-6) Dye image stabilizer -continued
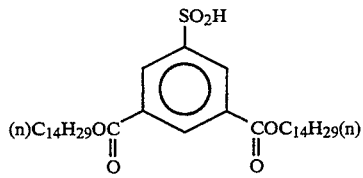
(Cpd-7) Dye image stabilizer
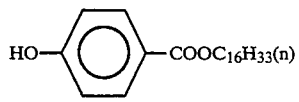
(Cpd-8) Dye image stabilizer
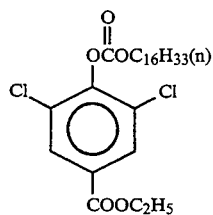
(Cpd-9) Dye image stabilizer
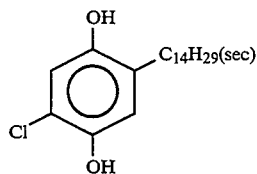
(Cpd-10) Dye image stabilizer
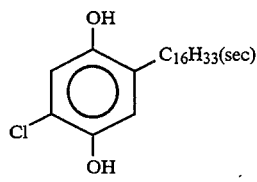
(Cpd-11) Dye image stabilizer
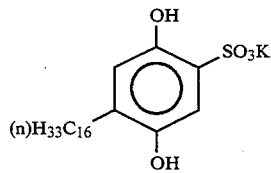
(Cpd-12) Dye image stabilizer
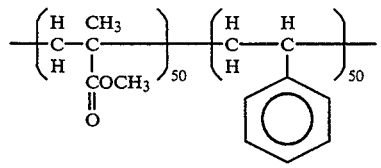
average mol. wt. about $6.0 \times 10^4$
(Cpd-13) Dye image stabilizer
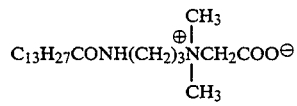

-continued
(Cpd-14) Antiseptic
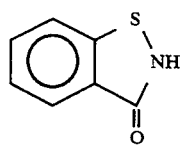
(Cpd-15) Antiseptic
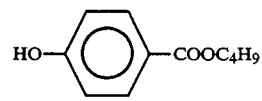
(UV-1) Ultraviolet light absorber
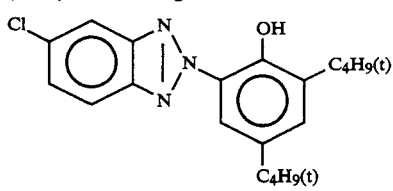
(1)
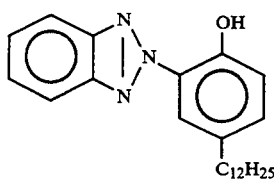
(2)
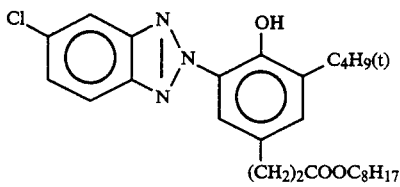
(3)
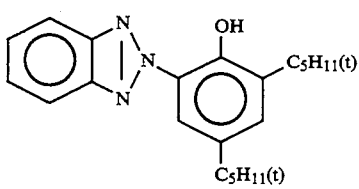
(4)
1:5:10:5 (by weight) mixture of (1), (2), (3) and (4)
(UV-2) Ultraviolet light absorber
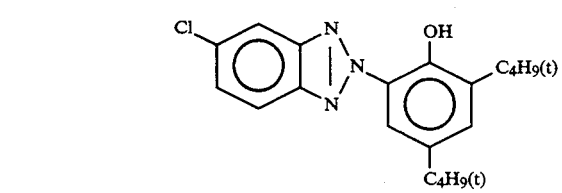
(1)
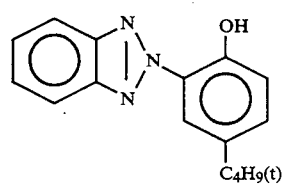
(2)

-continued

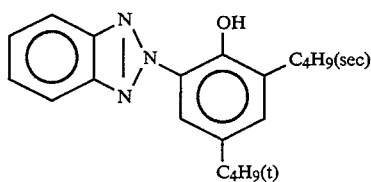

1:2:2 (by weight) mixture of (1), (2) and (3)

(Solv-1) Solvent

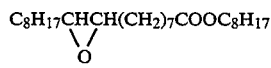

(Solv-2) Solvent

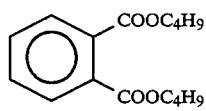

(Solv-3) Solvent

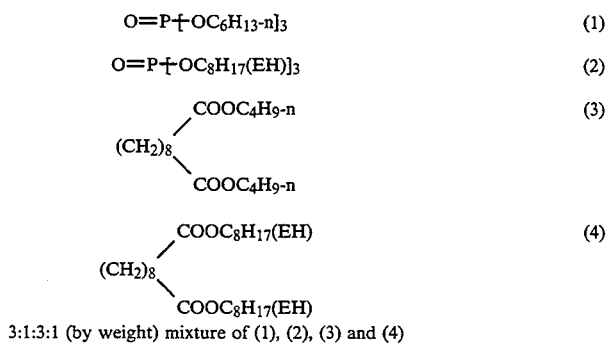

3:1:3:1 (by weight) mixture of (1), (2), (3) and (4)

(Solv-4) Solvent

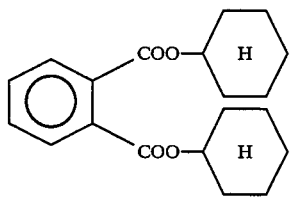

Samples 202 to 236 were prepared in the same manner as in the preparation of the sample 201 except that an equimolar amount of each of couplers indicated in Table 17 was used in place of the coupler M-2 of the present invention.

First, the sample 201 was subjected to gradation exposure through a three-color separation filter for sensitometry by using a sensitometer (FWH type, color temperature of light source: 3200° K., manufactured by Fuji Photo Film Co., Ltd.). The exposure time was 0.1 second, and exposure was conducted so as to give an exposure amount of 250 CMS.

The standard sample was subjected to continuous processing by using a paper processor, the following processing stage and the following processing solutions having the following compositions to prepare a development processing solution which was brought into a running equilibrium state.

| Processing stage | Temperature (°C.) | Time (sec.) | Replenisher* (ml) | Tank capacity (l) |
|---|---|---|---|---|
| Color development | 35 | 45 | 161 | 17 |
| Blixing | 30–35 | 45 | 215 | 17 |
| Rinse | 30 | 90 | 350 | 10 |
| Drying | 70–80 | 60 | | |

*Replenishment rate being per m² of the light-sensitive material.

Each processing solution had the following composition.

| Color developing solution | Tank Solution | Replenisher |
|---|---|---|
| Water | 800 ml | 800 ml |
| Ethylenediamine-N,N,N',N'-tetramethylenephosphonic acid | 1.5 g | 2.0 g |
| Potassium bromide | 0.015 g | — |
| Triethanolamine | 8.0 g | 12.0 g |
| Sodium chloride | 1.4 g | — |
| Potassium carbonate | 25 g | 25 g |

-continued

| | | |
|---|---|---|
| N-Ethyl-N-(β-methanesulfon-amidoethyl)-3-methyl-4-amino-aniline sulfate | 5.0 g | 7.0 g |
| N,N-Bis(carboxymethyl)-hydrazine | 4.0 g | 5.0 g |
| Fluorescent brightener (WHITEX 4B manufactured by Sumitomo Chemical Co., Ltd.) | 1.0 g | 2.0 g |
| Water to make | 1000 ml | 1000 ml |
| pH (25° C.) | 10.05 | 10.45 |

Blixing solution

Tank solution and replenisher being the same.

| | |
|---|---|
| Water | 400 ml |
| Ammonium thiosulfate (700 g/l) | 100 ml |
| Sodium sulfite | 17 g |
| Ammonium ethylenediaminetetraacetato ferrate | 55 g |
| Disodium Ethylenediaminetetraacetate | 5 g |
| Ammonium bromide | 40 g |
| Water to make | 1000 ml |
| pH (25° C.) | 6.0 |

Rinsing solution
Tank solution and replenisher being the same.
Ion-exchanged solution
(The concentration of each of calcium ion and magnesium ion was reduced to not higher than 3 ppm)

Evaluation of a lowering in color developability caused by the back contamination of the ingredients in the bleaching-fixing solution was made in the following manner.

A color developing solution (B) was prepared by adding 1.0 ml of the bleaching-fixing solution to one liter of the color developing solution (A) brought into the equilibrium state described above. The photographic characteristic curve of a magenta dye image obtained by conducting processing with the color developing solution (A) free from the bleaching-fixing solution was compared with that of a magenta dye image obtained by conducting processing with the color developing solution (B). Comparison was made in the following manner. There was determined a density D of each sample obtained by conducting processing with the color developing solution (B) in an exposure amount giving a density of 1.0 when processed with the color developing solution (A). A degree of photographic fluctuation was represented by a difference in density ($\Delta D = 1.0$-D). Accordingly, a smaller $\Delta D$ value means that photographic fluctuation caused by back contamination is smaller.

TABLE 17

| Sample No. | Coupler | $\Delta D(D^0 = 1.0)$ | Remarks |
|---|---|---|---|
| 201 | M-2 | 0.03 | Invention |
| 202 | M-6 | 0.04 | " |
| 203 | M-9 | 0.02 | " |
| 204 | M-22 | 0.02 | " |
| 205 | M-24 | 0.03 | " |
| 206 | M-25 | 0.02 | " |
| 207 | M-43 | 0.01 | " |
| 208 | M-44 | 0.01 | " |
| 209 | M-45 | 0.01 | " |
| 210 | M-46 | 0.00 | " |
| 211 | M-47 | 0.02 | " |
| 212 | M-48 | 0.01 | " |
| 213 | M-49 | 0.01 | " |
| 214 | M-50 | 0.01 | " |
| 215 | M-51 | 0.00 | " |
| 216 | M-52 | 0.01 | " |
| 217 | M-53 | 0.01 | " |
| 218 | M-54 | 0.01 | " |
| 219 | M-55 | 0.01 | " |

TABLE 17-continued

| Sample No. | Coupler | $\Delta D(D^0 = 1.0)$ | Remarks |
|---|---|---|---|
| 220 | M-56 | 0.01 | " |
| 221 | M-57 | 0.01 | " |
| 222 | M-58 | 0.01 | Invention |
| 223 | M-59 | 0.02 | " |
| 224 | M-60 | 0.00 | " |
| 225 | M-61 | 0.02 | " |
| 226 | M-62 | 0.01 | " |
| 227 | M-63 | 0.00 | " |
| 228 | M-64 | 0.00 | " |
| 229 | M-65 | 0.01 | " |
| 230 | M-66 | 0.02 | " |
| 231 | M-67 | 0.01 | " |
| 232 | Comparative coupler (a) | 0.23 | Comparison |
| 233 | Comparative coupler (b) | 0.20 | " |
| 234 | Comparative coupler (c) | 0.18 | " |
| 235 | Comparative coupler (d) | −0.09 | " |
| 236 | Comparative coupler (e) | −0.11 | " |

The same comparative couplers (a), (b) and (c) as those used in Example 1 were used.

The same comparative coupler (d) as that used in Example 2 was used.

Comparative coupler (e)
(coupler described in U.S. Pat. No. 4,639,415)

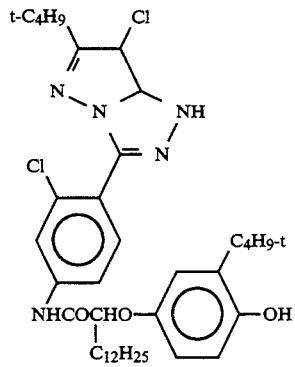

The above results show that when comparative samples are processed with a developing solution back-contaminated with the ingredients of a blixing-fixing solution, a remarkable lowering in color developability is caused, while the samples of the present invention do substantially experience a lowering in color developability.

Namely, comparative samples 232, 233 and 234 possess low contrast on the photographic characteristic curve and a lowering in sensitivity by back contamination, and comparative sample 235 containing comparative coupler (d) and comparative sample 236 containing comparative coupler (e) possess high contrast and a rise in sensitivity, while the samples of the present invention do substantially not cause any fluctuation. Accordingly, it can be seen that according to the present invention, properties with regard to back contamination can be greatly improved.

Further, when the samples 201 to 231 were processed with the color developing solution (A), maximum color density was at least 2.0, while the samples 235 and 236 were processed with the color developing solution (A), maximum color density was 1.83 and 1.60, and color developability was low.

Furthermore, it was confirmed that the samples of the present invention were excellent in hue as in Example 2.

EXAMPLE 4

The following layers having the following compositions were coated on an undercoated cellulose triacetate support to prepare a multi-layer light-sensitive material as sample 301.

Following abbreviations for principal ingredients used in the following layers are used for brevity's sake.

ExC: cyan coupler
ExM: magenta coupler
ExY: yellow coupler
ExS: sensitizing dye
UV: ultraviolet light absorber
HBS: high-boiling organic solvent
H: hardening agent for gelatin Numerals represent coating weight (g/m$^2$). The amount of silver halide emulsion is represented by coating weight in terms of silver. The amount of sensitizing dye is represented by moles per one mole of silver halide in the same layer.

| First layer (antihalation layer) | |
|---|---|
| Black colloidal silver (in terms of silver) | 0.18 |
| Gelatin | 1.40 |
| ExM-1 | 0.18 |
| ExF-1 | $2.0 \times 10^{-3}$ |
| HBS-1 | 0.20 |
| Second layer (interlayer) | |
| Emulsion G (in terms of silver) | 0.065 |
| 2,5-Di-t-pentadecylhydroquinone | 0.18 |
| ExC-2 | 0.020 |
| UV-1 | 0.060 |
| UV-2 | 0.080 |
| UV-3 | 0.10 |
| HBS-1 | 0.10 |
| HBS-2 | 0.020 |
| Gelatin | 1.04 |
| Third layer (low-sensitivity red-sensitive emulsion layer) | |
| Emulsion A (in terms of silver) | 0.25 |
| Emulsion B (in terms of silver) | 0.25 |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |
| ExC-4 | 0.10 |
| ExC-5 | 0.020 |
| ExC-7 | 0.0050 |
| ExC-8 | 0.010 |
| Cpd-2 | 0.025 |
| HBS-1 | 0.10 |
| Gelatin | 0.87 |
| Fourth layer (intermediate-sensitivity red-sensitive emulsion layer) | |
| Emulsion D (in terms of silver) | 0.70 |
| ExS-1 | $3.5 \times 10^{-4}$ |
| ExS-2 | $1.6 \times 10^{-5}$ |
| ExS-3 | $5.1 \times 10^{-4}$ |
| ExC-1 | 0.13 |
| ExC-2 | 0.060 |
| ExC-3 | 0.0070 |
| ExC-4 | 0.090 |
| ExC-5 | 0.025 |
| ExC-7 | 0.0010 |
| ExC-8 | 0.0070 |
| Cpd-2 | 0.023 |
| HBS-1 | 0.10 |
| Gelatin | 0.75 |
| Fifth layer (high-sensitivity red-sensitive emulsion layer) | |
| Emulsion E (in terms of silver) | 1.40 |
| ExS-1 | $2.4 \times 10^{-4}$ |
| ExS-2 | $1.0 \times 10^{-4}$ |
| ExS-3 | $3.4 \times 10^{-4}$ |
| ExC-1 | 0.12 |
| ExC-3 | 0.045 |
| ExC-6 | 0.020 |
| ExC-8 | 0.025 |
| Cpd-2 | 0.05 |
| HBS-1 | 0.22 |
| HBS-2 | 0.10 |
| Gelatin | 1.20 |
| Sixth layer (interlayer) | |
| Cpd-1 | 0.10 |
| HBS-1 | 0.50 |
| Gelatin | 1.10 |
| Seventh layer (low-sensitivity green-sensitive emulsion layer) | |
| Emulsion C (in terms of silver) | 0.35 |
| ExS-4 | $3.0 \times 10^{-5}$ |
| ExS-5 | $2.1 \times 10^{-4}$ |
| ExS-6 | $8.0 \times 10^{-4}$ |
| ExM-1 | 0.005 |
| ExM-2 | 0.40 |
| ExM-3 | 0.03 |
| ExY-1 | 0.015 |
| HBS-1 | 0.30 |
| HBS-3 | 0.010 |
| Gelatin | 0.73 |
| Eighth layer (intermediate-sensitivity green-sensitive emulsion layer) | |
| Emulsion D (in terms of silver) | 0.80 |
| ExS-4 | $3.2 \times 10^{-5}$ |
| ExS-5 | $2.2 \times 10^{-4}$ |
| ExS-6 | $8.4 \times 10^{-4}$ |
| ExM-2 | 0.13 |
| ExM-3 | 0.030 |
| ExY-1 | 0.018 |
| HBS-1 | 0.16 |
| HBS-3 | $8.0 \times 10^{-3}$ |
| Gelatin | 0.90 |
| Ninth layer (high-sensitivity green-sensitive emulsion layer) | |
| Emulsion E (in terms of silver) | 1.25 |
| ExS-4 | $3.7 \times 10^{-5}$ |
| ExS-5 | $8.1 \times 10^{-5}$ |
| ExS-6 | $3.2 \times 10^{-4}$ |
| ExC-1 | 0.010 |
| ExM-1 | 0.030 |
| ExM-4 | 0.040 |
| ExM-5 | 0.019 |
| Cpd-3 | 0.040 |
| HBS-1 | 0.25 |
| HBS-2 | 0.10 |
| Gelatin | 1.44 |
| Tenth layer (yellow filter layer) | |
| Yellow colloidal silver (in terms of silver) | 0.030 |
| Cpd-1 | 0.16 |
| HBS-1 | 0.60 |
| Gelatin | 0.60 |
| Eleventh layer (low-sensitivity blue-sensitive emulsion layer) | |
| Emulsion C (in terms of silver) | 0.18 |
| ExS-7 | $8.6 \times 10^{-4}$ |
| ExY-1 | 0.020 |
| ExY-2 | 0.22 |
| ExY-3 | 0.50 |
| ExY-4 | 0.020 |
| HBS-1 | 0.28 |
| Gelatin | 1.10 |
| Twelfth layer (intermediate-sensitivity blue-sensitive emulsion layer) | |
| Emulsion D (in terms of silver) | 0.40 |
| ExS-7 | $7.4 \times 10^{-4}$ |
| ExC-7 | $7.0 \times 10^{-3}$ |
| ExY-2 | 0.050 |
| ExY-3 | 0.10 |
| HBS-1 | 0.050 |
| Gelatin | 0.78 |

| Thirteenth layer (high-sensitivity blue-sensitive emulsion layer) | |
|---|---|
| Emulsion F (in terms of silver) | 1.00 |
| ExS-7 | $4.0 \times 10^{-4}$ |
| ExY-2 | 0.10 |
| ExY-3 | 0.10 |
| HBS-1 | 0.070 |
| Gelatin | 0.86 |
| Fourteenth layer (first protective layer) | |
| Emulsion G (in terms of silver) | 0.20 |
| UV-4 | 0.11 |
| UV-5 | 0.17 |
| HBS-1 | $5.0 \times 10^{-2}$ |
| Gelatin | 1.00 |
| Fifteenth layer (second protective layer) | |
| H-1 | 0.40 |
| B-1 (diameter: 1.7 μm) | $5.0 \times 10^{-2}$ |
| B-2 (diameter: 1.7 μm) | 0.10 |
| B-3 | 0.10 |
| S-1 | 0.20 |
| Gelatin | 1.20 |

Further, each layer contained W-1 to W-3, B-4 to B-6, F-1 to F-17, iron salt, lead salt, gold salt, platinum salt, iridium salt and rhodium salt to improve preservability, processability, pressure resistance, antifungal and antibacterial properties, antistatic properties and coatability.

TABLE 18

| Emulsion | Average AgI content (%) | Mean grain size (μm) | Coefficient of variation in grain size distribution (%) | Ratio of diameter/ thickness | Ratio of amount of silver [core/intermediate/shell] (AgI content) | Grain structure/form |
|---|---|---|---|---|---|---|
| A | 4.0 | 0.15 | 27 | 1 | [1/3] (13/1) | double structural octahedral grains |
| B | 8.9 | 0.70 | 14 | 1 | [3/7] (25/2) | double structural octahedral grains |
| C | 2.0 | 0.55 | 25 | 7 | — | uniform structural tabular grains |
| D | 9.0 | 0.65 | 25 | 6 | [12/59/29] (0/11/8) | triple structural tabular grains |
| E | 9.0 | 0.85 | 23 | 5 | [8/59/33] (0/11/8) | triple structural tabular grains |
| F | 14.5 | 1.25 | 25 | 3 | [37/63] (34/4) | double structural platy grains |
| G | 1.0 | 0.07 | 15 | 1 | — | uniform structural fine grains |

In Table 18, (1) Emulsions A to F were reduction-sensitized during the preparation of grains by using thiourea dioxide and thiosulfonic acid according to Examples of JP-A-2-191938.

(2) Emulsions A to F were subjected to gold sensitization, sulfur sensitization and selenium sensitization in the presence of sodium thiocyanate and spectral sensitizing dyes described in each light-sensitive layer according to Examples of JP-A-3-237450.

(3) Tabular grains were prepared by using low-molecular gelatin according to Examples of JP-A-1-158426.

(4) Tabular grains and normal crystal grains having a grain structure showed that dislocation lines as described in JP-A-3-237450 were observed through high-pressure electron microscope.

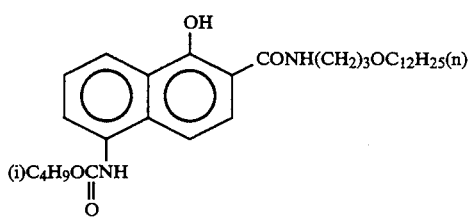

ExC-1

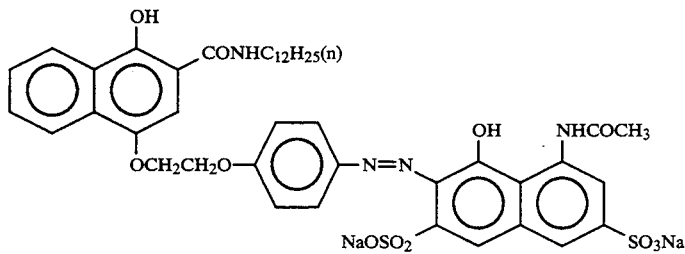

ExC-2

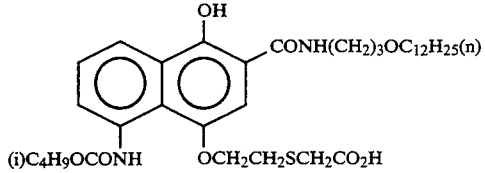

ExC-3

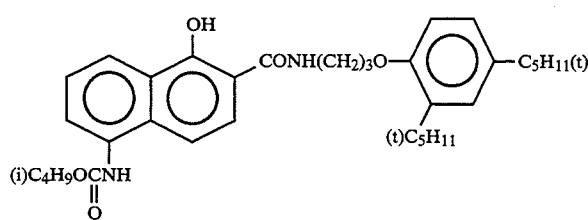
ExC-4
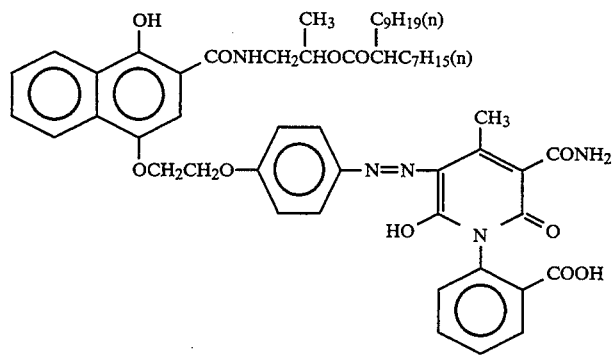
ExC-5
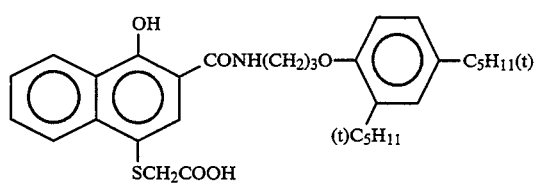
ExC-6
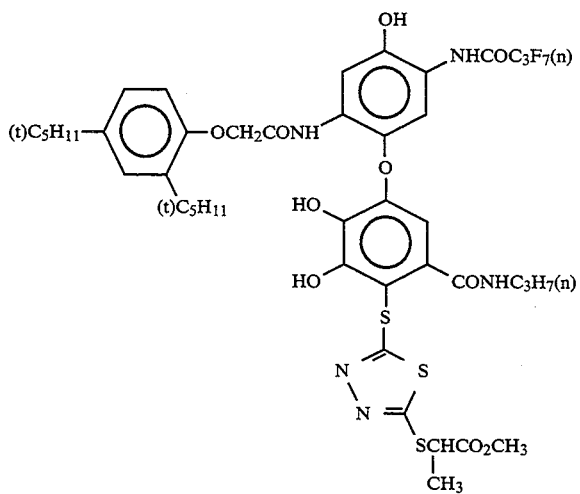
ExC-7
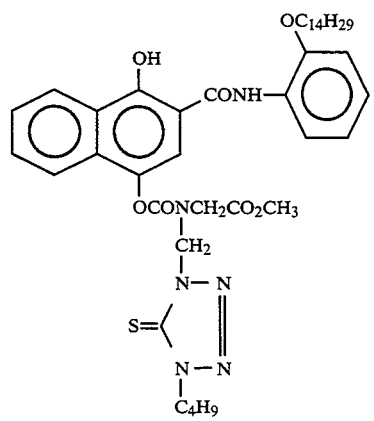
ExC-8

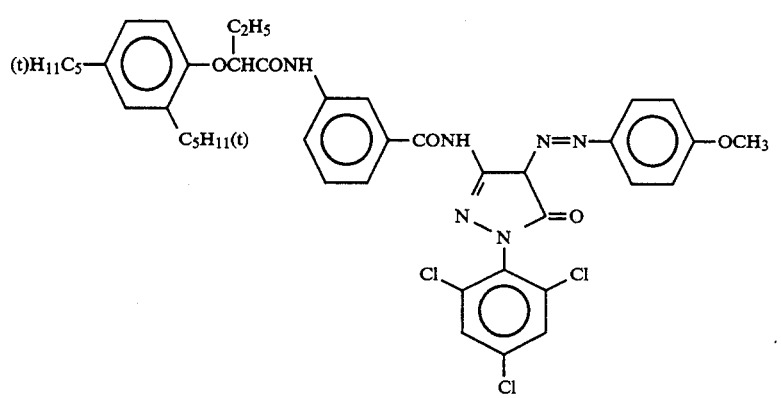
ExM-1
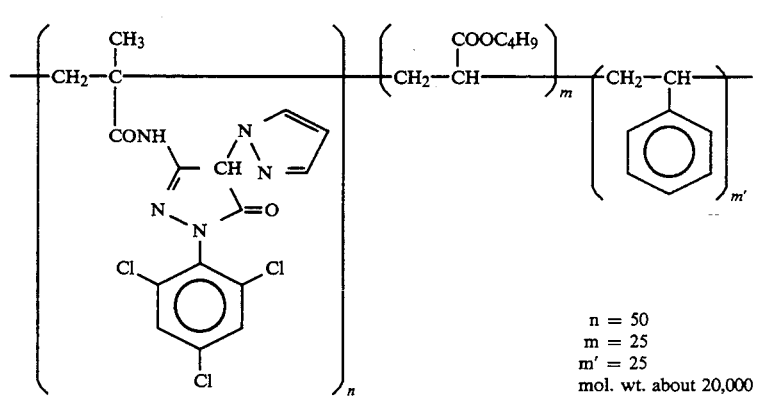
ExM-2
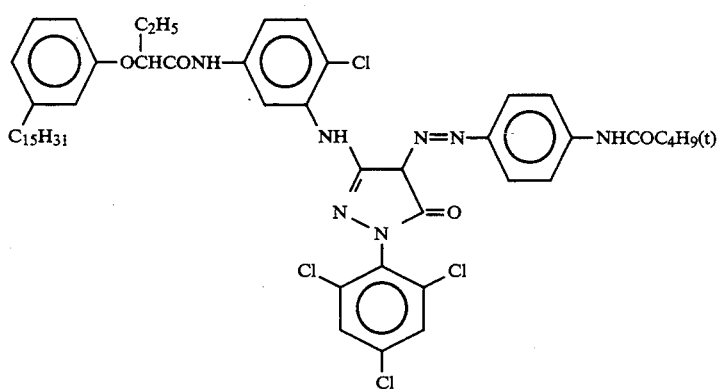
ExM-3
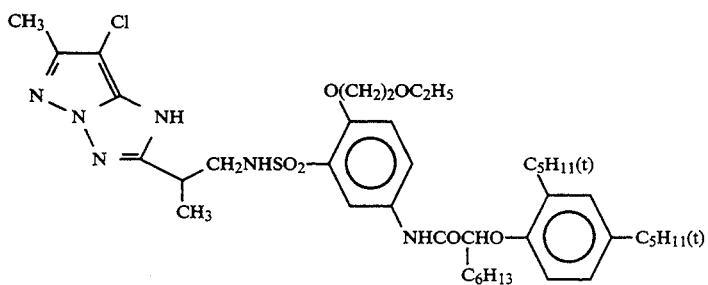
ExM-4

-continued
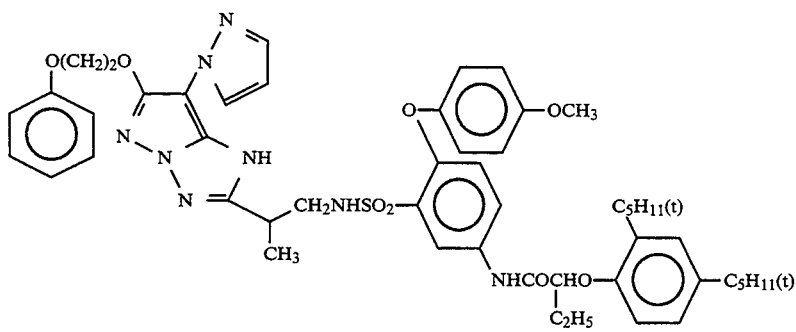
ExM-5
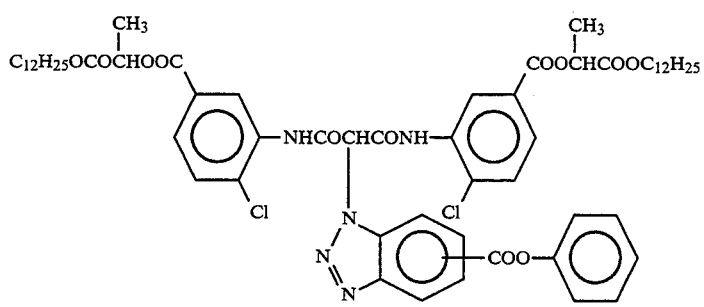
ExY-1
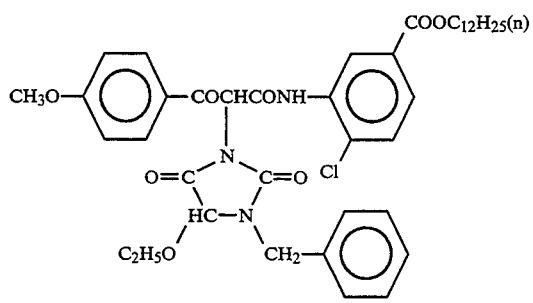
ExY-2
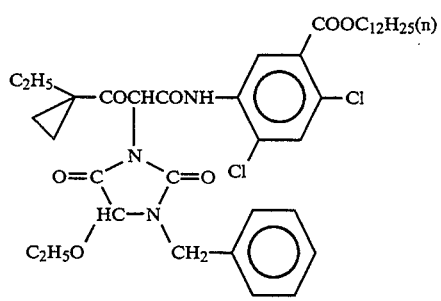
ExY-3
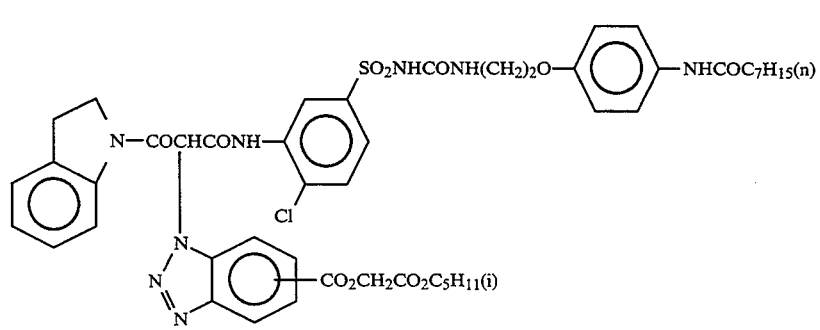
ExY-4

-continued
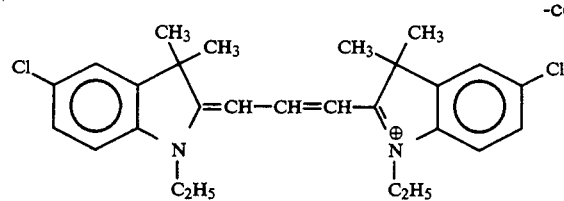  ExF-1
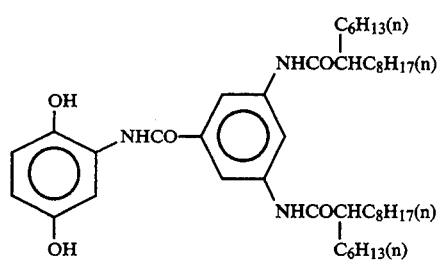  Cpd-1
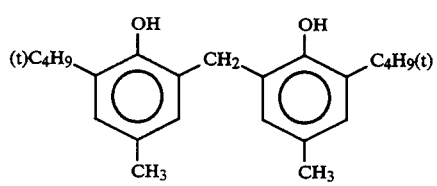  Cpd-2
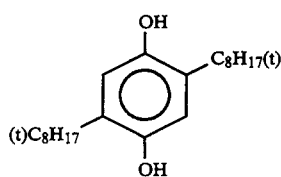  Cpd-3
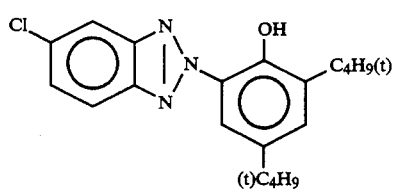  UV-1
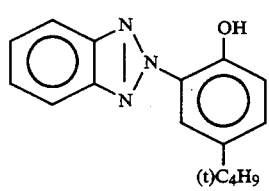  UV-2
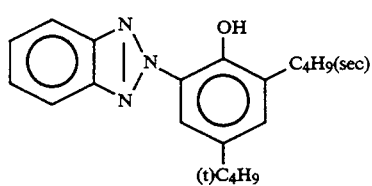  UV-3
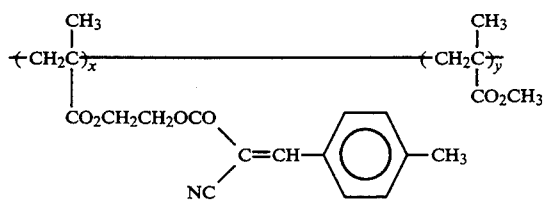  UV-4
x:y = 70:30 (wt %)

-continued
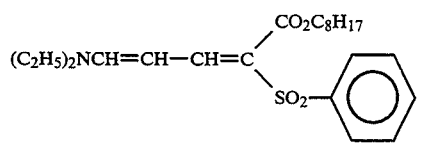 UV-5
Tricresyl phosphate HBS-1
Di-n-butyl phthalate HBS-2
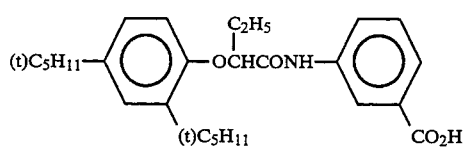 HBS-3
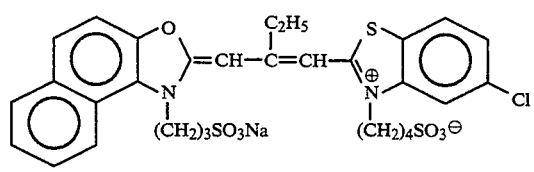 ExS-1
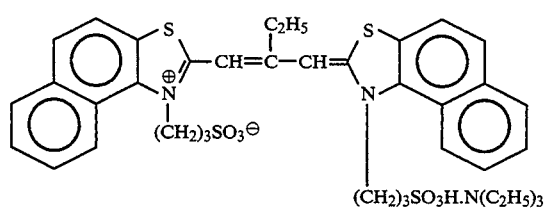 ExS-2
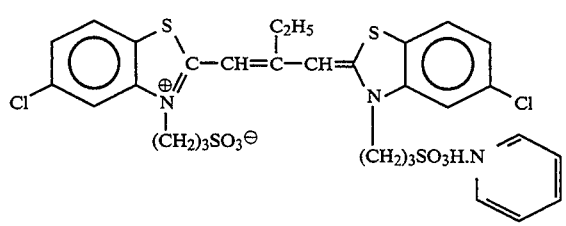 ExS-3
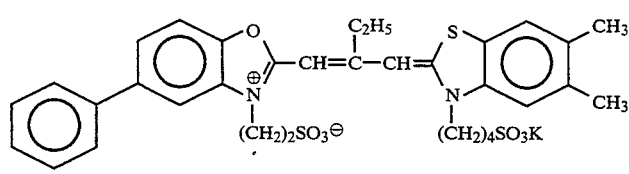 ExS-4
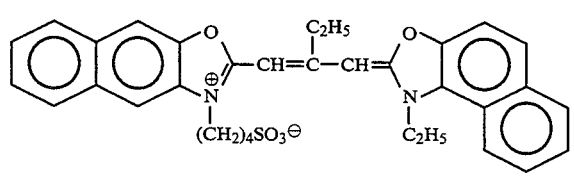 ExS-5
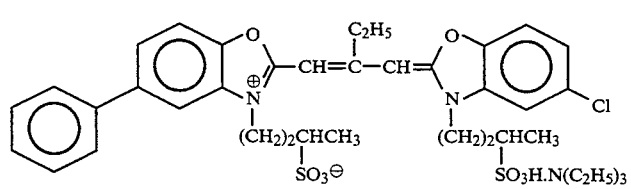 ExS-6

-continued
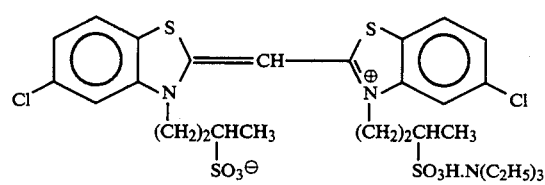
ExS-7
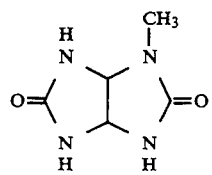
S-1
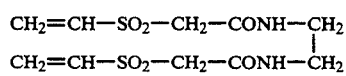
H-1
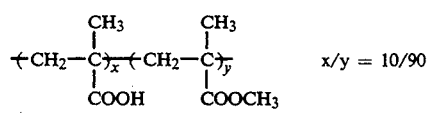  x/y = 10/90
B-1
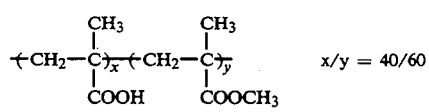  x/y = 40/60
B-2
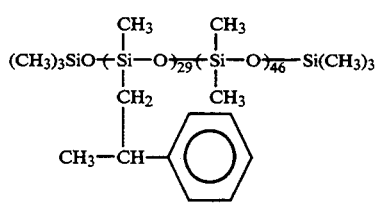
B-3
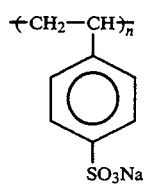
B-4
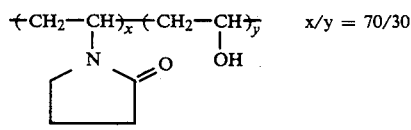  x/y = 70/30
B-5
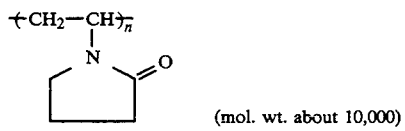
(mol. wt. about 10,000)
B-6
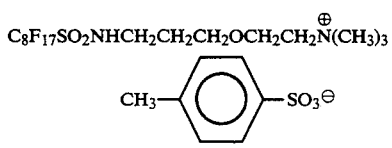
W-1
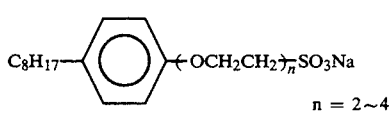
n = 2~4
W-2

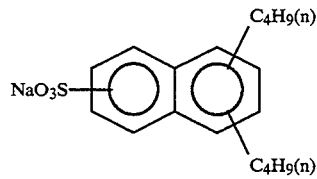
W-3
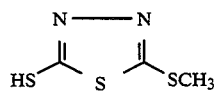
F-1
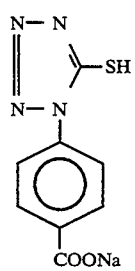
F-2
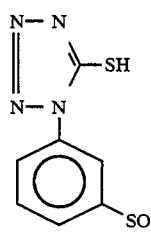
F-3
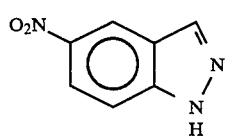
F-4
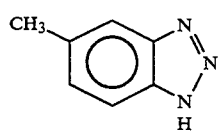
F-5
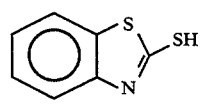
F-6
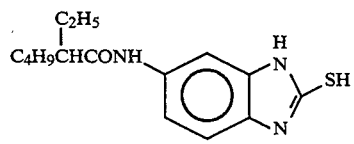
F-7
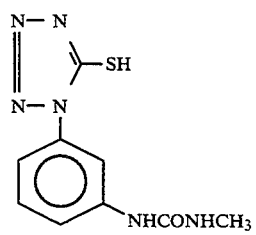
F-8
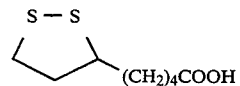
F-9

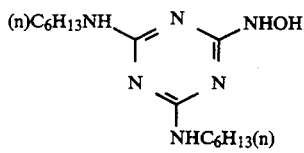
F-10

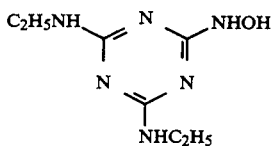
F-11

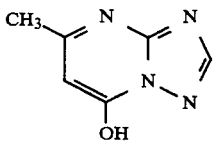
F-12

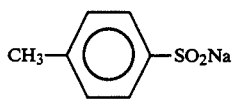
F-13

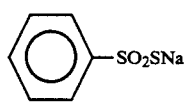
F-14

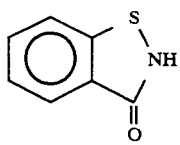
F-15

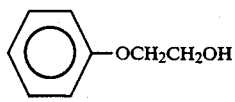
F-16

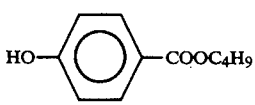
F-17

Samples 302 to 315 were prepared in the same manner as in the preparation of the sample 301 except that an equimolar amount of each of couplers indicated in Table 19 was used in place of main coupler ExM-2 used in each of the seventh layer and the eighth layer of the sample 301, and the amount of high-boiling organic solvent HBS-1 was changed as indicated in Table 19.

The thus-obtained samples 301 to 315 were exposed (1/100 second) to while light (color temperature: 5500° K.) through a wedge, and then subjected to color development processing.

Each of the samples was 35 mm in width and processed by using an automatic processor.

Processing stage

The following processing stage and the following processing solutions were used.

| Processing Stage | Processing Time | Processing Temp. (°C.) | Replenishment rate* (ml) | Tank Capacity (l) |
|---|---|---|---|---|
| Color Development | 3 min 5 sec | 38.0 | 600 | 17 |
| Bleaching | 50 sec | 38.0 | 140 | 5 |
| Blixing | 50 sec | 38.0 | — | 5 |
| Fixing | 50 sec | 38.0 | 420 | 5 |
| Rinse | 30 sec | 38.0 | 980 | 3.5 |
| Stabilization (1) | 20 sec | 38.0 | — | 3 |
| Stabilization (2) | 20 sec | 38.0 | 560 | 3 |
| Drying | 1 min 30 sec | 60 | | |

*Replenishment rate being per m² of the light-sensitive material.

The flow of the stabilizing solution was a countercurrent system of from (2) to (1). The bleaching-fixing bath was replenished with the processing solution in the following manner. The upper part of the bleaching bath of the automatic processor and the upper part of the fixing bath thereof were provided with a notch so that all of overflow solutions produced by feeding the replenishers to the bleaching bath and the fixing bath were allowed to flow into the blixing bath. The amount of the developing solution brought into the bleaching stage, that of the bleaching solution brought into the blixing stage, that of the blixing solution brought into the fixing stage and that of the fixing solution brought into the rinsing stage were 65 ml, 50 ml, 50 ml and 50 ml, respectively, each amount being per m² of the light-sensitive material. Cross-over time of each stage was 6 seconds an included in the processing time of the pre-stage.

Each processing solution had the following composition.

|  | Tank Solution (g) | Replenisher (g) |
|---|---|---|
| Color developing solution | | |
| Diethylenetriaminepentaacetic acid | 2.0 | 2.0 |
| 1-Hydroxyethylidene-1,1-diphosphonic acid | 3.3 | 3.3 |
| Sodium sulfite | 3.9 | 5.1 |
| Potassium carbonate | 37.5 | 39.0 |
| Potassium bromide | 1.4 | 0.4 |
| Potassium iodide | 1.3 mg | — |
| Hydroxylamine sulfate | 2.4 | 3.3 |
| 2-Methyl-4-[N-ethyl-N-(β-hydroxyethyl)amino]anilinesulfate | 4.5 | 6.0 |
| Water to make | 1.0 liter | 1.0 liter |
| pH | 10.05 | 10.15 |
| Bleaching solution | | |
| Ammonium 1,3-diaminopropane-tetraacetate ferrate monohydrate | 130 | 195 |
| Ammonium bromide | 70 | 105 |
| Ammonium nitrate | 14 | 21 |
| Hydroxyacetic acid | 50 | 75 |
| Acetic acid | 40 | 60 |
| Water to make | 1.0 liter | 1.0 liter |
| pH (adjusted with ammonia water) | 4.4 | 4.4 |

Blixing solution (tank solution)

A 15:85 (by volume) mixed solution pH=7.0 of the above bleaching solution (tank solution) and the fixing solution (tank solution) described below.

| Fixing solution | Tank Solution (g) | Replenisher (g) |
|---|---|---|
| Ammonium sulfite | 19 | 57 |
| Aqueous solution of ammonium thiosulfate (700 g/l) | 280 ml | 840 ml |
| Imidazole | 15 | 45 |
| Ethylenediaminetetraacetic acid | 15 | 45 |
| Water to make | 1.0 liter | 1.0 liter |
| pH (adjusted with ammonia water and acetic acid) | 7.4 | 7.45 |

Rinsing water

Tap water was passed through a mixed bed column packed with an H type strongly acidic cation exchange resin (Amberlite IR-120B manufactured by Rohm & Haas Co.) and an OH type strongly basic anion exchange resin (Amberlite IR-400) to reduce the concentration of each of calcium ion and magnesium ion to not higher than 3 mg/l. Subsequently, sodium dichlorinated isocyanurate (20 mg/l) and sodium sulfate (150 mg/l) were added thereto. The pH of the solution was in the range of 6.5 to 7.5.

Stabilizing solution

Tank solution and replenisher being the same.

|  | Amount (g) |
|---|---|
| Sodium p-toluenesulfinate | 0.03 |
| Polyoxyethylene p-monononylphenyl ether (an average degree of polymerization: 10) | 0.2 |
| Disodium ethylenediaminetetraacetate | 0.05 |
| 1,2,4-Triazole | 1.3 |
| 1,4-Bis(1,2,4-triazole-1-ylmethyl)-piperazine | 0.75 |
| Water to make | 1.0 liter |
| pH | 8.5 |

The density of each of the processed samples was measured through a green filter, and the sensitivity and color developing performance of each sample were evaluated. The logarithm value of the reciprocal of an exposure amount giving a density of (Fog+0.5) was referred to as the sensitivity. The sensitivity in terms of relative sensitivity was determined when the sensitivity of the sample 301 was referred to as standard. The color developing performance was evaluated by the density of each sample exposed by an exposure amount which gave a density of 2.0 to the sample 301.

Separately, each of the samples 301 to 315 was prepared and divided into two groups. These samples were exposed to white light through a wedge. One group was stored in a refrigerator for 7 days, and another group was stored at 30° C. and 80% RH for 10 days. The density of each sample was measured through a green filter.

There was read an exposure amount giving a density $(D^rS_{1.0})$ of (minimum density+1.0) on the characteristic curve obtained from the sample stored in the refrigerator, and the logarithm value $(S^rG)$ of the reciprocal thereof was calculated. There was read an exposure amount giving a density $(D^rS_{1.0})$ of (minimum density+1.0) on the characteristic curve obtained from the sample stored at 30° C. and 80% RH, and the logarithm value $(S^sG)$ of the reciprocal thereof was calculated. A difference $(\Delta S=S^s{}_G-S^rG)$ therebetween was evaluated as a measure of latent image stability.

The results are shown in Table 19.

TABLE 19

| Sample No. | Seventh layer | | Eight layer | | Sensitivity $\Delta S^G 0.5$ | Color density $D^G$ | Latent image stability $\Delta S^G 1.0$ | Remarks |
|---|---|---|---|---|---|---|---|---|
| | Main coupler | Amount of high-boiling organic solvent (ratio of amount of HBS-1) | Main coupler | Amount of high-boiling organic solvent (ratio of amount of HBS-1) | | | | |
| 301 | ExM-2 | 1 | ExM-2 | 1 | — | 2.00 | −0.12 | Comp. Ex. |
| 302 | M-2 | " | " | " | −0.02 | 1.92 | +0.01 | Invention |
| 303 | M-8 | " | " | " | ±0 | 2.06 | −0.02 | " |

TABLE 19-continued

|  | Seventh layer | | Eight layer | | | | | |
|---|---|---|---|---|---|---|---|---|
| Sample No. | Main coupler | Amount of high-boiling organic solvent (ratio of amount of HBS-1) | Main coupler | Amount of high-boiling organic solvent (ratio of amount of HBS-1) | Sensitivity $\Delta S^G 0.5$ | Color density $D^G$ | Latent image stability $\Delta S^G 1.0$ | Remarks |
| 304 | M-11 | " | " | " | ±0 | 2.02 | ±0 | " |
| 305 | M-12 | " | " | " | ±0 | 2.00 | −0.01 | " |
| 306 | M-13 | " | " | " | ±0 | 2.02 | −0.02 | " |
| 307 | M-37 | " | " | " | +0.02 | 2.10 | −0.01 | " |
| 308 | M-43 | " | " | " | −0.01 | 1.98 | +0.01 | " |
| 309 | M-8 | " | M-8 | " | +0.02 | 2.18 | −0.02 | " |
| 310 | M-12 | 0.5 | M-12 | 0.5 | ±0 | 1.98 | −0.01 | " |
| 311 | Comparative coupler a | 1 | comparative coupler a | 1 | −0.04 | 1.89 | −0.10 | Comp. Ex. |
| 312 | Comparative coupler b | " | ExM-2 | " | −0.05 | 1.81 | −0.07 | Comp. Ex. |
| 313 | Comparative coupler c | " | " | " | −0.05 | 1.81 | −0.08 | Comp. Ex. |
| 314 | Comparative coupler d | " | " | " | −0.05 | 1.73 | +0.04 | Comp. Ex. |
| 315 | Comparative coupler e | " | " | " | −0.07 | 1.68 | +0.06 | Comp. Ex. |

(The ratio fo the amount of HBS-1 is represented by ratio when the amount thereof used in the sample 301 is referred to as 1)
(The same comparative couplers a, b, c, d and e ad those used in Example 3 are used)

It is clear from Table 19 that the samples of the present invention are very excellent in latent image stability, scarcely cause a lowering in sensitivity and are excellent in color developability. Further, the samples of the present invention show a similar tendency to that of Example 2 with regard to hue. It is believed that the above performances are due to the specific structure of the coupler of the present invention and can be obtained by the reduction of an interaction between the coupler of the present invention and the silver halide emulsion.

It will be understood from the above disclosure that according to the present invention there can be obtained a photographic coupler and a light-sensitive material containing the same which is excellent in color reproducibility, dye image fastness to light and heat, sensitivity and color developability and scarcely causes a fluctuation in photographic characteristics even when the compositions of the processing solutions are changed and moreover which are excellent in latent image stability.

While the invention has been described in detail and with reference to specific embodiments thereof, will be apparent to one skilled in the art that various changes and modifications can be made therein without departing from the spirit and scope thereof.

What is claimed is:

1. A silver halide color photographic material comprising a support, a light-sensitive silver halide emulsion layer provided on said support, and optionally a hydrophilic colloid layer provided on said support, wherein at least one layer contains a coupler of formula (I)

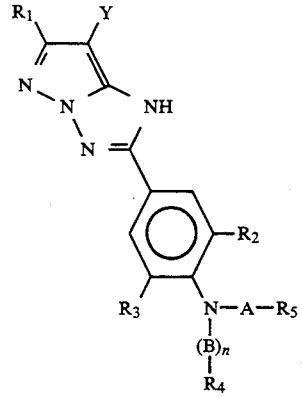

wherein $R_1$ represents tertiary alkyl group; $R_2$ and $R_3$ each represents hydrogen atom or a substituent group; Y represent hydrogen atom, a halogen atom or an aryloxy group; A and B each represents —CO— or —SO$_2$—; n represents 0 or 1; $R_4$ represents hydrogen atom, an alkyl group or an aryl group; and $R_5$ represent an alkyl group, and aryl group, an alkoxy group, an alkylamino group or an arylamino group; or $R_4$ and $R_5$ may be combined together to form a five-membered, six-membered or seven-membered ring.

2. The silver halide color photographic material according to claim 1, wherein the tertiary carbon in the tertiary alkyl group of $R_1$ is contained in a ring.

3. The silver halide color photographic material according to claim 2, wherein $R_1$ is selected from the group consisting of 1-methylcyclopropyl, 1-ethylcyclopropyl, and adamantyl.

4. The silver halide color photographic material according to claim 1, wherein $R_1$ is a tertiary alkyl group substituted with at least one substituent, each substituent being selected from the group consisting of halogen, aryl, alkoxy, aryloxy, alkylthio, arylthio, alkylcarbonyloxy, arylcarbonyloxy, alkoxycarbonyl, carbonamido, sulfonamido, carboxyl and cyano.

5. The silver halide color photographic material according to claim 1, wherein $R_1$ is an unsubstituted tertiary alkyl group.

6. The silver halide color photographic material according to claim 5, wherein $R_1$ is tertiary butyl.

7. The silver halide color photographic material according to claim 1, wherein:

$R_2$ and $R_3$ may be the same or different and each is a hydrogen atom or a substituent group selected from the group consisting of: a cyano group, a hydroxyl group, a carboxyl group, a halogen atom, an alkyl group, an aryl group, an alkoxy group, an aryloxy group, an alkoxycarbonyl group, a carbamoyl group, and a sulfamoyl group.

8. The silver halide color photographic material according to claim 7, wherein:

$R_2$ and $R_3$ may be the same or different and each is a hydrogen atom, an alkyl group, or an alkoxy group.

9. The silver halide color photographic material according to claim 8, wherein $R_2$ and $R_3$ are hydrogen atoms.

10. The silver halide color photographic material according to claim 1, wherein:

$R_4$ is a hydrogen atom, a substituted or unsubstituted alkyl group or a substituted or unsubstituted aryl group, wherein said substituted groups are substituted with a substituent selected from the group consisting of: a halogen atom, a hydroxyl group, a cyano group, a carboxyl group, an aryl group, an alkoxy group, an aryloxy group, an alkylthio group, an arylthio group, an oxycarbonyl group, a carbonyloxy group, a carbonamido group, a sulfonamido group, a carbamoyl group, a sulfamoyl group, an imido group, a urethane group, a ureido group and a sulfonyl group;

$R_5$ is a substituted or unsubstituted alkyl group, a substituted or unsubstituted aryl group, a substituted or unsubstituted alkoxy group, a substituted or unsubstituted alkylamino group, or a substituted or unsubstituted arylamino group, wherein said substituted groups are substituted with a substituent selected from the group consisting of: a halogen atom, a hydroxyl group, a cyano group, a carboxyl group, an aryl group, an alkoxy group, an aryloxy group, an alkythio group, an arylthio group, an oxycarbonyl group, a carbonyloxy group, a carbonamido group, a sulfonamido group, a carbamoyl group, a sulfamoyl group, an imido group, a urethane group, a ureido group and a sulfonyl group;

optionally $R_4$ and $R_5$ may be combined together to form a substituted or unsubstituted five-membered, six-membered or seven-membered ring, wherein said substituted rings are substituted with a substituent selected from the group consisting of: a cyano group, a hydroxyl group, a carboxyl group, a halogen atom, an alkyl group, an aryl group, an alkoxy group, an aryloxy group, an alkoxycarbonyl group, a carbamoyl group and a sulfamoyl group.

11. The silver halide color photographic material according to claim 1, wherein n is 0, and $R_4$ is hydrogen atom.

12. The silver halide color photographic material according to claim 10, wherein:

$R_5$ is an alkyl group substituted with a substituent selected from the group consisting of: an alkoxy group, an aryloxy group an alkylthio group, an arylthio group, an alkoxycarbonyl group, an aryloxycarbonyl group, a carbonamido group, a urethane group, a ureido group, an imido group, a sulfonamido group, and a sulfonyl group.

13. The silver halide color photographic material according to claim 12, wherein $R_5$ is an alkyl group substituted with alkoxycarbonyl group.

14. The silver halide color photographic material according to claim 1, wherein:

Y is a hydrogen atom, a halogen atom, or a substituted or unsubstituted aryloxy group, wherein said substituted aryloxy group is substituted by a substituent selected from the group consisting of: a halogen atom, a hydroxyl group, a cyano group, a carboxyl group, an aryl group, an alkoxy group, an aryloxy group, an alkylthio group, an arylthio group, an oxycarbonyl group, a carbonyloxy group, a carbonamido group, a sulfonamido group, a carbamoyl group, a sulfamoyl group, an imido group, a urethane group, a ureido group, and a sulfonyl group.

15. The silver halide color photographic material according to claim 14, wherein Y is a halogen atom.

16. The silver halide color photographic material according to claim 1, wherein A is —CO—.

17. The silver halide color photographic material according to claim 1, wherein said coupler of formula (I) is contained in said light-sensitive silver halide emulsion layer.

18. A silver halide color photographic material as in claim 17, wherein said coupler is contained in an amount of $1 \times 10^{-3}$ to 1 mol per mol of silver halide in said layer.

19. The silver halide color photographic material according to claim 1, wherein said material comprises at least one blue-sensitive silver halide emulsion layer, at least one green-sensitive silver halide emulsion layer, and at least one red-sensitive silver halide emulsion layer.

20. The silver halide color photographic material according to claim 19, wherein said coupler of formula (I) is contained in at least one of said green-sensitive silver halide emulsion layers or in a hydrophilic layer adjacent thereto.

21. The silver halide color photographic material according to claim 20, wherein said coupler of formula (I) is a magenta coupler and is contained in at least one green-sensitive silver halide emulsion layer in an amount of $2 \times 10^{-3}$ to $3 \times 10^{-1}$ mol per mol of silver halide in the emulsion layer.

* * * * *